US009186318B2

(12) United States Patent
Yun et al.

(10) Patent No.: US 9,186,318 B2
(45) Date of Patent: Nov. 17, 2015

(54) QUINOLYL-CONTAINING HYDROXAMIC ACID COMPOUND AND PREPARATION METHOD THEREOF, AND PHARMACEUTICAL COMPOSITION CONTAINING THIS COMPOUND AND USE THEREOF

(75) Inventors: Ziwei Yun, Guangdong (CN); Hongtao Wang, Guangdong (CN)

(73) Assignee: Beijing Konruns Pharmaceutical Co., Ltd, Beijing (CN)

( * ) Notice: Subject to any disclaimer, the term of this patent is extended or adjusted under 35 U.S.C. 154(b) by 0 days.

(21) Appl. No.: 14/345,922

(22) PCT Filed: Sep. 27, 2011

(86) PCT No.: PCT/CN2011/080213
§ 371 (c)(1),
(2), (4) Date: Apr. 3, 2014

(87) PCT Pub. No.: WO2013/040801
PCT Pub. Date: Mar. 28, 2013

(65) Prior Publication Data
US 2014/0221425 A1 Aug. 7, 2014

(30) Foreign Application Priority Data

Sep. 19, 2011 (CN) .......................... 2011 1 0278403

(51) Int. Cl.
| *A61K 9/06* | (2006.01) |
| *A61K 9/00* | (2006.01) |
| *C07D 401/12* | (2006.01) |
| *C07D 215/22* | (2006.01) |
| *C07D 215/233* | (2006.01) |
| *A61K 47/10* | (2006.01) |
| *A61K 9/20* | (2006.01) |
| *A61K 9/48* | (2006.01) |

(52) U.S. Cl.
CPC ............... *A61K 9/0014* (2013.01); *A61K 9/008* (2013.01); *A61K 9/0019* (2013.01); *A61K 9/0031* (2013.01); *A61K 9/0043* (2013.01); *A61K 9/0048* (2013.01); *A61K 9/0053* (2013.01); *A61K 9/06* (2013.01); *A61K 9/2054* (2013.01); *A61K 9/4866* (2013.01); *A61K 47/10* (2013.01); *C07D 215/22* (2013.01); *C07D 215/233* (2013.01); *C07D 401/12* (2013.01)

(58) Field of Classification Search
CPC ..... A61K 9/0014; A61K 9/06; A61K 9/2054; A61K 9/4866; A61K 9/008; A61K 9/0053; A61K 9/0048; A61K 9/0043; A61K 9/0031; C07D 215/22; C07D 215/233
See application file for complete search history.

(56) References Cited

U.S. PATENT DOCUMENTS

2014/0248378 A1 * 9/2014 Cockcroft et al. ............ 424/722

FOREIGN PATENT DOCUMENTS

| CN | 1228083 | 9/1999 |
| CN | 1839121 | 9/2006 |

* cited by examiner

*Primary Examiner* — D Margaret M. Seaman
(74) *Attorney, Agent, or Firm* — Stites & Harbison PLLC; Cong Ding

(57) ABSTRACT

Provided in the present invention is a quinolyl-containing hydroxamic acid compound as shown in formula (I), at the same time also disclosed is the preparation method of the compound and the use thereof, and a pharmaceutical composition containing the quinolyl-containing hydroxamic acid compound. Such compounds are inhibitors of protein kinases and/or histone deacetylases, and can be used in the treatment of diseases caused by the abnormal activity of protein kinases and/or histone deacetylases, for example, tumors, etc.

26 Claims, 3 Drawing Sheets

QUINOLYL-CONTAINING HYDROXAMIC ACID COMPOUND AND PREPARATION METHOD THEREOF, AND PHARMACEUTICAL COMPOSITION CONTAINING THIS COMPOUND AND USE THEREOF

CROSS REFERENCE TO RELATED APPLICATIONS

This application is a §371 National State Application of PCT/CN2011/080213 filed Sep. 27, 2011, which claims priority to CN 201110278403.9 filed Sep. 19, 2011.

TECHNICAL FIELD OF THE INVENTION

The present invention relates to the organic chemistry and medicinal chemistry, particularly a quinolyl-containing hydroxamic acid compound and the preparation method thereof, and the pharmaceutical composition containing the compound and the use thereof.

BACKGROUND OF THE INVENTION

Protein kinases are a kind of phosphotransferases, and the role thereof is to transfer the gamma-phosphate group of ATP into a specific amino acid residue of a substrate to phosphorylate a protein, therefore exerting its physiological and biochemical functions. The protein kinases are an important class of kinases. In signal transduction, their main functions lie in two aspects: one is to regulate the activity of the protein by phosphorylation; the other is to amplify progressively the signal by progressive phosphorylation of protein so as to cause cellular reaction.

Abnormal protein kinase activity is not only closely related to the abnormality of certain steps in a series of intracellular signal transduction pathways, such as tumor proliferation, apoptosis and metastasis, but also the main reason that leads to a range of other human diseases related to inflammatory or proliferative response, such as rheumatoid arthritis, cardiovascular and neurological diseases, asthma, psoriasis. More than four hundred kinds of human diseases have been known to be related directly or indirectly to the protein kinase, which makes the protein kinase become another important class of drug targets after the G-protein-coupled receptors.

Protein kinase family consists of more than 500 members, which usually can be divided into two classes, i.e. the protein tyrosine kinases (PTKs) and serine-threonine kinases. In accordance with the location of the kinase in the cells, they can also be divided into receptor kinase and non-receptor kinase which is also known as the intracellular kinase. Receptor kinases generally belong to the tyrosine kinases and are also referred to as receptor tyrosine kinases (RTKs). Such a receptor kinase is composed of an extracellular portion, a transmembrane region and an intracellular portion. The portion of kinase having catalytic activity is located in the cytoplasm. The overwhelming majority of serine-threonine kinases are located within the cells and belong to non-receptor kinases, also called cytoplasmic kinases.

A typical representative of the RTKs family is growth factor receptors, which may be divided into at least 19 subfamilies. The following are several major subfamilies:

(a) HER family receptor tyrosine kinases, including EGFR (epithelial growth factor receptor), HER2, HER3 and HER4. EGFR is the target of synthetic small molecules drug Tarceva®, Tykerb® and the monoclonal antibody Erbitux® for the treatment of non-small cell lung cancer.

(b) the subfamily consisting of insulin receptor (IR), insulin-like growth factor I receptor (IGF-1R) and insulin receptor-related receptor (IRR), wherein, IGF-1R is a well-established anti-cancer target, but because it is too similar with IR, especially in the intracellular kinase portion in which the amino acid sequence is 100% identical to the corresponding amino acid sequence of IR, it can inhibit the activity of the IGF-1R while typically inhibiting the activity of IR. There is evidence that IR is also an efficient anti-cancer target. However, it is necessary to find the balance of effectiveness and safety risks with regard to IR inhibitors for anti-cancer because the inhibition of IR leads to the risk of elevated blood sugar.

(c) Platelet-derived growth factor receptor (PDGFR) family, including PDGFR-α, PDGFR-β, CSF1R, c-KIT and c-fms, wherein the c-Kit is also the molecular target of the drug Gleevec® for treatment of leukemia treatment and is used to treat gastrointestinal stromal tumors.

(d) Vascular endothelial growth factor receptor (VEGFR) family, including FLT1 (Fms-like tyrosine kinase 1 or VEGFR1), KDR (or VEGFR-2) and FLT4 (or VEGFR3), the members of which are molecular targets for Sutent® and Naxavar®.

(e) Fibroblast growth factor receptor (FGFR) family, including FGFR1, FGFR2, FGFR3 and FGFR4 as well as seven ligands FGF1, FGF2, FGF3, FGF4, FGF5, FGF6, and FGF7, the members of which are still in clinical trials as molecular target drugs.

(f) MET family, including c-Met also known as human hepatocyte growth factor receptor (hHGFR) and RON, wherein c-Met plays an important role in the growth and metastasis of initial tumors. The members of the family are still in clinical trials as a molecular target drug.

(g) RET family. RET is a receptor of GDNF family members, having RET51, RET43 and RET9 isoforms. It is still in clinical trials as a molecular target drug.

(h) Eph family, being the biggest family of receptor tyrosine kinase and consisting of 16 receptors (EPHA1, EphA2, EPHA3, EPHA4, EPHA5, EPHA6, EPHA7, EPHA8, EPHA9, EPHA10, EPHB1, EPHB2, EPHB3, EPHB4, EPHB5, EPHB6) and 9 ligands (EFNA1, EFNA2, EFNA3, EFNA4, EFNA5, EFNB1, EFNB2, EFNB3). These members play an important role in the development of the animal and some members play a role in tumors.

AXL is another important receptor tyrosine kinase. AXL is also known as UFO/ARK/Tyro, and the ligand thereof is a vitamin K-dependent growth promoting factor GAS6. AXL is firstly found as transforming gene in chronic myeloid leukemia (CML). AXL is overexpressed in metastatic colon cancer, thyroid cancer, breast cancer, prostate cancer and melanoma Inhibition of AXL activity may play a role in inhibiting tumor growth, proliferation and metastasis.

The non-receptor kinase does not have the extracellular portion or the transmembrane region, and the entire kinase is in the cytoplasm. It is currently known that there are at least 24 kinds of non-receptor kinases which are divided into 11 subfamilies, i.e. Src, Frk, Btk, CsK, Abl, Zap70, Fes, Fps, Fak, Jak and ACK subfamily. The Src subfamily is the biggest one, and includes Src, Yes, Fyn, Lyn, Lck, Blk, Hck, Fgr, AUR1, AUR2 and Yrk kinase. For details, see Neet, K.; Hunter, T. *Genes to Cells* 1996, 1, 147-169, and the references cited therein. Although several non-receptor kinases are tyrosine kinases, the majority of non-receptor kinases are serine-threonine kinases. Several members therein are the molecular target for the drugs Gleevec® and Sprycel® for treatment of leukemia.

As mentioned above, the receptor kinases and non-receptor kinases have been proved as anti-tumor targets in the clinical and practical applications, and several anti-tumor drugs have been approved for marketing for treatment of patients. In addition to treatment of tumors, the abnormal activity of inhibition of receptor kinases and non-receptor kinases can also be used for treating the following diseases, including but not limited to psoriasis or serpedo, cirrhosis, diabetes, diseases involving angiogenesis, diseases involving restenosis, eye diseases, age-related macular degeneration, rheumatoid arthritis and other inflammation, immune system diseases such as autoimmune diseases, cardiovascular diseases such as atherosclerosis, kidney disease. Therefore it is necessary to continue to develop inhibitors of these kinases.

Histone deacetylase (HDAC) is a class of enzymes widely found in bacteria, fungi, plants and animals, whose role is to remove acetyl from the amino groups of the core histone N-terminal lysine residues, which causes the core histone N-terminal positively charged to enhance the combination with the negatively charged DNA, and thereby preventing the transcription machinery from contacting with the DNA template. According to their homology to fungal proteins, histone deacetylases (HDAC) are divided into four classes: class I includes HDAC1, HDAC2, HDAC3 and HDAC8, which are homologous to the fungal protein RPD3; class II includes HDAC4, HDAC5, HDAC7 and HDAC9 which are homologous to the fungal protein HDA1; class IIa includes HDAC6 and HDAC 10 containing two catalytic point; class IV includes HDAC11, the catalytic center thereof contains the amino acid residues shared with class I and II HDAC. The catalytic sites of the 11 HDAC isoforms have zinc ions, and may be inhibited by hydroxamic acid compounds such as SAHA (Vorinostat), trichostatin A (TSA). HDAC inhibitors as mood stabilizers and anti-epileptic drugs have a long history in psychiatry and neurology. HDAC inhibitors are investigated for use in treatment of neurodegenerative diseases such as Alzheimer's disease, Huntington's disease, Parkinson's disease. Another large class of applications of HDAC inhibitors are used as anticancer drugs, the representative example thereof is Vorinostat developed by Merck, which is approved by FDA for treatment of metastatic cutaneous T-cell lymphoma (CTCL) in 2006. The treatment of other tumors including solid tumors and leukemia by HDAC inhibitors is being in clinical trials.

SUMMARY OF THE INVENTION

One purpose of the present invention is to provide a quinolyl-containing hydroxamic acid compound that has protein kinase and/or histone deacetylase inhibitory activity, and its preparation method thereof.

Another purpose of the present invention is to provide the use of said quinolyl-containing hydroxamic acid compound for preparation of a pharmaceutical composition for treatment of diseases caused by abnormal activity of protein kinase and/or histone deacetylase.

A further purpose of the present invention is to provide a pharmaceutical composition comprising said quinolyl-containing hydroxamic acid, which is capable of treating the diseases caused by abnormal activity of protein kinase and/or histone deacetylase.

DETAILED DESCRIPTION OF THE INVENTION

A quinolyl-containing hydroxamic acid compound is provided, and its molecular structure is represented by formula (I) below:

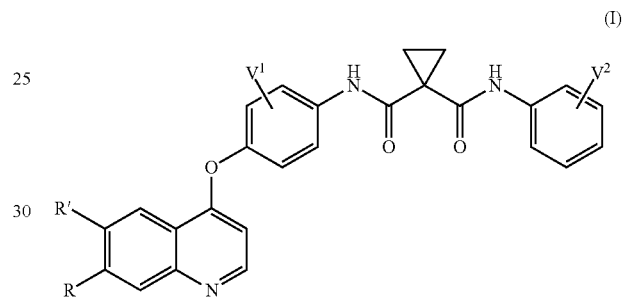

wherein, $V^1$ and $V^2$ each independently represents a hydrogen, halogen, $-OCF_3$, $-CF_3$, $-NO_2$, $-CN$, $-OH$, $-NH_2$, $-NMe_2$, $C_{1-6}$ alkyl, $C_{2-6}$ alkenyl, $C_{2-6}$ alkynyl, $C_{3-6}$ cycloalkyl, $C_{3-12}$ heteroalicyclyl, $C_{1-6}$ alkoxy, $C_{3-6}$ cycloalkyloxy or $C_{3-12}$ heteroalicyclyloxy group;

Either of R and R' represents the hydroxamic acid-containing Q group and the other represents a hydrogen, methoxy, methoxyethoxy or the hydroxamic acid-containing Q group, wherein the hydroxamic acid-containing Q group is represented by

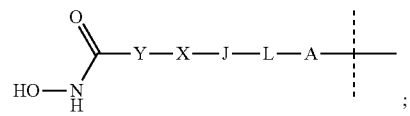

A represents O, NH, $S(=O)_m$, $C_{1-6}$ alkyl, or A is absent, and the hydrogen of A may be substituted with $G^1$;

L represents $C_{1-6}$ alkyl, $C_{2-6}$ alkenyl, $C_{2-6}$ alkynyl, $C_{3-6}$ cycloalkyl, $C_6$ aryl, $C_{5-6}$ heteroaryl, $C_{3-12}$ heteroalicyclyl, or L is absent, and the hydrogen of L may be substituted with $G^2$;

J represents O, NH, $S(=O)_m$, $C_{1-6}$ alkyl, $C_{2-6}$ alkenyl, $C_{2-6}$ alkynyl, $C_{3-6}$ cycloalkyl, $C_6$ aryl, $C_{5-6}$ heteroaryl, $C_{3-12}$ heteroalicyclyl, or J is absent, and the hydrogen of J may be substituted with $G^3$;

X represents —C(=O)—, —S(O)$_m$, C$_{1-6}$ alkyl, C$_{2-6}$ alkenyl, C$_{2-6}$ alkynyl, C$_{3-6}$ cycloalkyl, C$_6$ aryl, C$_{5-6}$ heteroaryl, C$_{3-12}$ heteroalicyclyl, or X is absent, and the hydrogen of X may be substituted with G$^4$;

Y represents C$_{1-6}$ alkyl, C$_{2-6}$ alkenyl, C$_{2-6}$ alkynyl, C$_{3-6}$ cycloalkyl, C$_6$ aryl, C$_{5-6}$ heteroaryl, C$_{3-12}$ heteroalicyclyl, or Y is absent, and the hydrogen of Y may be substituted with G$^5$;

wherein,

G$^1$, G$^2$, G$^3$, G$^4$ and G$^5$ each independently represent H, —CN, —CF$_3$, —CO$_2$H, halogen, C$_{1-6}$ alkyl, C$_{3-6}$ cycloalkyl, C$_{2-6}$ alkenyl, C$_{2-6}$ alkynyl, C$_6$ aryl, C$_{5-6}$ heteroaryl, C$_{3-12}$ heteroalicyclyl, R$^1$O—, R$^1$R$^2$N—, R$^1$S(=O)$_m$—, R$^1$R$^2$NS(=O)$_m$—, R$^3$C(=O)—, R$^1$R$^2$NC(=O)—, R$^1$OC(=O)—, R$^3$C(=O)O—, R$^1$R$^2$NC(=O)O—, R$^3$C(=O)NR$^1$—, R$^1$R$^2$NC(=O)NR$^4$—, R$^1$OC(=O)NR$^4$—, R$^1$S(=O)$_m$NR$^4$—, R$^1$R$^2$NS(=O)$_m$NR$^4$—, R$^1$R$^2$NC(=NR$^5$)NR$^4$—, R$^1$R$^2$NC(=CHNO$_2$)NR$^4$—, R$^1$R$^2$NC(=N—CN)NR$^4$—, R$^1$R$^2$NC(=NR$^5$)—, R$^1$S(=O)(=NR$^5$)NR$^4$— or R$^1$R$^2$NS(=O)(=NR$^5$)—;

R$^1$, R$^2$, R$^3$, R$^4$ and R$^5$ each independently represent H, C$_{1-6}$ alkyl, C$_{2-6}$ alkenyl, C$_{2-6}$ alkynyl, C$_{3-6}$ cycloalkyl, C$_6$ aryl, C$_{5-6}$ heteroaryl or C$_{3-12}$ heteroalicyclyl; when R$^1$ and R$^2$ are connected with the same nitrogen atom, they may form a C$_{3-12}$ heteroalicyclyl ring together with the nitrogen atom they are attached to, and this C$_{3-12}$ heteroalicyclyl ring may further comprise one or more hetero atom selected from O, N, or S(=O)$_m$; the hydrogen of R$^1$, R$^2$, R$^3$, R$^4$ and R$^5$ may be substituted with halogen, CN, C$_{1-6}$ alkyl or C$_{3-6}$ cycloalkyl;

m=0-2.

The structure of a quinolyl-containing hydroxamic acid compound is represented by formula (Ia) below:

wherein,

V$^1$ and V$^2$ each independently represents a hydrogen, halogen, —OCF$_3$, —CF$_3$, —CN, —NMe$_2$, C$_{1-6}$ alkyl, C$_{3-6}$ cycloalkyl, C$_{3-12}$ heteroalicyclyl, C$_{1-6}$ alkoxy, C$_{3-6}$ cycloalkyloxy or C$_{3-12}$ heteroalicyclyloxy group;

A represents O, NH, or S(=O)$_m$, and the hydrogen of A may be substituted with G$^1$;

L represents C$_{1-6}$ alkyl or C$_{3-6}$ cycloalkyl, and the hydrogen of L may be substituted with G$^2$;

J represents O, NH, or S(=O)$_m$, and the hydrogen of J may be substituted with G$^3$;

Y represents C$_{1-6}$ alkyl or C$_{3-6}$ cycloalkyl, and the hydrogen of Y may be substituted with G$^5$;

m=0-2.

The structure of a quinolyl-containing hydroxamic acid compound is represented by the formula (Ib) below:

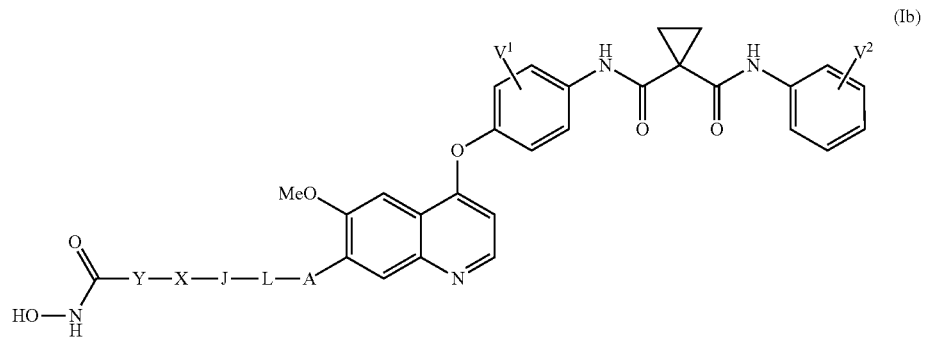

(Ib)

wherein,

V$^1$ and V$^2$ each independently represents a hydrogen, halogen, —OCF$_3$, —CF$_3$, —CN, —NMe$_2$, C$_{1-6}$ alkyl, C$_{3-6}$ cycloalkyl, C$_{3-12}$ heteroalicyclyl, C$_{1-6}$ alkoxy, C$_{3-6}$ cycloalkyloxy or C$_{3-12}$ heteroalicyclyloxy group;

A represents O, NH, or S(=O)$_m$, and the hydrogen of A may be substituted with G$^1$;

L represents C$_{1-6}$ alkyl, and the hydrogen of L may be substituted with G$^2$;

J represents C$_{3-6}$ cycloalkyl or C$_{3-12}$ heteroalicyclyl, and the hydrogen of J may be substituted with G$^3$;

X represents —C(=O)—, —S(=O)$_m$ or X is absent;

Y represents C$_{1-6}$ alkyl or C$_{3-6}$ cycloalkyl, and the hydrogen of Y may be substituted with G$^5$;

m=0-2.

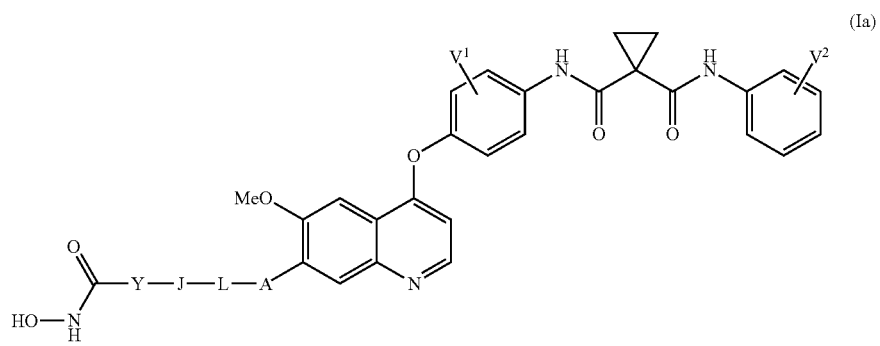

(Ia)

The structure of a quinolyl-containing hydroxamic acid compound is represented by the formula (Ic) below:

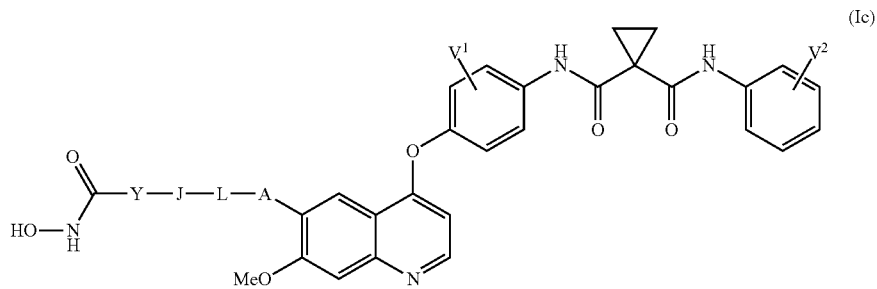

(Ic)

wherein, $V^1$ and $V^2$ each independently represents a hydrogen, halogen, —$OCF_3$, —$CF_3$, —CN, —$NMe_2$, $C_{1-6}$ alkyl, $C_{3-6}$ cycloalkyl, $C_{3-12}$ heteroalicyclyl, $C_{1-6}$ alkoxy, $C_{3-6}$ cycloalkyloxy or $C_{3-12}$ heteroalicyclyloxy group;

A represents O, NH, or $S(=O)_m$, and the hydrogen of A may be substituted with $G^1$;

L represents $C_{1-6}$ alkyl or $C_{3-6}$ cycloalkyl, and the hydrogen of L may be substituted with $G^2$;

J represents O, NH, or $S(=O)_m$, and the hydrogen of J may be substituted with $G^3$;

Y represents $C_{1-6}$ alkyl or $C_{3-6}$ cycloalkyl, and the hydrogen of Y may be substituted with $G^5$;

m=0-2.

The structure of a quinolyl-containing hydroxamic acid compound is represented by the formula (Id) below:

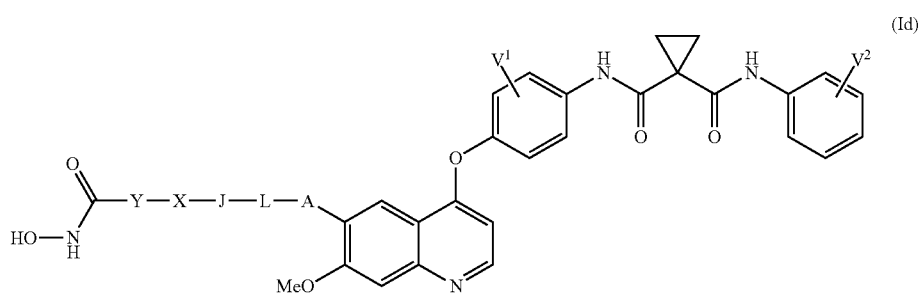

(Id)

wherein, $V^1$ and $V^2$ each independently represents a hydrogen, halogen, —$OCF_3$, —$CF_3$, —CN, —$NMe_2$, $C_{1-6}$ alkyl, $C_{3-6}$ cycloalkyl, $C_{3-12}$ heteroalicyclyl, $C_{1-6}$ alkoxy, $C_{3-6}$ cycloalkyloxy or $C_{3-12}$ heteroalicyclyloxy group;

A represents O, NH, or $S(=O)_m$, and the hydrogen of A may be substituted with $G^1$;

L represents $C_{1-6}$ alkyl, and the hydrogen of L may be substituted with $G^2$;

J represents $C_{3-6}$ cycloalkyl or $C_{3-12}$ heteroalicyclyl, and the hydrogen of J may be substituted with $G^3$;

X represents —C(=O)—, —$S(=O)_m$, or X is absent;

Y represents $C_{1-6}$ alkyl or $C_{3-6}$ cycloalkyl, and the hydrogen of Y may be substituted with $G^5$;

m=0-2.

The structure of a quinolyl-containing hydroxamic acid compound is represented by the formula (Ie) below:

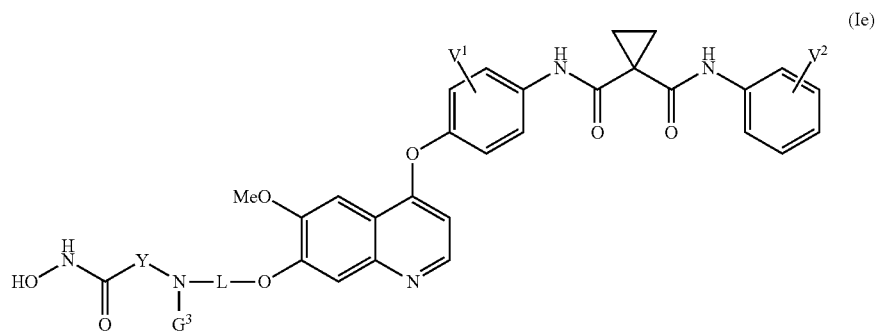

(Ie)

Wherein, $V^1$ and $V^2$ each independently represents a hydrogen, halogen, —OCF$_3$, —CF$_3$, —CN, —NMe$_2$, $C_{1-6}$ alkyl, $C_{3-6}$ cycloalkyl, $C_{3-12}$ heteroalicyclyl, $C_{1-6}$ alkoxy, $C_{3-6}$ cycloalkyloxy or $C_{3-12}$ heteroalicyclyloxy group;

L represents $C_{1-6}$ alkyl or $C_{3-6}$ cycloalkyl, and the hydrogen of L may be substituted with $G^2$;

Y represents $C_{1-6}$ alkyl or $C_{3-6}$ cycloalkyl, and the hydrogen of Y may be substituted with $G^5$.

The structure of a quinolyl-containing hydroxamic acid compound is represented by the formula (If) below:

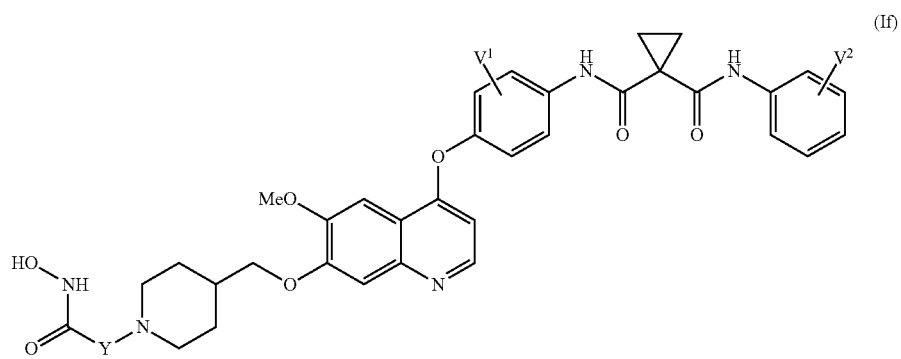

(If)

wherein, $V^1$ and $V^2$ each independently represents a hydrogen, halogen, —OCF$_3$, —CF$_3$, —CN, —NMe$_2$, $C_{1-6}$ alkyl, $C_{3-6}$ cycloalkyl, $C_{3-12}$ heteroalicyclyl, $C_{1-6}$ alkoxy, $C_{3-6}$ cycloalkyloxy or $C_{3-12}$ heteroalicyclyloxy group;

Y represents $C_{1-6}$ alkyl or $C_{3-6}$ cycloalkyl, and the hydrogen of Y may be substituted with $G^5$.

The structure of a quinolyl-containing hydroxamic acid compound is represented by the formula (Ig) below:

(Ig)

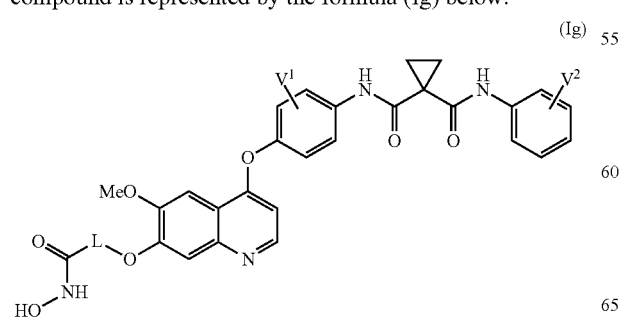

wherein,

V¹ and V² each independently represents a hydrogen, halogen, —OCF₃, —CF₃, —CN, —NMe₂, $C_{1-6}$ alkyl, $C_{3-6}$ cycloalkyl, $C_{3-12}$ heteroalicyclyl, $C_{1-6}$ alkoxy, $C_{3-6}$ cycloalkyloxy or $C_{3-12}$ heteroalicyclyloxy group;

L represents $C_{1-6}$ alkyl or $C_{3-6}$ cycloalkyl, and the hydrogen of L may be substituted with $G^2$.

The structure of a quinolyl-containing hydroxamic acid compound is represented by the formula (Ih) below:

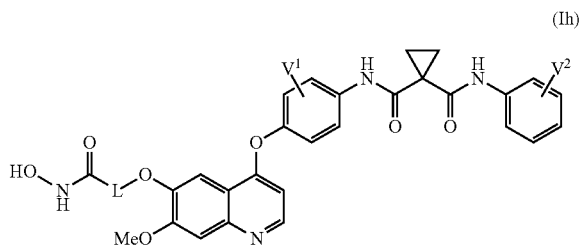

(Ih)

wherein,

V¹ and V² each independently represents a hydrogen, halogen, —OCF₃, —CF₃, —CN, —NMe₂, $C_{1-6}$ alkyl, $C_{3-6}$ cycloalkyl, $C_{3-12}$ heteroalicyclyl, $C_{1-6}$ alkoxy, $C_{3-6}$ cycloalkyloxy or $C_{3-12}$ heteroalicyclyloxy group;

L represents $C_{1-6}$ alkyl or $C_{3-6}$ cycloalkyl, and the hydrogen of L may be substituted with $G^2$.

The structure of a quinolyl-containing hydroxamic acid compound is represented by the formula (Ii) below:

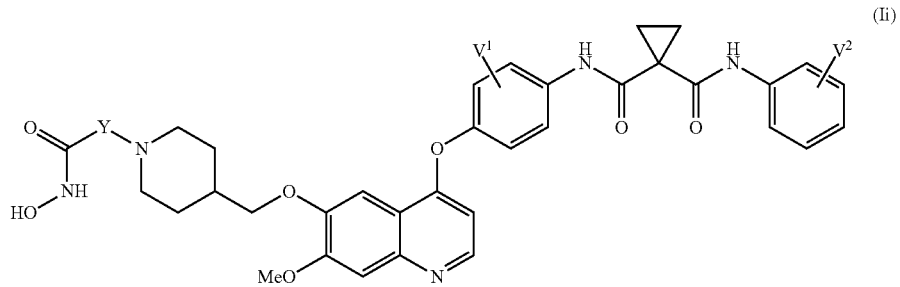

(Ii)

wherein,

V¹ and V² each independently represents a hydrogen, halogen, —OCF₃, —CF₃, —CN, —NMe₂, $C_{1-6}$ alkyl, $C_{3-6}$ cycloalkyl, $C_{3-12}$ heteroalicyclyl, $C_{1-6}$ alkoxy, $C_{3-6}$ cycloalkyloxy or $C_{3-12}$ heteroalicyclyloxy group;

Y represents $C_{1-6}$ alkyl or $C_{3-6}$ cycloalkyl, and the hydrogen of Y may be substituted with $G^5$.

A quinolyl-containing hydroxamic acid compound is any one of the following compounds:

N1'-[3-fluoro-4-[[7-[[1-[2-(hydroxyamino)-2-oxoethyl]-4-piperidinyl]methoxy]-6-methoxy-4-quinolyl]oxy]phenyl]-N1-(4-fluorophenyl)cyclopropane-1,1-dicarboxamide;

N1'-[3-fluoro-4-[[7-[3-[[2-(hydroxyamino)-2-oxoethyl]amino]propoxy]-6-methoxy-4-quinolyl]oxy]phenyl]-N1-(4-fluorophenyl)cyclopropane-1,1-dicarboxamide;

N1'-[3-fluoro-4-[[7-[3-[[3-(hydroxyamino)-3-oxopropyl]amino]propoxy]-6-methoxy-4-quinolyl]oxy]phenyl]-N1-(4-fluorophenyl)cyclopropane-1,1-dicarboxamide;

N1'-[3-fluoro-4-[[7-[2-(hydroxyamino)-2-oxoethoxy]-6-methoxy-4-quinolyl]oxy]phenyl]-N1-(4-fluorophenyl)cyclopropane-1,1-dicarboxamide;

N1'-[3-fluoro-4-[[7-[3-(hydroxyamino)-3-oxopropoxy]-6-methoxy-4-quinolyl]oxy]phenyl]-N1-(4-fluorophenyl)cyclopropane-1,1-dicarboxamide;

N1'-[3-fluoro-4-[[7-[4-(hydroxyamino)-4-oxobutoxy]-6-methoxy-4-quinolyl]oxy]phenyl]-N1-(4-fluorophenyl)cyclopropane-1,1-dicarboxamide;

N1'-[3-fluoro-4-[[7-[5-(hydroxyamino)-5-oxopentyloxy]-6-methoxy-4-quinolyl]oxy]phenyl]-N1-(4-fluorophenyl)cyclopropane-1,1-dicarboxamide;

N1'-[3-fluoro-4-[[7-[6-(hydroxyamino)-6-oxo hexyloxy]-6-methoxy-4-quinolyl]oxy]phenyl]-N1-(4-fluorophenyl)cyclopropane-1,1-dicarboxamide;

N1'-[3-fluoro-4-[[7-[7-(hydroxyamino)-7-oxoheptyloxy]-6-methoxy-4-quinolyl]oxy]phenyl]-N1-(4-fluorophenyl)cyclopropane-1,1-dicarboxamide;

N1'-[3-fluoro-4-[[6-[[1-[2-(hydroxyamino)-2-oxoethyl]-4-piperidinyl]methoxy]-7-methoxy-4-quinolyl]oxy]phenyl]-N1-(4-fluorophenyl)cyclopropane-1,1-dicarboxamide;

N1'-[3-fluoro-4-[[6-[3-[[2-(hydroxyamino)-2-oxoethyl]amino]propoxy]-7-methoxy-4-quinolyl]oxy]phenyl]-N1-(4-fluorophenyl)cyclopropane-1,1-dicarboxamide;

N1'-[3-fluoro-4-[[6-[3-[[3-(hydroxyamino)-3-oxopropyl]amino]propoxy]-7-methoxy-4-quinolyl]oxy]phenyl]-N1-(4-fluorophenyl)cyclopropane-1,1-dicarboxamide;

N1'-[3-fluoro-4-[[6-[2-(hydroxyamino)-2-oxoethoxy]-7-methoxy-4-quinolyl]oxy]phenyl]-N1-(4-fluorophenyl)cyclopropane-1,1-dicarboxamide;

N1'-[3-fluoro-4-[[6-[3-(hydroxyamino)-3-oxopropoxy]-7-methoxy-4-quinolyl]oxy]phenyl]-N1-(4-fluorophenyl)cyclopropane-1,1-dicarboxamide;

N1'-[3-fluoro-4-[[6-[4-(hydroxyamino)-4-oxobutoxy]-7-methoxy-4-quinolyl]oxy]phenyl]-N1-(4-fluorophenyl)cyclopropane-1,1-dicarboxamide;

N1'-[3-fluoro-4-[[6-[5-(hydroxyamino)-5-oxopentyloxy]-7-methoxy-4-quinolyl]oxy]phenyl]-N1-(4-fluorophenyl)cyclopropane-1,1-dicarboxamide;

N1'-[3-fluoro-4-[[6-[6-(hydroxyamino)-6-oxo hexyloxy]-7-methoxy-4-quinolyl]oxy]phenyl]-N1-(4-fluorophenyl)cyclopropane-1,1-dicarboxamide;

N1'-[3-fluoro-4-[[6-[7-(hydroxyamino)-7-oxoheptyloxy]-7-methoxy-4-quinolyl]oxy]phenyl]-N1-(4-fluorophenyl)cyclopropane-1,1-dicarboxamide;

N1'-(4-fluorophenyl)-N1-[4-[[7-[[1-[2-(hydroxyamino)-2-oxoethyl]-4-piperidinyl]methoxy]-6-methoxy-4-quinolyl]oxy]phenyl]cyclopropane-1,1-dicarboxamide;

N1'-(4-fluorophenyl)-N1-[4-[[7-[3-[[2-(hydroxyamino)-2-oxoethyl]amino]propoxy]-6-methoxy-4-quinolyl]oxy]phenyl]cyclopropane-1,1-dicarboxamide;

N1'-(4-fluorophenyl)-N1-[4-[[7-[3-[[3-(hydroxyamino)-3-oxopropyl]amino]propoxy]-6-methoxy-4-quinolyl]oxy]phenyl]cyclopropane-1,1-dicarboxamide;

N1'-(4-fluorophenyl)-N1-[4-[[7-[2-(hydroxyamino)-2-oxo-ethoxy]-6-methoxy-4-quinolyl]oxy]phenyl]cyclopropane-1,1-dicarboxamide;
N1'-(4-fluorophenyl)-N1-[4-[[7-[3-(hydroxyamino)-3-oxopropoxy]-6-methoxy-4-quinolyl]oxy]phenyl]cyclopropane-1,1-dicarboxamide;
N1'-(4-fluorophenyl)-N1-[4-[[7-[4-(hydroxyamino)-4-oxobutoxy]-6-methoxy-4-quinolyl]oxy]phenyl]cyclopropane-1,1-dicarboxamide;
N1'-(4-fluorophenyl)-N1-[4-[[7-[5-(hydroxyamino)-5-oxopentyloxy]-6-methoxy-4-quinolyl]oxy]phenyl]cyclopropane-1,1-dicarboxamide;
N1'-(4-fluorophenyl)-N1-[4-[[7-[6-(hydroxyamino)-6-oxohexyloxy]-6-methoxy-4-quinolyl]oxy]phenyl]cyclopropane-1,1-dicarboxamide;
N1'-(4-fluorophenyl)-N1-[4-[[7-[7-(hydroxyamino)-7-oxoheptyloxy]-6-methoxy-4-quinolyl]oxy]phenyl]cyclopropane-1,1-dicarboxamide;
N1'-(4-fluorophenyl)-N1-[4-[[6-[[1-[2-(hydroxyamino)-2-oxoethyl]-4-piperidin yl]methoxy]-7-methoxy-4-quinolyl]oxy]phenyl]cyclopropane-1,1-dicarboxamide;
N1'-(4-fluorophenyl)-N1-[4-[[6-[3-[[2-(hydroxyamino)-2-oxoethyl]amino]propoxy]-7-methoxy-4-quinolyl]oxy]phenyl]cyclopropane-1,1-dicarboxamide;
N1'-(4-fluorophenyl)-N1-[4-[[6-[3-[[3-(hydroxyamino)-3-oxopropyl]amino]propoxy]-7-methoxy-4-quinolyl]oxy]phenyl]cyclopropane-1,1-dicarboxamide;
N1'-(4-fluorophenyl)-N1-[4-[[6-[2-(hydroxyamino)-2-oxoethoxy]-7-methoxy-4-quinolyl]oxy]phenyl]cyclopropane-1,1-dicarboxamide;
N1'-(4-fluorophenyl)-N1-[4-[[6-[3-(hydroxyamino)-3-oxopropoxy]-7-methoxy-4-quinolyl]oxy]phenyl]cyclopropane-1,1-dicarboxamide;
N1'-(4-fluorophenyl)-N1-[4-[[6-[4-(hydroxyamino)-4-oxobutoxy]-7-methoxy-4-quinolyl]oxy]phenyl]cyclopropane-1,1-dicarboxamide;
N1'-(4-fluorophenyl)-N1-[4-[[6-[5-(hydroxyamino)-5-oxopentyloxy]-7-methoxy-4-quinolyl]oxy]phenyl]cyclopropane-1,1-dicarboxamide;
N1'-(4-fluorophenyl)-N1-[4-[[6-[6-(hydroxyamino)-6-oxohexyloxy]-7-methoxy-4-quinolyl]oxy]phenyl]cyclopropane-1,1-dicarboxamide;
N1'-(4-fluorophenyl)-N1-[4-[[6-[7-(hydroxyamino)-7-oxoheptyloxy]-7-methoxy-4-quinolyl]oxy]phenyl]cyclopropane-1,1-dicarboxamide.

A quinolyl-containing hydroxamic acid compound is preferably any of the following compounds:
N1'-[3-fluoro-4-[[7-[[1-[2-(hydroxyamino)-2-oxoethyl]-4-piperidinyl]methoxy]-6-methoxy-4-quinolyl]oxy]phenyl]-N1-(4-fluorophenyl)cyclopropane-1,1-dicarboxamide;
N1'-[3-fluoro-4-[[7-[3-[[2-(hydroxyamino)-2-oxoethyl]amino]propoxy]-6-methoxy-4-quinolyl]oxy]phenyl]-N1-(4-fluorophenyl)cyclopropane-1,1-dicarboxamide;
N1'-[3-fluoro-4-[[7-[3-[[3-(hydroxyamino)-3-oxopropyl]amino]propoxy]-6-methoxy-4-quinolyl]oxy]phenyl]-N1-(4-fluorophenyl)cyclopropane-1,1-dicarboxamide;
N1'-[3-fluoro-4-[[7-[2-(hydroxyamino)-2-oxoethoxy]-6-methoxy-4-quinolyl]oxy]phenyl]-N1-(4-fluorophenyl)cyclopropane-1,1-dicarboxamide;
N1'-[3-fluoro-4-[[7-[3-(hydroxyamino)-3-oxopropoxy]-6-methoxy-4-quinolyl]oxy]phenyl]-N1-(4-fluorophenyl)cyclopropane-1,1-dicarboxamide;
N1'-[3-fluoro-4-[[7-[4-(hydroxyamino)-4-oxobutoxy]-6-methoxy-4-quinolyl]oxy]phenyl]-N1-(4-fluorophenyl)cyclopropane-1,1-dicarboxamide;
N1'-[3-fluoro-4-[[7-[5-(hydroxyamino)-5-oxopentyloxy]-6-methoxy-4-quinolyl]oxy]phenyl]-N1-(4-fluorophenyl)cyclopropane-1,1-dicarboxamide;
N1'-[3-fluoro-4-[[7-[6-(hydroxyamino)-6-oxohexyloxy]-6-methoxy-4-quinolyl]oxy]phenyl]-N1-(4-fluorophenyl)cyclopropane-1,1-dicarboxamide;
N1'-[3-fluoro-4-[[7-[7-(hydroxyamino)-7-oxoheptyloxy]-6-methoxy-4-quinolyl ]oxy]phenyl]-N1-(4-fluorophenyl)cyclopropane-1,1-dicarboxamide;
N1'-(4-fluorophenyl)-N1-[4-[[7-[[1-[2-(hydroxyamino)-2-oxoethyl]-4-piperidin yl]methoxy]-6-methoxy-4-quinolyl]oxy]phenyl]cyclopropane-1,1-dicarboxamide;
N1'-(4-fluorophenyl)-N1-[4-[[7-[3-[[2-(hydroxyamino)-2-oxoethyl]amino]propoxy]-6-methoxy-4-quinolyl]oxy]phenyl]cyclopropane-1,1-dicarboxamide;
N1'-(4-fluorophenyl)-N1-[4-[[7-[3-[[3-(hydroxyamino)-3-oxopropyl]amino]propoxy]-6-methoxy-4-quinolyl]oxy]phenyl]cyclopropane-1,1-dicarboxamide;
N1'-(4-fluorophenyl)-N1-[4-[[7-[2-(hydroxyamino)-2-oxoethoxy]-6-methoxy-4-quinolyl]oxy]phenyl]cyclopropane-1,1-dicarboxamide;
N1'-(4-fluorophenyl)-N1-[4-[[7-[3-(hydroxyamino)-3-oxopropoxy]-6-methoxy-4-quinolyl]oxy]phenyl]cyclopropane-1,1-dicarboxamide;
N1'-(4-fluorophenyl)-N1-[4-[[7-[4-(hydroxyamino)-4-oxobutoxy]-6-methoxy-4-quinolyl]oxy]phenyl]cyclopropane-1,1-dicarboxamide;
N1'-(4-fluorophenyl)-N1-[4-[[7-[5-(hydroxyamino)-5-oxopentyloxy]-6-methoxy-4-quinolyl]oxy]phenyl]cyclopropane-1,1-dicarboxamide;
N1'-(4-fluorophenyl)-N1-[4-[[7-[6-(hydroxyamino)-6-oxohexyloxy]-6-methoxy-4-quinolyl]oxy]phenyl]cyclopropane-1,1-dicarboxamide;
N1'-(4-fluorophenyl)-N1-[4-[[7-[7-(hydroxyamino)-7-oxoheptyloxy]-6-methoxy-4-quinolyl]oxy]phenyl]cyclopropane-1,1-dicarboxamide.

A quinolyl-containing hydroxamic acid compound is more preferably any of the following compounds:
N1'-[3-fluoro-4-[[7-[[1-[2-(hydroxyamino)-2-oxoethyl]-4-piperidinyl]methoxy]-6-methoxy-4-quinolyl]oxy]phenyl]-N1-(4-fluorophenyl)cyclopropane-1,1-dicarboxamide;
N1'-[3-fluoro-4-[[7-[4-(hydroxyamino)-4-oxobutoxy]-6-methoxy-4-quinolyl]oxy]phenyl]-N1-(4-fluorophenyl)cyclopropane-1,1-dicarboxamide;
N1'-[3-fluoro-4-[[7-[5-(hydroxyamino)-5-oxopentyloxy]-6-methoxy-4-quinolyl]oxy]phenyl]-N1-(4-fluorophenyl)cyclopropane-1,1-dicarboxamide;
N1'-[3-fluoro-4-[[7-[6-(hydroxyamino)-6-oxohexyloxy]-6-methoxy-4-quinolyl]oxy]phenyl]-N1-(4-fluorophenyl)cyclopropane-1,1-dicarboxamide;
N1'-(4-fluorophenyl)-N1-[4-[[7-[[1-[2-(hydroxyamino)-2-oxoethyl]-4-piperidin yl]methoxy]-6-methoxy-4-quinolyl]oxy]phenyl]cyclopropane-1,1-dicarboxamide;
N1'-(4-fluorophenyl)-N1-[4-[[7-[4-(hydroxyamino)-4-oxobutoxy]-6-methoxy-4-quinolyl]oxy]phenyl]cyclopropane-1,1-dicarboxamide;
N1'-(4-fluorophenyl)-N1-[4-[[7-[5-(hydroxyamino)-5-oxopentyloxy]-6-methoxy-4-quinolyl]oxy]phenyl]cyclopropane-1,1-dicarboxamide;
N1'-(4-fluorophenyl)-N1-[4-[[7-[6-(hydroxyamino)-6-oxohexyloxy]-6-methoxy-4-quinolyl]oxy]phenyl]cyclopropane-1,1-dicarboxamide.

The racemates or enantiomers of any of the above quinolyl-containing hydroxamic acids compound are encompassed in the present invention.

A method of preparing the quinolyl-containing hydroxamic acid compound, consisting of the steps shown in Scheme 1:

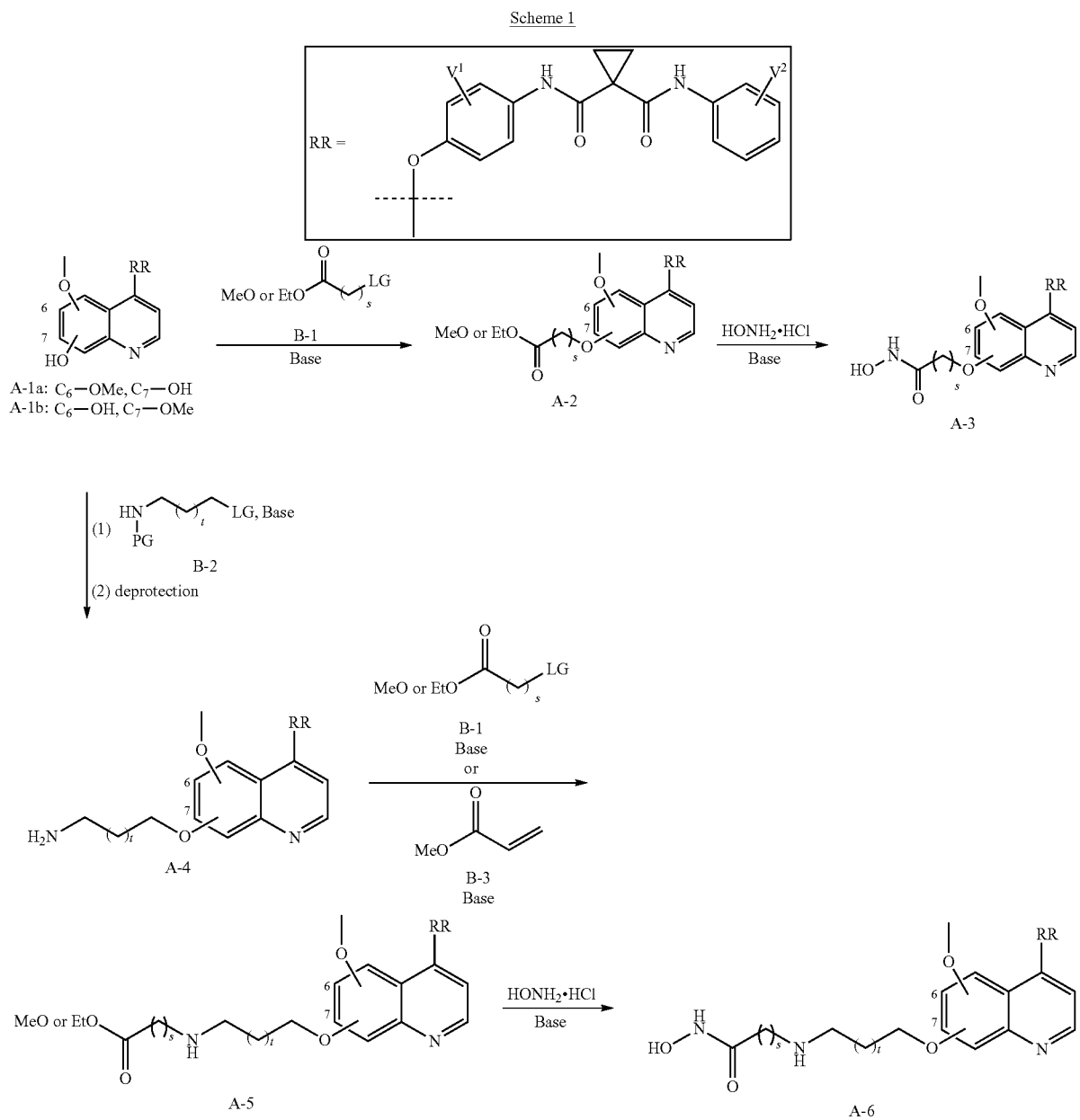

wherein,
t=0-6;
s=1-10;
$V^1$ and $V^2$ each independently represents a hydrogen, halogen, —$OCF_3$, —$CF_3$, —CN, —$NMe_2$, $C_{1-6}$ alkyl, $C_{3-6}$ cycloalkyl, $C_{3-12}$ heteroalicyclyl, $C_{1-6}$ alkoxy, $C_{3-6}$ cycloalkyloxy or $C_{3-12}$ heteroalicyclyloxy group;

LG represents a common leaving group in organic chemistry, and is any one of F, Cl, Br, I, MsO, TsO or TfO;

PG represents a common protecting group in organic chemistry, and is Boc or CBZ.

A method of preparing the quinolyl-containing hydroxamic acid compound, consisting of the steps shown in Scheme 2:

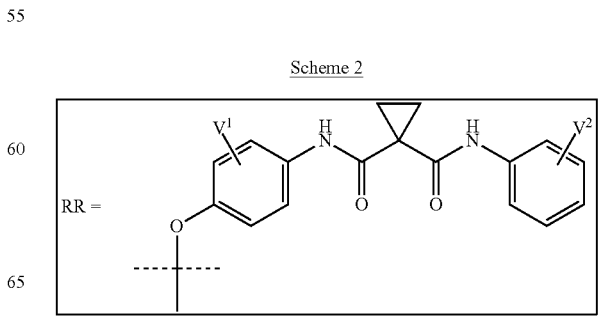

-continued

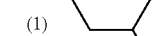
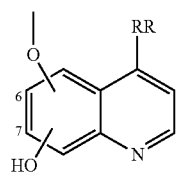

A-1a: C$_6$—OMe, C$_7$—OH
A-1b: C$_6$—OH, C$_7$—OMe

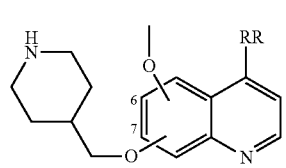
A-7

-continued

A-8

$V^1$ and $V^2$ each independently represents a hydrogen, halogen, —OCF$_3$, —CF$_3$, —CN, —NMe$_2$, C$_{1-6}$ alkyl, C$_{3-6}$ cycloalkyl, C$_{3-12}$ heteroalicyclyl, C$_{1-6}$ alkoxy, C$_{3-6}$ cycloalkyloxy or C$_{3-12}$ heteroalicyclyloxy group;

s=1-10.

A method of preparing the quinolyl-containing hydroxamic acid compound, consisting of the steps shown in Scheme 3:

Scheme 3

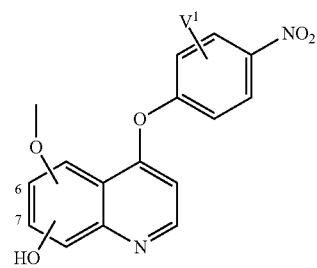

A-9a: C$_6$—OMe, C$_7$—OH
A-9b: C$_6$—OH, C$_7$—OMe

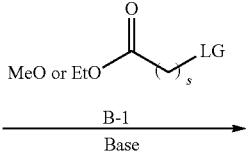

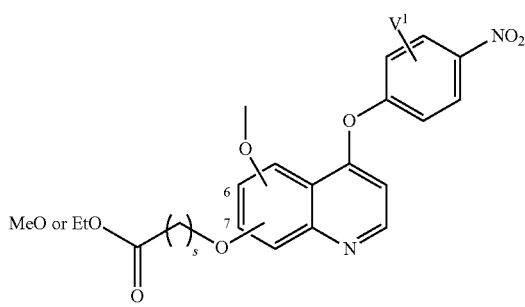

A-10

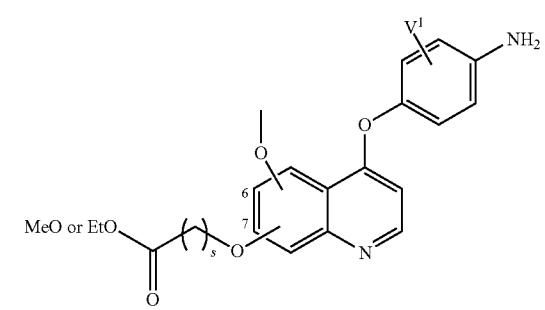

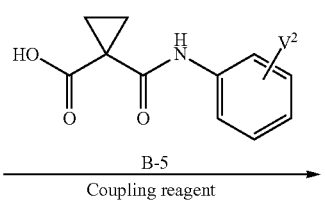

A-11

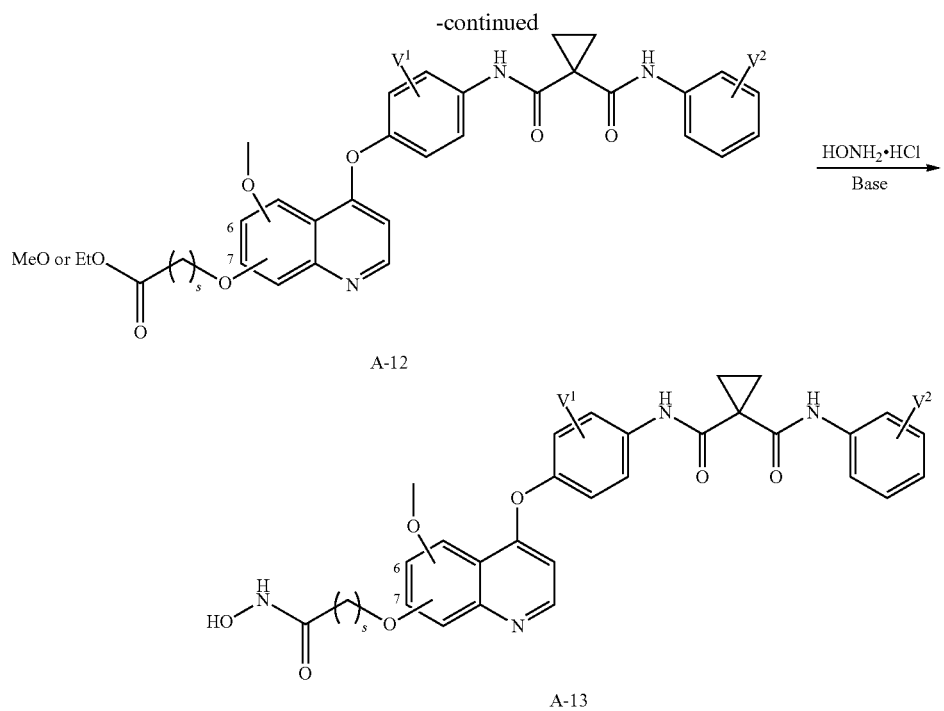

A-12

A-13

$V^1$ and $V^2$ each independently represents a hydrogen, halogen, —$OCF_3$, —$CF_3$, —CN, —$NMe_2$, $C_{1-6}$ alkyl, $C_{3-6}$ cycloalkyl, $C_{3-12}$ heteroalicyclyl, $C_{1-6}$ alkoxy, $C_{3-6}$ cycloalkyloxy or $C_{3-12}$ heteroalicyclyloxy group;

s=1-10.

The present application is directed to the use of a pharmaceutical composition comprising the quinolyl-containing hydroxamic acid compound for treatment of diseases caused by abnormal activity of protein kinase and/or histone deacetylase.

In the use of the pharmaceutical composition comprising the compound of the present invention, the protein kinase is ALK, AXL, BTK, CDK11, c-Met, KDR, VEGFR2, RET, PDGFR-α, PDGFR-β, c-KIT, Flt3, MEK1, MEK2, CSF1R, EPHA2, MKNK2, TIE2, TRKA, SRC, PLK4, RON, EGF1R, HER2, HER3, HER4, PDGFR-α, c-fms, FLT1, Src, Frk, Btk, CsK, Abl, Fes, Fps, Fak, AcK, Yes, Fyn, Lyn, Lck, Hck, Fgr, Yrk, PDK1, TAK1, Tie-1, YSK4, TRK B, TRK C, SLK, PKN2, MST1R, MAP4K or DDR2.

Preferably, in the use of the pharmaceutical composition comprising the compound of the present invention, the protein kinase is ALK, AXL, BTK, CDK11, c-Met, KDR, VEGFR2, RET, PDGFR-α, PDGFR-β, c-KIT, Flt3, MEK1, MEK2, CSF1R, EPHA2, MKNK2, TIE2, TRKA, SRC or PLK4.

In the use the pharmaceutical composition comprising the compound of the present invention, the histone deacetylase is HDAC2, HDAC6, HDAC1, HDAC3, HDAC4, HDAC5, HDAC7, HDAC8, HDAC9, HDAC10 or HDAC11.

Preferably, in the use of the pharmaceutical composition comprising the compound of the present invention, the histone deacetylase is HDAC2 and/or HDAC6.

In the use of the pharmaceutical composition comprising the compound of the present invention, the disease is psoriasis, cirrhosis, diabetes, disease involving angiogenesis, eye disease, immune system disease, cardiovascular disease, epilepsy, neurodegenerative disease, Alzheimer's disease, Huntington's disease or Parkinson's disease.

In the use of the pharmaceutical composition comprising the compound of the present invention, the disease is tumor, including solid tumors and liquid tumors.

In the use of the pharmaceutical composition comprising the compound of the present invention, the tumor particularly comprises one of or any combination of lung cancer, bone cancer, pancreatic cancer, skin cancer, head and neck cancer, skin or intraocular melanoma, uterine cancer, ovarian cancer, rectal cancer, anal area cancer, stomach cancer, colon cancer, breast cancer, fallopian tube cancer, endometrial cancer, cervical cancer, vaginal cancer, vulva cancer, Hodgkin's disease, esophagus, small intestine, endocrine system cancer, thyroid cancer, parathyroid carcinoma, soft tissue sarcoma, urethral cancer, penile cancer, prostate cancer, chronic or acute leukemia, bladder cancer, cancer of the kidney or ureter, renal carcinoma, central nervous central system (CNS) excrescence, spinal axis tumor, pituitary adenoma, gastrointestinal stromal tumor, colorectal cancer, non-small cell lung cancer, small cell lung cancer, mastocytosis, glioma, sarcoma, and lymphoma.

The present application provides a pharmaceutical composition for treating diseases caused by abnormal activity of protein kinase and/or histone deacetylase, comprising any one of or any combination of the compounds of the present application mentioned above or the pharmaceutically acceptable salts, solvates, or prodrugs thereof, or the racemates, enantiomers of any one of or any combination of the compounds or the pharmaceutically acceptable salts, solvates, or prodrugs thereof The pharmaceutical composition of the present invention may further comprise one or more pharmaceutically acceptable carriers.

The dosage form of any of the pharmaceutical compositions of the present invention is as follows:

i. oral form; (2) injection form; (3) rectal suppository form; (4) nasal inhalation form; (5) eye drops form; and (6) skin patch form.

A series of testing has proved that the quinolyl-containing hydroxamic acid compound of the present invention has the following beneficial effects: (1) it can be seen from the screening experiments of inhibiting the kinase and/or histone deacetylase activity that the compounds of the invention exert a strong inhibitory effect on a series of protein kinases and their mutants and histone deacetylase; (2) it can be seen from the anti-tumor experiments in animal models that such quinolyl-containing hydroxamic acid compound can significantly inhibit tumor growth and have no significant toxicity; (3) the compounds of the present invention may be used in combination with other antitumor drugs so as to show a synergistic or additive effect; (4) the compounds of the present invention may be used in combination with other tumor therapies, such as radiation therapy, interventional therapy. Thus, the quinolyl-containing hydroxamic acid compound of the present invention can be used as an effective drug for the treatment of diseases caused by abnormal activity of protein kinase and/or histone deacetylase.

In the use of the compounds of the invention for the treatment of diseases caused by abnormal activity of protein kinase and/or histone deacetylase, the renal carcinoma is adrenal carcinoma, renal cell carcinoma or renal pelvic carcinoma; and the glioma is brain stem glioma, neuroendocrine glial tumor, neurospongioma.

In the use of the compounds of the invention for the treatment of diseases caused by abnormal activity of protein kinase and/or histone deacetylase, in addition to tumor, the diseases can be psoriasis, cirrhosis, diabetes, diseases involving angiogenesis, diseases involving restenosis, eye diseases such as AMD, rheumatoid arthritis and other inflammations, immune system diseases such as autoimmune diseases (e.g., AIDS and the like), cardiovascular diseases such as atherosclerosis, kidney diseases, epilepsy, neurodegenerative diseases, such as Alzheimer's disease, Huntington's disease, Parkinson's disease and the like.

The pharmaceutical composition comprising the compound of the invention is used for the treatment of diseases caused by abnormal activity of protein kinases and/or histone deacetylase of a mammal, such as a human patient.

The compound of the invention (including racemates, enantiomers and other stereoisomers) or the pharmaceutically acceptable salts, hydrates, solvates or prodrugs thereof, in combination with suitable pharmaceutically acceptable carriers and pharmaceutically commonly used adjuvants are prepared as a pharmaceutical composition conducive to the administration through a formulation process.

The routes of administration of the pharmaceutical composition comprising the compound of the invention may be: (1) oral: for example, tablets, capsules, etc.; (2) injection: for example, intravenous injection, subcutaneous injection, intramuscular injection, eye injection, intraperitoneal injection, etc.; (3) anal plug: for example, suppositories, gels and the like; (4) nasal inhalation: for example, sprays, aerosols, etc.; (5) eye drops; (6) a skin patch. A drug delivery system may also be used, for example, liposome or sustained-release technology, wherein the preferred methods are oral administration and injection, more preferably oral administration.

The various dosage forms of the pharmaceutical compositions comprising the compound of the invention can be prepared by the commonly used method in pharmaceutical industry, for example, mixing, dissolving, granulating, grinding, emulsification, capsules, sugar-coated, freeze drying, freezing spray and the like.

The compound of the invention is present in an amount ranging from 0.001% to 100% in the aforementioned pharmaceutical compositions. The pharmaceutical composition is administered to a mammal, including a human, in an effective daily dose of 0.1 mg to 500 mg per kilogram body weight, preferably 1 mg to 100 mg per kilogram body weight. In this range of effective doses, the compound of the invention exhibits its pharmacological action by inhibiting protein kinase activity and/or histone deacetylase activity and treatment of diseases caused by abnormal protein kinase activity and/or histone deacetylase activity (such as, cancers).

The administration frequency of the compound of the invention varies with the compound or its pharmaceutical composition used, and the disease. The pharmaceutical composition is usually administered 1-6 times daily, and the preferred administration frequency is 1-3 times daily.

The packaging and preservation of the pharmaceutical composition of the present invention are similar to those of general western medicines. For example, the drug in solid dosage form can be contained directly in a glass, plastic, paper or metal bottle in which a desiccant and the like are preferably added to maintain the quality of the drug; the drug in liquid dosage form can be contained usually in a glass, plastic or metal bottle or a tube; and the drug in aerosol dosage form can be contained in a pressure-proof metal or plastic container equipped with a pressure-regulating valve.

DEFINITIONS

The definitions of the terms involved in the present invention are as follows. The variable groups, such as $R^a$, $R^b$, m, are only applicable in the present section (i.e. the section of "Definitions").

In accordance with the common knowledge of a person skilled in the art, the chemical reactions need to be carried out in a solvent in most cases. The commonly used solvents for preparing the compound of the present invention include but are not limited to water, methanol, ethanol, isopropanol, n-propanol, n-butanol, isobutanol, t-butanol, 2-methoxyethanol, 2,2,2-trifluoroethanol, dichloromethane, 1,2-dichloroethane, chloroform, THF, dioxane, DME, ethyl acetate, diethyl ether, methyl tert-butyl ether, hexane, cyclohexane, toluene, acetonitrile, DMF, DMSO, or a mixture of two or more of these solvents and the like.

In certain situations, the occurrence of chemical reactions needs to be mediated by an acid or base. The bases commonly used to prepare the compound of the present application include but are not limited to $Et_3N$, $Me_3N$, $i-Pr_2NEt$, pyridine, DBU, DABCO, tetramethyl guanidine, NaOH, KOH, $Cs_2CO_3$, $Na_2CO_3$, $K_2CO_3$, $NaHCO_3$, KF, CsF, $K_3PO_4$, $K_2HPO_4$, $KH_2PO_4$, NaH, n-BuLi, s-BuLi, t-BuLi, $NaN(SiMe_3)_2$, $LiN(SiMe_3)_2$, $KN(SiMe_3)_2$ or the mixture of two or more of these bases. The acids commonly used to prepare the compound of the present application include but are not limited to $HCO_2H$, AcOH, TFA (trifluoroacetic acid), HCl (hydrochloric acid), $H_2SO_4$, $HNO_3$, $H_3PO_4$, p-TsOH, $PhSO_3H$, CSA, MsOH and the like or Lewis acid such as $ZnCl_2$, $AlCl_3$, $BF_3.OEt_2$, and the like.

In certain situations, the occurrence of chemical reactions needs a coupling reagent. The coupling reagents commonly used to prepare the compound of the present application include but are not limited to DCC, EDC, HATU, TBTU, PyBOP, HCTU, BOP, DIC, HOBt, HOAt, CDI, DEPBT and the like.

Some steps of preparation of the compound of the invention require reduction and a reducing reagent, the reducing reagents include but not limited to $H_2$+Pd/C, $H_2$+Pd(OH)$_2$, $H_2$+PtO$_2$, $H_2$+Raney Ni, $H_2NNH_2$+Raney Ni, Mg+MeOH, Fe+AcOH, Fe+HCl, Zn+AcOH, Zn+HCl, Zn+NH$_4$OAc, SnCl$_2$, LiAlH$_4$, NaBH$_4$, NaBH$_3$(CN), NaB(OAc)$_3$H, BH$_3$ and the like.

Some steps of preparation of the compound of the invention require deprotection. When deprotecting the Boc group, the commonly used deprotection reagents include but not limited to HCl, TFA, H$_2$SO$_4$ and the like. When deprotecting the CBZ group, the commonly used deprotection reagents include but not limited to H$_2$+Pd/C, H$_2$+Pd(OH)$_2$, H$_2$+Pd/C+HCl and the like.

The reaction for preparing the compound of the present invention is usually carried out at room temperature, but sometimes needs to be cooled to −78° C. or heated to 200° C. The reaction is usually carried out in the aforementioned solvents, at above-mentioned temperatures and with conventional stirring, but sometimes in a microwave oven. When the bases, reagents, or catalysts used are sensitive to water or oxygen, the reaction must be carried out under anhydrous and oxygen-free conditions. In such a situation, a protic solvent cannot be used.

The term "pharmaceutically acceptable salts" refers to the salts formed by a chemical reaction of the compound of the present invention with an inorganic acid, an organic acid, an inorganic base or an organic base, such salts retaining the biological activity and effectiveness of the compound of the present invention. The inorganic or organic acid may be hydrochloric acid, hydrobromic acid, hydroiodic acid, sulfuric acid, nitric acid, carbonic acid, phosphoric acid, perchloric acid, acetic acid, citric acid, oxalic acid, lactic acid, malic acid, salicylic acid, tartaric acid, methanesulfonic acid, ethanesulfonic acid, benzenesulfonic acid, substituted benzenesulfonic acid (e.g., p-toluenesulfonic acid), isonicotinic acid, oleic acid, tannic acid, pantothenic acid, ascorbic acid, succinic acid, maleic acid, gentisic acid, fumaric acid, gluconic acid, uronic acid, glucaric acid or sucrose acid, formic acid, benzoic acid, glutamic acid, pamoic acid, sorbic acid and the like; the inorganic or organic bases may be sodium hydroxide, potassium hydroxide, lithium hydroxide, ferric hydroxide, calcium hydroxide, aluminum hydroxide, barium hydroxide, magnesium hydroxide, zinc hydroxide, ammonia, hydroxide organic quaternary ammonium salt, sodium carbonate, potassium carbonate, lithium carbonate, calcium carbonate, barium carbonate, magnesium carbonate, carbonate organic quaternary ammonium salt, sodium bicarbonate, potassium bicarbonate, lithium bicarbonate, calcium bicarbonate, barium bicarbonate, magnesium bicarbonate, organic quaternary ammonium bicarbonates.

The term "solvates" as used herein means the stable substances formed from the compound of the present invention and commonly used solvents in chemistry through a covalent bond, hydrogen bond, ionic bond, van der Waals force, complexation, inclusion, etc. The solvents may be methanol, ethanol, propanol, butanol, ethylene glycol, propylene glycol, polyethylene glycol, acetone, acetonitrile, diethyl ether, methyl tert-butyl ether, etc.

The term "hydrate" refers to a solvate wherein the solvent is water.

The term "prodrug" refers to the compound of the present invention is converted into another compound, which can be converted back to the compound of the present invention in vivo after administered to a mammal, by chemical reaction or physical methods. The "prodrug" approach is usually used to overcome adverse or poor physicochemical properties or druggability of the drug compound itself.

The term "racemates, enantiomers and other stereoisomers" refers to the compounds having the same molecular formula and molecular weight but with different manner of bonding and the spatial arrangement of atoms, and the compounds are thus called isomers or stereoisomers. When these stereoisomers are in a mirror image relationship to each other, i.e. they look similar, but cannot completely overlap, just like the left hand and right hand, they are called enantiomers. The absolute configuration of an enantiomer is typically expressed as (R)- and (S)- or R- and S-. The specific rules for determining the absolute configuration of enantiomers are described in Chapter 4 of "Advanced Organic Chemistry", 4$^{th}$ edition (by J. March, John Wiley and Sons, New York, 1992). (R)- and (S)-enantiomers have opposite effect on rotation of the polarized light, i.e. levorotation and dextrorotation. When a (R)-enantiomer and a (S)-enantiomer are mixed or present in a ratio of 1:1, the mixture does not have an effect on rotation of the polarized light, and is referred to as the racemate.

The compound of the present invention may also be present in the form of tautomers, rotamers, cis-trans isomers, etc. These concepts can be found and understood in "Advanced Organic Chemistry," 4$^{th}$ edition edited by J. March. As long as these isomers have the same/similar effect of inhibition of protein kinase activity as the compounds of the present invention, they are also covered in the present invention.

After administered to a mammal (such as a human being), the compounds of the present invention are likely to be metabolized in vivo into various metabolites by different enzymes according to the common knowledge in the art. As long as these metabolites have similar effect of inhibition of protein kinase activity of the compounds of the present invention, they are also covered in the present invention.

The term "pharmaceutical composition" refers to a mixture of one or more of the compounds of the present invention, pharmaceutically acceptable salts, solvates, hydrates or prodrugs thereof and other chemical components (such as a pharmaceutically acceptable carrier). The pharmaceutical composition is used to facilitate the process of the administration of compounds of the present invention to animals. In addition to the pharmaceutically acceptable carriers, the pharmaceutical compositions may also include pharmaceutically commonly used adjuvants, such as anti-bacterial agent, anti-fungal agent, antimicrobial agent, preservative, color matching agent, solubilizer, thickener, surfactant, complexing agent, protein, amino acid, fat, carbohydrate, vitamin, mineral, trace element, sweetener, pigment, flavor or a combination thereof.

The term "pharmaceutically acceptable carrier" refers to a non-active ingredient in the pharmaceutical composition, which can be: calcium carbonate, calcium phosphate, various carbohydrates (such as lactose, mannitol, etc.), starch, cyclodextrin, magnesium stearate, cellulose, magnesium carbonate, acrylic polymer, methacrylic polymer, gel, water, polyethylene glycol, propylene glycol, ethylene glycol, castor oil, hydrogenated castor oil, polyethoxylated hydrogenated castor oil, sesame oil, corn oil, peanut oil and the like.

The term "alkyl" refers to a straight-chain or branched-chain saturated hydrocarbon group having the specified number of carbon atoms. For example, $C_{1-12}$ alkyl means a straight-chain or branched chain group containing carbon atoms ranging from 1 to 12. $C_0$ alkyl represents a covalent single bond. The alkyl groups of the present invention include, but are not limited to methyl, ethyl, propyl, butyl, isopropyl, neopentyl, 2-methyl-1-hexyl, etc. The alkyl of the present invention sometimes also refers to alkylene, i.e. the group formed from the alkyl by losing one hydrogen atom. One or all of the hydrogen atoms of alkyl or alkylene may be substituted with the following groups: cycloalkyl, aryl, heteroaryl, heteroalicyclyl, halogen, amino, hydroxyl, cyano, nitro, carboxyl, mercapto, oxo, alkoxy, aryloxy, alkyl mercapto, aryl mercapto, carbonyl, thiocarbonyl, C-amido, N-amido, O-aminocarbonyloxy, N-aminocarbonyloxy, O-aminothiocarbonyloxy, N-aminothiocarbonyloxy, C-ester, O-ester, and —NR$^a$R$^b$, wherein R$^a$ and R$^b$ are independently selected from hydrogen, alkyl, cycloalkyl, aryl, acetyl, carbonyl, sulfonyl, trifluoromethylsulfonyl, and R$^a$ and R$^b$, together with nitrogen atom they are attached to can form a 5- or 6-membered heteroalicyclyl ring.

The term "cycloalkyl" or "cycloalkane" refers to a monocyclic, bicyclic or polycyclic hydrocarbon group having a specified number of carbon atoms. In the case of bicyclic and polycyclic ring, they can combine in the fused form (two rings or more rings share two adjacent carbon atoms) or in the spiro ring form (two rings or more rings share one carbon atom). For example, C$_{1-12}$ cycloalkyl means a monocyclic, bicyclic or polycyclic hydrocarbon group containing carbon atoms ranging from 1 to 12. C$_0$ cycloalkyl represents a covalent single bond. The cycloalkyl may contain an unsaturated double bond or triple bond, but not have a completely conjugated pi-electron system (π electron system). The cycloalkyl of the present invention sometimes refers to a cycloalkylene, i.e. the group formed from the cycloalkyl by losing one hydrogen atom. The cycloalkyl groups of the present invention include, but are not limited to: cyclopropyl, cyclobutyl, cyclohexyl, cyclopentenyl, cycloheptatrienyl, adamantyl, etc. (examples showed in Table 1):

TABLE 1

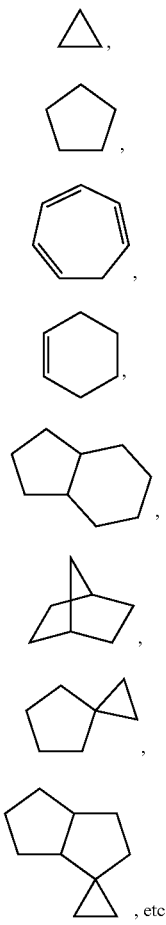

One or all of the hydrogen atoms of cycloalkyl or cycloalkane may be substituted with the following groups: alkyl, aryl, heteroaryl, heteroalicyclyl, halogen, amino, hydroxyl, cyano, nitro, carboxyl, mercapto, oxo, alkoxy, aryloxy, alkyl mercapto, aryl mercapto, carbonyl, thiocarbonyl, C-amido, N-amido, O-aminocarbonyloxy, N-aminocarbonyloxy, O-aminothiocarbonyl, N-aminothiocarbonyloxy, C-ester, O-ester, and —NR$^a$R$^b$, wherein R$^a$ and R$^b$ are independently selected from: hydrogen, alkyl, cycloalkyl, aryl, acetyl, carbonyl, sulfonyl, trifluoromethylsulfonyl, and R$^a$ and R$^b$, together with nitrogen atom they are attached to can form a 5- or 6-membered heteroalicyclyl ring.

The term "halogen" refers to fluorine, chlorine, bromine or iodine.

The term "alkoxy" refers that an alkyl group having the specified number of carbon atoms connects with other group via an oxygen atom. The alkoxy groups of the present invention include, but are not limited to methoxy, ethoxy, propoxy, butoxy, cyclopentoxy, cyclohexyloxy, isopropoxy, neopentoxy, 2-methyl-1-hexyloxy.

The term "cycloalkyloxy" refers that a cycloalkyl group having the specified number of carbon atoms connects with other group via an oxygen atom. The cycloalkyloxy groups of the present invention include, but are not limited to cyclopropoxy, cyclopentoxy, cyclohexyloxy.

The term "aryl" refers to a monocyclic, bicyclic or polycyclic group composed of 6 to 12 carbon atoms, wherein at least one ring has a completely conjugated pi-electron system and conforms to the n+2 rule, namely the group has aromaticity, but the entire group does not have to be completely conjugated. The aryl group may be present in the form of an arylene group, i.e. there are two or more connection sites with other groups in the aryl structure. The aryl groups of the present invention include, but are not limited to phenyl, naphthyl, indenyl, indanyl, tetrahydronaphthalenyl, etc. One or all of the hydrogen atoms of aryl group may be substituted with the following groups: alkyl, cycloalkyl, heteroaryl, heteroalicyclyl, halogen, amino, hydroxyl, cyano, nitro, carboxyl, mercapto, oxo, alkoxy, aryloxy, alkyl mercapto, aryl mercapto, carbonyl, thiocarbonyl, C-amido, N-amido, O-aminocarbonyloxy, N-aminocarbonyloxy, O-aminothiocarbonyloxy, N-aminothiocarbonyloxy, C-ester, O-ester, and —NR$^a$R$^b$, wherein R$^a$ and R$^b$ are independently selected from: hydrogen, alkyl, cycloalkyl, aryl, acetyl, carbonyl, sulfonyl, trifluoromethylsulfonyl etc., and R$^a$ and R$^b$, together with nitrogen atom they are attached to can form a 5- or 6-membered heteroalicyclyl ring.

The term "heteroaryl" refers to a monocyclic, bicyclic or polycyclic group consisting of 5-12 ring atoms other than a hydrogen atom, wherein at least one atom is O, N or S(=O)$_m$ (in which m=0-2), and wherein at least one ring has a completely conjugated pi-electron system and conforms to the n+2 rule, namely the group has aromaticity, but the entire group does not have to be completely conjugated. For example, C$_5$ heteroaryl refers to an aromatic ring group constituted by 5 ring atoms, wherein at least one ring atom is selected from O, N or S(=O)$_m$ (in which m=0-2). The heteroaryl group may be present in the form of heteroarylene, i.e. there are two or more connection sites with other groups in the heteroaryl structure. The heteroaryl groups of the present invention include, but are not limited to pyridinyl, pyridonyl, tetrahydropyridonyl, pyrimidinyl, pyrazinyl, pyridazinyl, imidazolyl, thiazolyl, thiophenyl, furanyl, indolyl, azaindolyl, benzimidazolyl, indolinyl, indolinonyl, quinolinyl, etc. (examples shown in Table 2):

TABLE 2
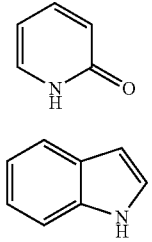
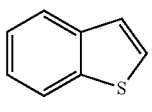
TABLE 2-continued
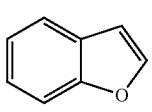
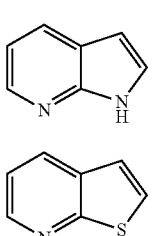
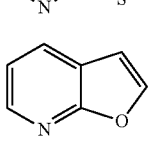
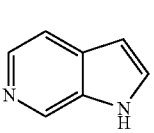
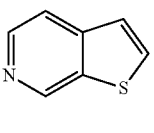

TABLE 2-continued

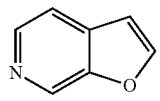
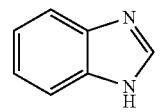
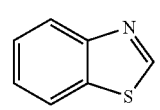
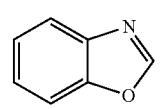
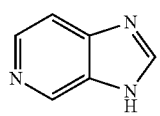
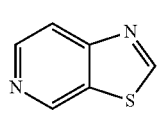
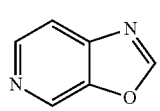
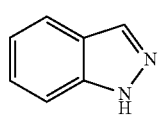
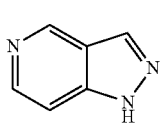
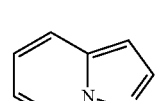
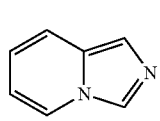
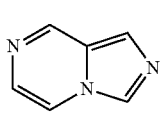
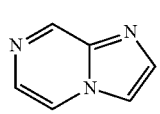
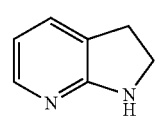

TABLE 2-continued

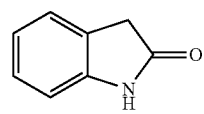
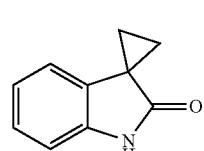
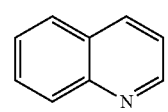
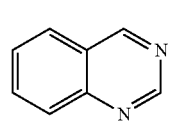
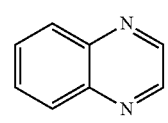
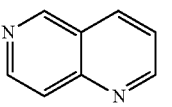
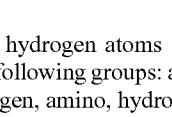

etc

One or all of the hydrogen atoms of heteroaryl may be substituted with the following groups: alkyl, cycloalkyl, aryl, heteroalicyclyl, halogen, amino, hydroxyl, cyano, nitro, carboxyl, mercapto, oxo, alkoxy, aryloxy, alkyl mercapto, aryl mercapto, carbonyl, thiocarbonyl, C-amido, N-amido, O-aminocarbonyloxy, N-aminocarbonyloxy, O-aminothiocarbonyloxy, N-aminothiocarbonyloxy, C-ester, O-ester, and —$NR^aR^b$, wherein $R^a$ and $R^b$ are independently selected from: hydrogen, alkyl, cycloalkyl, aryl, acetyl, carbonyl, sulfonyl, trifluoromethylsulfonyl etc., and $R^a$ and $R^b$, together with nitrogen atom they are attached to can form a 5- or 6-membered heteroalicyclyl ring.

The term "heteroalicyclyl" or "heteroalicycle" refers to a monocyclic, bicyclic or polycyclic group or alkane composed of 3-12 ring atoms other than a hydrogen atom, wherein at least one atom is O, N or $S(=O)_m$ (in which m=0-2). For example, $C_6$ heteroalicyclyl refers to a monocyclic group constituted by 6 ring atoms, wherein at least one ring atom is selected from O, N or $S(=O)_m$ (in which m=0-2). In addition to single bonds, such ring may further contain double or triple bonds, but these double or triple bonds do not form a completely conjugated aromatic structure. These monocyclic, bicyclic or polycyclic heteroalicyclyl can be present in the form of a fused ring, a bridged ring or a spiro ring. The heteroalicyclyl group of the present invention sometimes refers to heteroalicyclylene group, i.e. the group formed from heteroalicyclyl group after losing a hydrogen atom. The heteroalicyclyl groups or heteroalicycles of the present invention include, but not limited to piperidinyl, morpholinyl, piperazinyl, pyrrolidinyl, indolinyl, tetrahydropyridinyl, tetrahydrofuranyl, tropine alcohol (examples shown in Table 3):

TABLE 3

[Structures of saturated/unsaturated heterocyclic rings including: azetidine, oxetane, tetrahydrofuran, pyrrolidine, tetrahydrothiophene, tetrahydrothiophene S-oxide, tetrahydrothiophene S,S-dioxide (sulfolane), piperidine, tetrahydropyran, tetrahydrothiopyran, morpholine, 1,4-dioxane, 1,4-thioxane]

TABLE 3-continued

[Structures continued: piperazine, thiomorpholine, 1,4-diazepane, 1,4-oxazepane, 1,2,3,6-tetrahydropyridine, 3,4-dihydro-2H-pyran, 2H-pyran, 2-azaspiro[4.4]nonane, 2-oxa-7-azaspiro[4.4]nonane, 2-azabicyclo[2.2.1]heptane, 2-azabicyclo[2.2.2]octane, 1-azaadamantane]

One or all of the hydrogen atoms of heteroalicyclyl or heteroalicycle may be substituted with the following groups: alkyl, cycloalkyl, aryl, heteroaryl, heteroalicyclyl, halogen, amino, hydroxyl, cyano, nitro, carboxyl, mercapto, oxo, alkoxy, aryloxy, alkyl mercapto, aryl mercapto, carbonyl, thiocarbonyl, C-amido, N-amido, O-aminocarbonyloxy, N-aminocarbonyloxy, O-aminothiocarbonyloxy, N-aminothiocarbonyloxy, C-ester, O-ester, and —NR$^a$R$^b$, wherein R$^a$ and R$^b$ are independently selected from: hydrogen, alkyl, cycloalkyl, aryl, acetyl, carbonyl, sulfonyl, trifluoromethylsulfonyl, etc., and R$^a$ and R$^b$, together with nitrogen atom they are attached to can form a 5- or 6-membered heteroalicyclyl ring.

The term "aryloxy" refers to an aryl group connecting with other group via an oxygen atom. The aryloxy groups of the present invention include, but are not limited to phenoxy, naphthoxy, etc.

The term "heteroaryloxy" refers to a heteroaryl group connecting with other group via an oxygen atom. The heteroaryloxy groups of the present invention include, but are not limited to 4-pyridyloxy, 2-thienyloxy, etc.

The term "amino" refers to H$_2$N— or H$_2$N—, in which a hydrogen atom may be substituted, i.e. R$^a$HN— and R$^a$R$^b$N—.

The term "oxo" refers to =O, namely, an oxygen atom connecting with a carbon atom or a hetero atom selected from the group including N, S, or P via a double bond. Examples of the groups substituted with oxo include, but are not limited to the examples shown in Table 4:

"hydroxyl" refers to —OH; "nitro" refers to —NO$_2$;
"carboxy" refers to —CO$_2$H; "mercapto" refers to —SH;
"alkyl mercapto" refers to alkyl-S—; "aryl mercapto" refers to aryl-S—;
"carbonyl" refers to —C(=O)—; "thiocarbonyl" refers to —C(=S)—;
"C-amido" refers to —C(=O)NR$^a$R$^b$; "N-amido" refers to C(=O)NR$^a$—;
"O-aminocarbonyloxy" refers to —O—C(=O)NR$^a$R$^b$;
"N-aminocarbonyloxy" refers to O—C(=O)NR$^a$—;
"O-aminothiocarbonyloxy" refers to —O—C(=S)NR$^a$R$^b$;
"N-aminothiocarbonyloxy" refers to O—C(=S)NR$^a$—;
"C-ester" refers to —C(=O)OR$^a$; "N-ester" refers to C(=O)O—;
"acetyl" refers to CH$_3$C(=O)—; "sulfonyl" refers to —SO$_2$R$^a$;
"trifluoromethylsulfonyl" refers to CF$_3$SO$_2$—.

EXAMPLES

Figure 1:
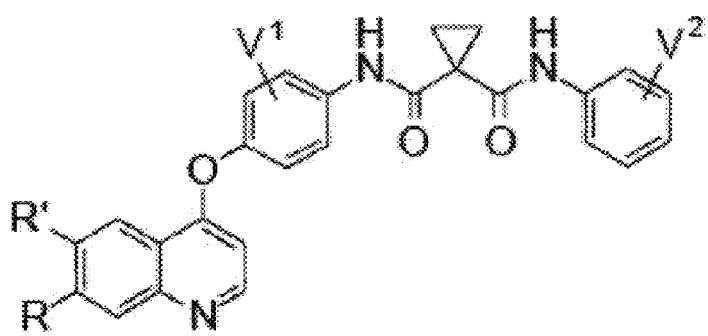
FIG. 1 is the molecular structure of the compound of the present invention.

The present invention will be described in further details in combination with the following specific examples, in order that the public can further understand the compound of the present invention and advantageous effect thereof. However, the examples are not intended to limit the embodiments of the present invention.

The English abbreviation present in the embodiment and the corresponding Chinese meaning are presented below. In case that an abbreviation not listed herein is present in the examples, it represents the generally accepted meaning.

DMSO: dimethyl sulfoxide; DMSO-$d_6$: dimethyl sulfoxide-$d_6$;

TMS: tetramethylsilane; DCM: dichloromethane;

$CDCl_3$: deuterated chloroform; $CD_3OD$: Deuterated methanol;

DME: 1,2-dimethoxyethane; THF: tetrahydrofuran;

EtOAc: ethyl acetate; MeOH: methanol;

HCl: hydrogen chloride or hydrochloric acid;

aq.: aqueous solution;

TLC: thin-layer chromatography;

LC-MS: liquid chromatography-mass spectrometry g: gram; mg: milligram;

mmol: millimole; μM: micromole;

pM: picomole; μL: microliter;

nM: nanomole;

[M+H]: molecular ion peak in mass spectrum;

N: equivalent concentration; m/z: mass-to-charge ratio;

δ: chemical shift; DMAP: 4-dimethylaminopyridine;

DIPEA: diisopropylethyl amine;

HATU: 2-(7-azobenzotriazole)-N,N,N',N'-tetramethylammonium hexafluorophosphate.

General Experimental Conditions:

The spectrums of $^1H$ NMR and $^{13}C$ NMR are obtained by Varian NOVA 500NB, Varian 400 MHz or Bruker 400 MHz instruments (deuterated DMSO, deuterated chloroform and deuterated methanol, etc. as solvent, and TMS as internal standard). Mass spectra are obtained by liquid chromatography-mass spectrometry (ESI or APCI ion source ZQ4000, Waters, USA). UV spectra are measured by Hitachi UV-3010 UV spectrophotometer. IR spectra are measured by NICOLET6700 infrared spectroscopy (KBr tablet). High performance liquid chromatography uses Waters 2695 ZORBAX HPLC (Bx-$C_8$ 5μ 150×4.6 mm column). The melting point is measured by electrothermal digital melting point apparatus IA9100 and are uncorrected.

Starting materials, reagents and solvents were purchased from the following suppliers: Beta-Pharma, Shanghai; Shanghai PI Chemicals; AndaChem, Taiyuan; Shanghai FWD Chemicals; Sigma-Aldrich, Milwaukee, Wis., USA; Acros, Morris Plains, N.J., USA; Frontier Scientific, Logan, Utah, USA; Alfa Aesar, Ward Hill, Mass., USA, etc. or synthesized according to the methods reported in the documents. Unless otherwise indicated, the solvent from supplier was often directly used without drying, or after drying by molecular sieve.

The methods for preparation of various intermediates required for preparing the compounds of the present invention are described as follows, which include Intermediate A, Intermediate B, Intermediate C, Intermediate D, Intermediate F, Intermediate G, Intermediate H, Intermediate I, Intermediate J, Intermediate K, Intermediate L.

Method for Preparation of Intermediate A 4-(2-Fluoro-4-nitrophenoxy)-6-methoxyquinolyl-7-ol

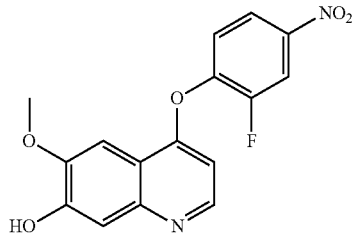 [SMILES: COc1cc2c(Oc3ccc([N+](=O)[O-])cc3F)ccnc2cc1O]

Intermediate A was prepared according to the method described in WO2008/035209. The characterization of the resulting product was as follows: $^1HNMR$ (400 MHz, DMSO-$d_6$): δ=11.74 (s, br, 1H), 8.76 (d, J=6.8 Hz, 1H), 8.47 (dd, J=2.8 Hz, J=10.4 Hz, 1H), 8.23 (dd, J=1.2 Hz, J=8.8 Hz, 1H), 7.81 (m, 1H), 7.65 (s, 1H), 7.49 (s, 1H), 7.04 (d, J=6.4 Hz, 1H), 3.94 (s, 3H).

Method for Preparation of Intermediate B 4-(2-Fluoro-4-nitrophenoxy)-7-methoxyquinolyl-6-ol

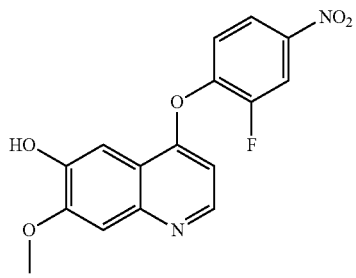 [SMILES: COc1cc2nccc(Oc3ccc([N+](=O)[O-])cc3F)c2cc1O]

Intermediate B was prepared according to the methods described in WO2003/033472 and WO2004/039782. The characterization of the resulting product was: Mass spectrum m/z: 331.12 [M+H].

Method for Preparation of Intermediate C

Tert-Butyl 4-[[4-(4-amino-2-fluorophenyloxy)-6-methoxy-7-quinolyl]oxymethyl]piperidine-1-carboxylate

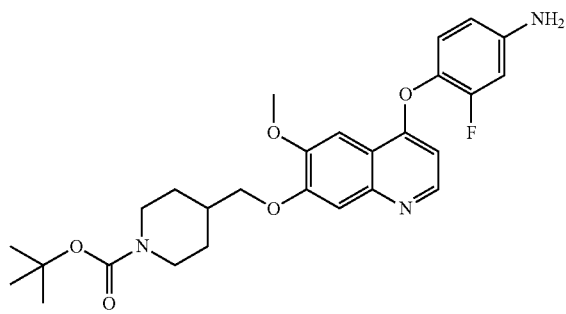 [SMILES: COc1cc2c(Oc3ccc(N)cc3F)ccnc2cc1OCC1CCN(C(=O)OC(C)(C)C)CC1]

Intermediate C was prepared according to the methods described in WO2008/076415. The characterization of the resulting product was as follows: Mass spectrum m/z: 498.21 [M+H].

Method for Preparation of Intermediate D

1-[(4-Fluorophenyl)aminocarbonyl]cyclopropanecarboxylic acid

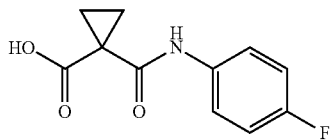 [SMILES: O=C(O)C1(C(=O)Nc2ccc(F)cc2)CC1]

Intermediate D was prepared according to the methods described in WO2005/030140. The characterization of the resulting product was as follows: $^1$HNMR (400 MHz, DMSO-$d_6$): δ=13.0 (s, 1H), 10.6 (s, 1H), 7.62-7.57 (m, 2H), 7.15-7.09 (m, 2H), 1.39 (s, 4H).

Method for Preparation of Intermediate E

4-(4-Amino-2-fluorophenyloxy)-6-methoxy-7-hydroxyquinoline hydrobromide

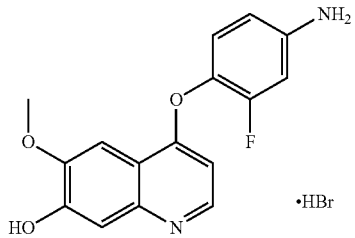 [SMILES: COc1cc2c(Oc3ccc(N)cc3F)ccnc2cc1O ; Br]

To a solution of hydrobromide salt of 4-(2-fluoro-4-nitrophenoxy)-6-methoxy-7-hydroxyquinoline (Intermediate A) (40 g, 97 mmol) in methanol (1000 mL) was added Raney nickel (40 g). The resulting mixture was stirred at 20° C. under a hydrogen pressure of 30 psi for 19 hours. The catalyst was removed by filtration, and the filtrate was concentrated under reduced pressure to obtain the desired product 4-(4-amino-2-fluorophenyloxy)-6-methoxy-7-hydroxyquinoline hydrobromide (34.4 g, yield: 93.3%). The characterization of the resulting product was as follows: Mass spectrum m/z: 300.9 [M+H].

Method for Preparation of Intermediate F

4-(4-Amino-2-fluorophenyloxy)-7-methoxy-6-hydroxyquinoline hydrobromide

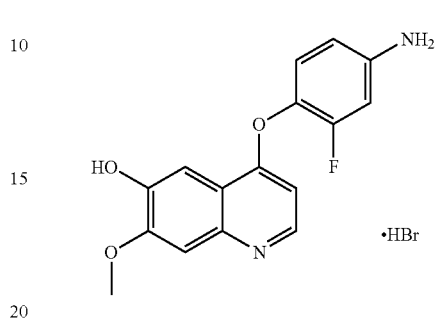

Starting from Intermediate B, Intermediate F was prepared according to the same method as that of Intermediate E. The characterization of the resulting product was as follows: Mass spectrum m/z: 301.0 [M+H].

Method for Preparation of Intermediate G

N1'-[3-Fluoro-4-[(7-hydroxy-6-methoxy-4-quinolyl)oxy]phenyl]-N1-(4-fluorophenyl)cyclopropane-1,1-dicarboxamide

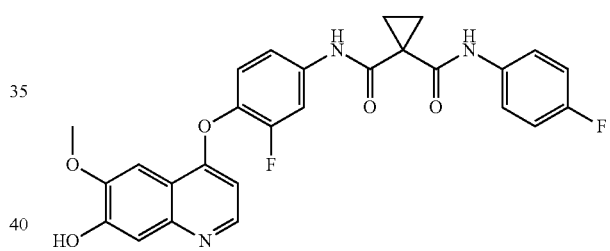

A mixture of 4-(4-amino-2-fluorophenyloxy)-6-methoxy-7-hydroxyquinoline hydrobromide (Intermediate E, 30 g, 79 mmol), 1-[(4-fluorophenyl)aminocarbonyl]cyclopropanecarboxylic acid (Intermediate D, 40 g, 180 mmol), DIPEA (48.8 g, 400 mmol), HATU (115 g, 300 mmol) and DMAP (12.9 g, 100 mmol) in 300 mL of DMF was stirred at 30-40° C. overnight, and the reaction mixture was then poured into 200 mL of water and extracted with ethyl acetate for 3 times (200 mL for each time). The organic phases were combined, dried over sodium sulfate, and concentrated to approximately 150 mL followed by washed with 15% aqueous solution of sodium hydroxide and water for 3 times (100 mL for each time), dried over sodium sulfate and concentrated to obtain a crude product. The crude product was purified by silica gel column chromatography (eluted with a solution of 1%-10% methanol in dichloromethane) to give the desired product N1'-[3-fluoro-4-[(7-hydroxy-6-methoxy-4-quinolyl)oxy]phenyl]-N1-(4-fluorophenyl)cyclopropane-1,1-dicarboxamide (22 g, yield: 55%). The characterization of the resulting product: $^1$HNMR (400 MHz, DMSO-$d_6$): δ=10.11 (s, 1H), 10.01 (s, 1H), 8.48 (d, J=5.6 Hz, 1H), 7.92 (dd, J=2.0, 13.2 Hz, 1H), 7.66-7.61 (m, 2H), 7.56-7.52 (m, 2H), 7.41 (t, J=8.8 Hz, 1H), 7.33 (s, 1H), 7.18-7.12 (m, 2H), 6.45 (d, J=5.6 Hz, 1H), 3.97 (s, 3H), 1.46 (d, J=10.4 Hz, 4H). Mass spectrum m/z: 506.2 [M+H].

Method for Preparation of Intermediate H

N1'-[3-Fluoro-4-[(6-hydroxy-7-methoxy-4-quinolyl)oxy]phenyl]-N1-(4-fluorophenyl)cyclopropane-1,1-dicarboxamide

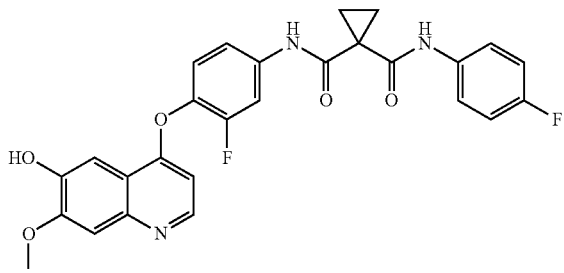 [SMILES: COc1cc2nccc(Oc3ccc(NC(=O)C4(C(=O)Nc5ccc(F)cc5)CC4)cc3F)c2cc1O]

Starting from Intermediate F and D, Intermediate H was prepared according to the same method as that of Intermediate G. The characterization of the resulting product was as follows: Mass spectrum m/z: 506.1 [M+H].

Method for Preparation of Intermediate I

N1-[3-Fluoro-4-[[6-methoxy-7-(4-piperidylmethoxy)-4-quinolyl]oxy]phenyl]-N1'-(4-fluorophenyl)cyclopropane-1,1-dicarboxamide dihydrochloride

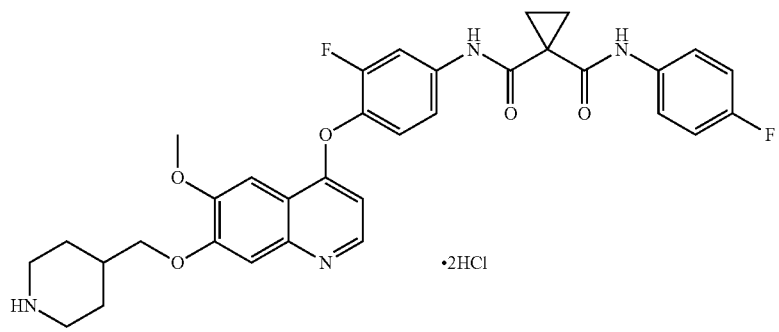 [SMILES: COc1cc2c(Oc3ccc(NC(=O)C4(C(=O)Nc5ccc(F)cc5)CC4)cc3F)ccnc2cc1OCC1CCNCC1]

Step I: Preparation of tert-butyl 4-[[4-[2-fluoro-4-[[1-[(4-fluorophenyl)amino carbonyl]cyclopropanecarbonyl]amino]phenoxy]-6-methoxy-7-quinolyl]oxymethyl]piperidine-1-carboxylate: A mixture of Intermediate C (1.5 g, 3.0 mmol), Intermediate D (1.7 g, 7.6 mmol), DIPEA (1.55 g, 12.0 mmol), HATU (2.3 g, 6.0 mmol), DMAP (0.183 g, 1.5 mmol) in 60 mL of DMF was stirred at 30-40° C. overnight, then concentrated under reduced pressure. The residue was purified by column chromatography (eluted with 1-5% MeOH in DCM) to afford the target product (1.9 g, yield: 90%). The characterization of the resulting product was as follows: Mass spectrum m/z: 703.30 [M+H].

Step II: Preparation of N1-[3-fluoro-4-[[6-methoxy-7-(4-piperidylmethoxy)-4-quinolyl]oxy]phenyl]-N1'-(4-fluorophenyl)cyclopropane-1,1-dicarboxamide dihydrochloride: To a solution of tert-butyl 4-[[4-[2-fluoro-4-[[1-[(4-fluorophenyl)amino carbonyl]cyclopropanecarbonyl]amino]phenoxy]-6-methoxy-7-quinolyl]oxymethyl]piperidine-1-carboxylate (1.6 g, 2.3 mmol) obtained in step I in EtOAc (40 mL) was added saturated solution of HCl in EtOAc (40 mL) at 0° C. The resulting mixture was stirred at room temperature for 4 hours. The precipitate was collected by filtration, and washed with EtOAc to give the target compound (1.0 g, yield: 69%). The characterization of the resulting product was as follows: Mass spectrum m/z: 603.10 [M+H].

Method for preparation of Intermediate J

N1'-[3-Fluoro-4-[[7-methoxy-6-(4-piperidylmethoxy)-4-quinolyl]oxy]phenyl]-N1-(4-fluorophenyl)cyclopropane-1,1-dicarboxamide dihydrochloride

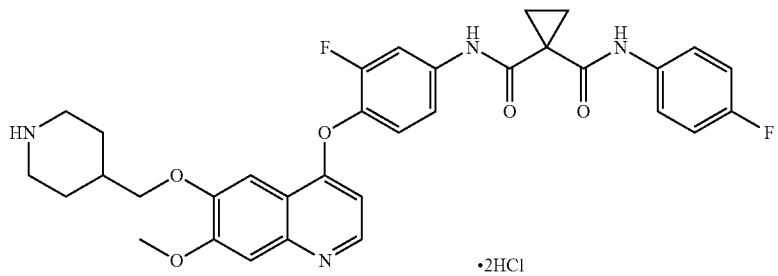 [SMILES: COc1cc2nccc(Oc3ccc(NC(=O)C4(C(=O)Nc5ccc(F)cc5)CC4)cc3F)c2cc1OCC1CCNCC1]

Intermediate J was prepared according to the same method as that of Intermediate I. The characterization of the resulting product was as follows: Mass spectrum m/z: 603.24 [M+H].

Method for Preparation of Intermediate K

N1'-[4-[[7-(3-Aminopropoxy)-6-methoxy-4-quinolyl]oxy]-3-fluorophenyl]-N1-(4-fluorophenyl)cyclopropane-1,1-dicarboxamide dihydrochloride

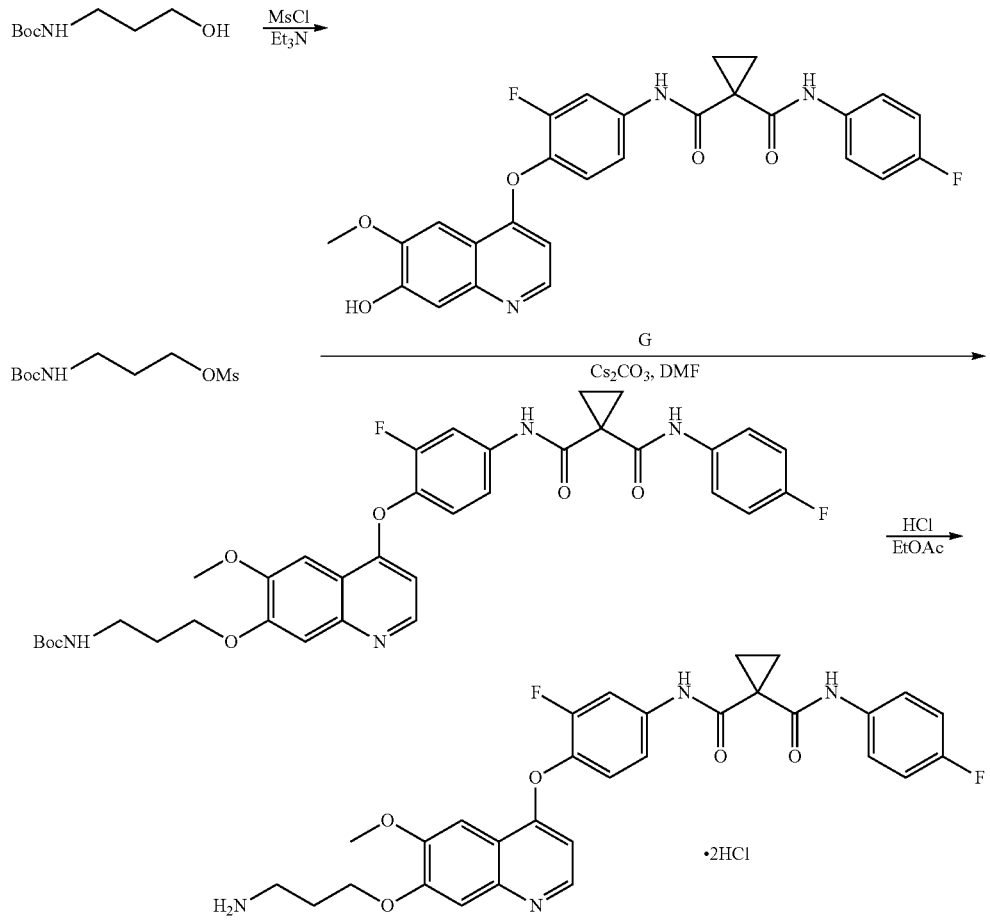

Step I: Preparation of 3-(tert-butyloxycarbonylamino)propyl methanesulfonate: To a solution of 3-(Boc-amino)-propanol (10 g, 57.5 mmol) in dichloromethane (100 mL) was added triethylamine (11.6 g, 115 mmol) at 0° C., then methanesulfonyl chloride (7.9 g, 69 mmol) was dropwise added. The resulting mixture was stirred for 1 hour at 0° C., poured into water, and then extracted with dichloromethane for 3 times (100 mL for each time). The organic phases were combined, dried and concentrated to afford the product 3-(tert-butyloxycarbonylamino)propyl methanesulfonate (13.1 g, yield: 94%). The characterization of the resulting product was as follows: $^1$HNMR (400 MHz, CDCl$_3$): δ=4.76 (s, 1H), 4.26 (t, J=6.4 Hz, 2H), 3.22-3.24 (m, 2H), 3.00 (s, 3H), 1.89-1.92 (m, 2H), 1.41 (s, 9H).

Note: The product was not very stable, and should be used as soon as possible upon preparation.

Step II: Preparation of tert-butyl N-[3-[[4-[2-fluoro-4-[[1-[(4-fluorophenyl)amino carbonyl]cyclopropanecarbonyl]amino]phenoxy]-6-methoxy-7-quinolyl]oxy]propyl]carbamate: To a solution of 3-(tert-butyloxycarbonylamino)propyl methanesulfonate (15 g, 59.4 mmol) and N1'-[3-fluoro-4-[(7-hydroxy-6-methoxy-4-quinolyl)oxy]phenyl]-N1-(4-fluorophenyl)cyclopropane-1,1-dicarboxamide (Intermediate G, 6 g, 11.88 mmol) in 80 mL DMF was added cesium carbonate (11.6 g, 35.6 mmol). The resulting mixture was stirred overnight at 20° C., then poured into 200 mL of water and extracted with ethyl acetate for 3 times (200 mL for each time). The organic phases were combined, dried over sodium sulfate, filtered and concentrated to give the crude product. The crude product was purified by silica gel column chromatography (eluted with a solution of 5%-20% methanol in dichloromethane) to give 6 g of the desired product of tert-butyl N-[3-[[4-[2-fluoro-4-[[1-[(4-fluorophenyl)amino carbonyl]cyclopropanecarbonyl]amino]phenoxy]-6-methoxy-7-quinolyl]oxy]propyl]carbamate (yield: 76%). The characterization of the resulting product was as follows: Mass spectrum m/z: 663.1 [M+H].

Step III: Preparation of N1'-[4-[[7-(3-aminopropoxy)-6-methoxy-4-quinolyl]oxy]-3-fluorophenyl]-N1-(4-fluorophenyl)cyclopropane-1,1-dicarboxamide dihydrochloride: To a solution of tert-butyl N-[3-[[4-[2-fluoro-4-[[1-[(4-fluorophenyl)amino carbonyl]cyclopropanecarbonyl]amino]phenoxy]-6-methoxy-7-quinolyl]oxy]propyl]carbamate (6 g, 9.06 mmol) in 20 mL of ethyl acetate was dropwise added a solution of 4 M HCl in 40 mL ethyl acetate. After this, the mixture was stirred for 1 hour at 20° C., and concentrated under reduced pressure to obtain the product, N1'-[4-[[7-(3-aminopropoxy)-6-methoxy-4-quinolyl]oxy]-3-fluorophenyl]-N1-(4-fluorophenyl)cyclopropane-1,1-dicarboxamide hydrochloride (4.8 g, yield: 95%). The characterization of the resulting product was as follows: Mass spectrum m/z: 562.9 [M+H].

Method for Preparation of Intermediate L

N1'-[4-[[6-(3-Aminopropoxy)-7-methoxy-4-quinolyl]oxy]-3-fluorophenyl]-N1-(4-fluorophenyl)cyclopropane-1,1-dicarboxamide dihydrochloride

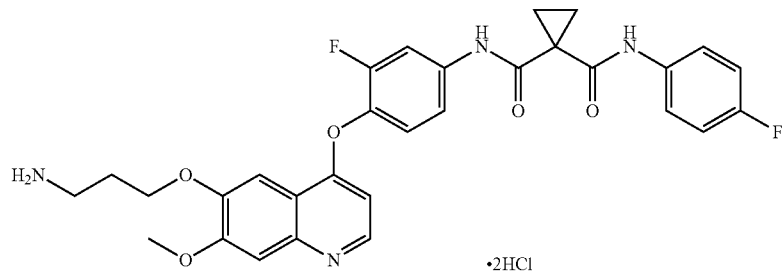 [SMILES: COc1cc2nccc(Oc3ccc(NC(=O)C4(C(=O)Nc5ccc(F)cc5)CC4)cc3F)c2cc1OCCCN]

Intermediate L was prepared according to the same method as that of Intermediate K. The characterization of the resulting product was as follows: Mass spectrum m/z: 562.9 [M+H].

Example 1

Preparation of N1'-[3-fluoro-4-[[7-[[1-[2-(hydroxyamino)-2-oxoethyl]-4-piperidyl]methoxy]-6-methoxy-4-quinolyl]oxy]phenyl]-N1-(4-fluorophenyl)cyclopropane-1,1-dicarboxamide, which is one of the quinolyl-containing hydroxamic acid compounds of the present invention.

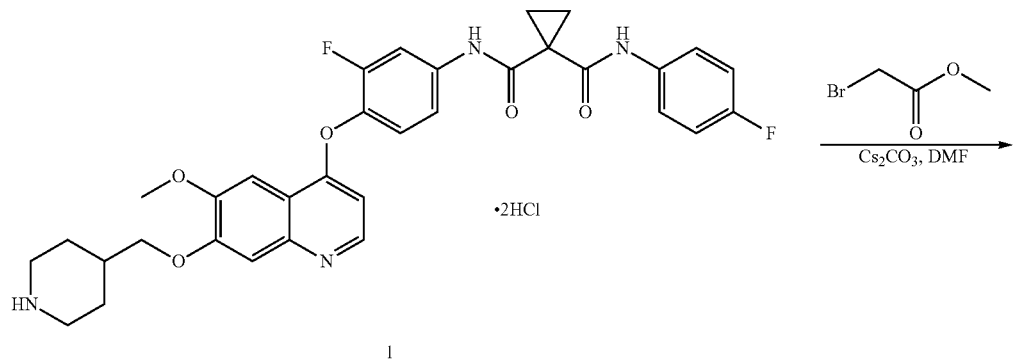

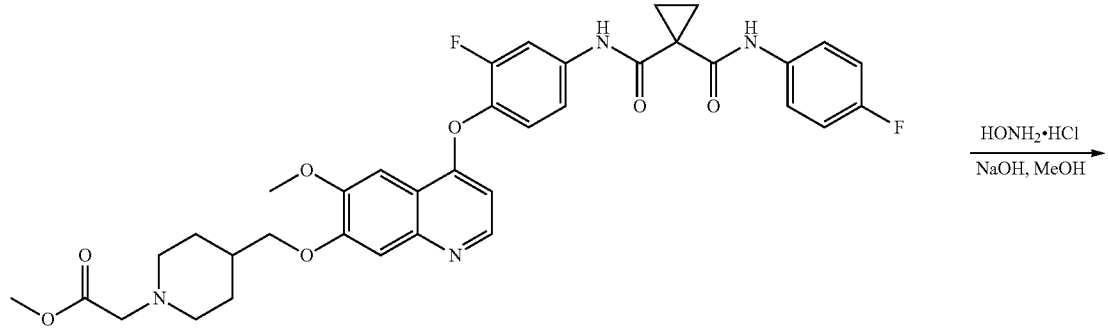

-continued

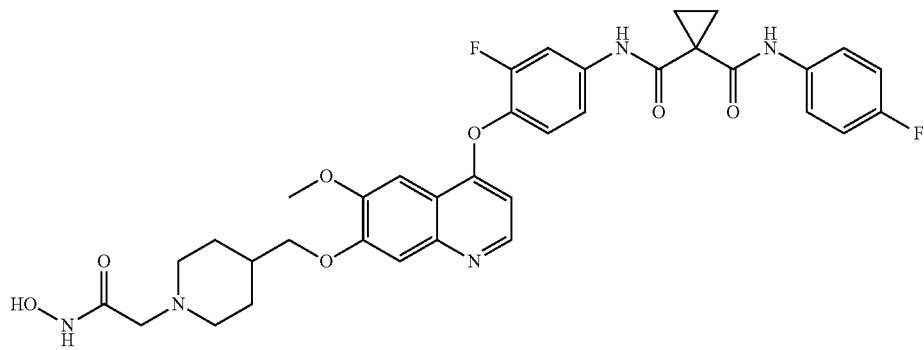

Step I: To a solution of N1'-[3-fluoro-4-[[6-methoxy-7-(4-piperidylmethoxy)-4-quinolyl]oxy]phenyl]-N1-(4-fluorophenyl)cyclopropane-1,1-dicarboxamide hydrochloride (Intermediate I, 3 g, 9.4 mmol) and methyl bromoacetate (1.44 g, 9.4 mmol) in 20 mL DMF was added cesium carbonate (3.1 g, 9.4 mmol). The resulting mixture was stirred at room temperature overnight, poured into 200 mL of water and extracted with ethyl acetate for 3 times (50 mL for each time). The organic phases were combined, washed with saline, dried over sodium sulfate, filtered and concentrated under reduced pressure to give 1.8 g of the crude product methyl 2-[4-[[4-[2-fluoro-4-[[1-[(4-fluorophenyl)amino carbonyl]cyclopropane carbonyl]amino]phenoxy]-6-methoxy-7-quinolyl]oxymethyl]-1-piperidyl]acetate. The crude product was washed with petroleum ether and used directly for the subsequent step without further purification.

Step II: To a solution of methyl 2-[4-[[4-[2-fluoro-4-[[1-[(4-fluorophenyl)amino carbonyl]cyclopropane carbonyl]amino]phenoxy]-6-methoxy-7-quinolyl]oxymethyl]-1-piperidyl]acetate (1.8 g crude product, 2.67 mmol) and hydroxylamine hydrochloride (1.84 g, 26.7 mmol) in 20 mL methanol was added sodium hydroxide (1.07 g, 26.7 mmol). The resulting mixture was stirred at room temperature overnight. The reaction mixture was filtered, and the filtrate was concentrated under reduced pressure to give the crude product. The crude product was purified by silica gel column chromatography (eluted with a solution of 0%-10% methanol in dichloromethane) to afford the desired product N1'-[3-fluoro-4-[[7-[[1-[2-(hydroxyamino)-2-oxoethyl]-4-piperidyl]methoxy]-6-methoxy-4-quinolyl]oxy]phenyl]-N1-(4-fluorophenyl)cyclopropane-1,1-dicarboxamide (225 mg, yield: 12.5%). The characterization of the resulting product was as follows: Mass spectrum m/z: 676.1 [M+H].

Example 2

Preparation of N1'-[3-fluoro-4-[[6-[[1-[2-(hydroxyamino)-2-oxoethyl]-4-piperidyl]methoxy]-7-methoxy-4-quinolyl]oxy]phenyl]-N1-(4-fluorophenyl)cyclopropane-1,1-dicarboxamide, which is one of the quinolyl-containing hydroxamic acid compounds of the present invention.

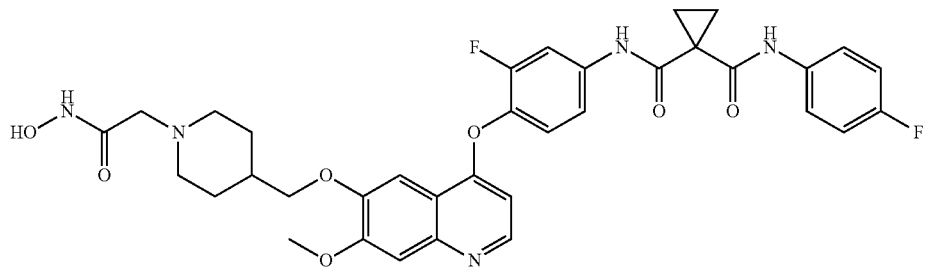 [SMILES: COc1cc2nccc(Oc3ccc(NC(=O)C4(C(=O)Nc5ccc(F)cc5)CC4)cc3F)c2cc1OCC1CCN(CC(=O)NO)CC1]

The preparation was performed according to the same method as Example 1 using Intermediate J. The characterization of the resulting product was as follows: Mass spectrum m/z: 676.1 [M+H].

Example 3

Preparation of N1'-[3-fluoro-4-[[7-[3-[[2-(hydroxyamino)-2-oxoethyl]amino]propoxy]-6-methoxy-4-quinolyl]oxy]phenyl]-N1-(4-fluorophenyl)cyclopropane-1,1-dicarboxamide, which is one of the quinolyl-containing hydroxamic acid compounds of the present invention.

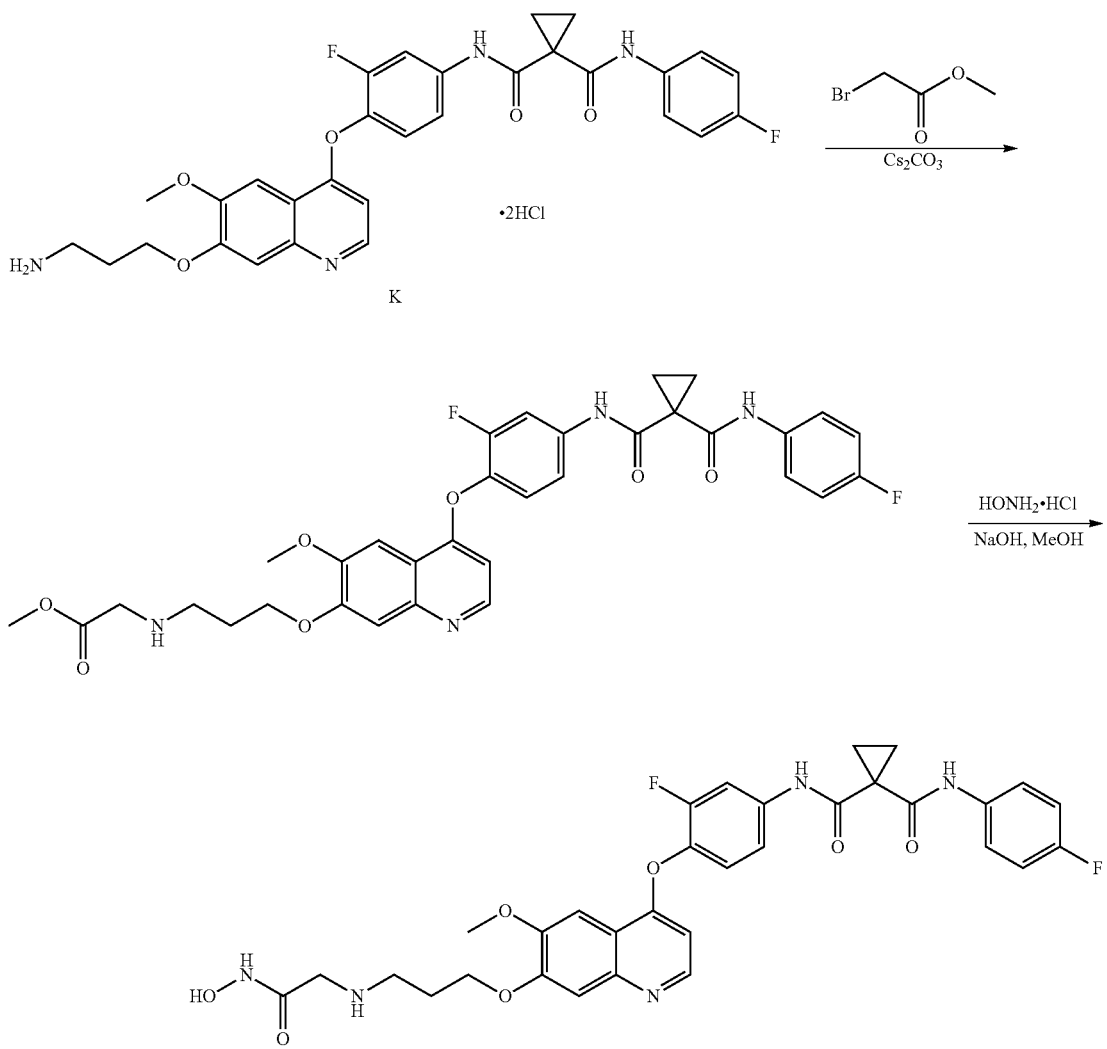

(a) Step I: To a solution of N1'-[4-[[7-(3-aminopropoxy)-6-methoxy-4-quinolyl]oxy]-3-fluorophenyl]-N1-(4-fluorophenyl)cyclopropane-1,1-dicarboxamide hydrochloride (Intermediate K, 2 g, 3.56 mmol) and methyl bromoacetate (0.55 g, 3.56 mmol) in 30 mL acetonitrile was added cesium carbonate (3.48 g, 10.68 mmol). The resulting mixture was stirred overnight at 20° C., then poured into water and extracted with ethyl acetate for 3 times (50 mL for each time). The organic phases were combined, dried over sodium sulfate, filtered and concentrated to give the crude product. The crude product was purified by silica gel column chromatography (eluted with a solution of 0%-10% methanol in dichloromethane) to give the desired product methyl 2-[3-[[4-[2-fluoro-4-[[1-[(4-fluorophenyl)amino carbonyl]cyclopropane carbonyl]amino]phenoxy]-6-methoxy-7-quinolyl]oxy]propylamino]acetate (0.9 g, yield: 40%). The characterization of the resulting product was as follows: Mass spectrum m/z: 635.1 [M+H].

Step II: To a solution of methyl 2-[3-[[4-[2-fluoro-4-[[1-[(4-fluorophenyl)amino carbonyl]cyclopropane carbonyl]amino]phenoxy]-6-methoxy-7-quinolyl]oxy]alanyl]acetate (0.9 g, 1.42 mmol) in 30 mL methanol was added hydroxylamine hydrochloride (0.98 g, 14.2 mmol) and sodium hydroxide (0.57 g, 14.2 mmol). The resulting mixture was stirred overnight at 20° C. The mixture was filtered, the resultant solid was washed with methanol, and the filtrate was concentrated under reduced pressure to give the crude product. The crude product was purified by silica gel column chromatography (eluted with a solution of 1%-15% methanol in dichloromethane) to give the desired product N1'-[3-fluoro-4-[[7-[3-[[2-(hydroxyamino)-2-oxoethyl]amino]propoxy]-6-methoxy-4-quinolyl]oxy]phenyl]-N1-(4-fluorophenyl)cyclopropane-1,1-dicarboxamide (220 mg, yield: 24%). The characterization of the resulting product was as follows: $^1$HNMR (400 MHz, DMSO-$d_6$): δ=11.08 (s, 1H), 10.44 (s, 1H), 10.02 (s, 1H), 9.13 (s, 1H), 8.52 (s, 1H), 7.92 (d, J=21.2 Hz, 1H), 7.68-7.64 (m, 2H), 7.57-7.54 (m, 2H), 7.47-7.44 (m, 2H), 7.16 (t, J=8.0 Hz, 2H), 6.48 (s, 1H), 4.28 (s, 2H), 3.98 (s, 3H), 3.70 (m, 1H), 3.18-3.15 (m, 4H), 3.24-3.22 (m, 2H), 1.49 (d, J=5.2 Hz, 4H). Mass spectrum m/z: 636.1 [M+H].

Example 4

Preparation of N1'-[3-fluoro-4-[[6-[3-[[2-(hydroxyamino)-2-oxopropyloxoethyl]amino]propoxy]-7-methoxy-4-quinolyl]oxy]phenyl]-N1-(4-fluorophenyl)cyclopropane-1,1-dicarboxamide, which is one of the quinolyl-containing hydroxamic acid compounds of the present invention.

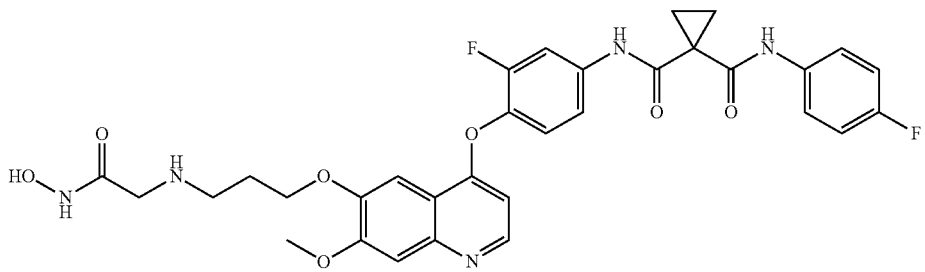 [SMILES: COc1cc2nccc(Oc3ccc(NC(=O)C4(C(=O)Nc5ccc(F)cc5)CC4)cc3F)c2cc1OCCCNCC(=O)NO]

The preparation was performed according to the same method as Example 3 using Intermediate L. The characterization of the resulting product was as follows: Mass spectrum m/z: 636.1 [M+H].

Example 5

Preparation of N1'-[3-fluoro-4-[[7-[3-[[3-(hydroxyamino)-3-oxopropyl]amino]propoxy]-6-methoxy-4-quinolyl]oxy]phenyl]-N1-(4-fluorophenyl)cyclopropane-1,1-dicarboxamide, which is one of the quinolyl-containing hydroxamic acid compounds of the present invention.

overnight at 40° C. The reacting mixture was poured into 20 mL water and extracted with ethyl acetate for 3 times (50 mL for each time). The organic phases were combined, dried over sodium sulfate, filtered and concentrated to give the crude product. The crude product was purified by silica gel column chromatography (eluted with a solution of 5%-20% methanol in dichloromethane) to give the desired product methyl 3-[3-[[4-[2-fluoro-4-[[1-[(4-fluorophenyl)amino carbonyl]cyclopropane carbonyl]amino]phenoxy]-6-methoxy-7-quinolyl]oxy]propylamino]propionate (0.648 g, yield: 55%). The characterization of the resulting product was as follows: Mass spectrum m/z: 649.1 [M+H].

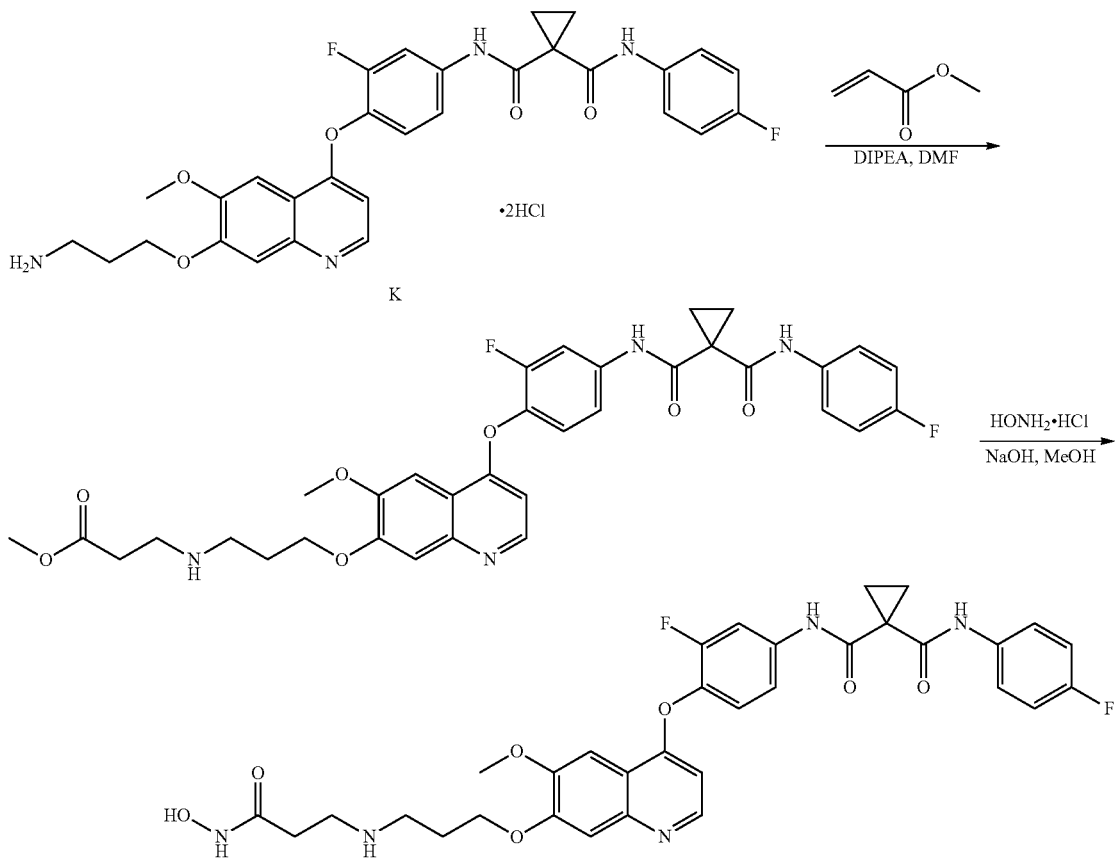

(a) Step I: A mixture of N1'-[4-[[7-(3-aminopropoxy)-6-methoxy-4-quinolyl]oxy]-3-fluorophenyl]-N1-(4-fluorophenyl)cyclopropane-1,1-dicarboxamide hydrochloride (Intermediate K, 1.0 g, 1.8 mmol), methyl acrylate (0.28 g, 3.25 mmol) and DIPEA (5 mL) in 10 mL DMF was heated Step II: To a solution of methyl 3-[3-[[4-[2-fluoro-4-[[1-[(4-fluorophenyl)amino carbonyl]cyclopropane carbonyl]amino]phenoxy]-6-methoxy-7-quinolyl]oxy]propylamino]propionate (0.648 g, 1.00 mmol) in 30 mL methanol was added hydroxylamine hydrochloride (0.69 g, 10.0 mmol) and sodium hydroxide (0.40 g, 10.0 mmol). The resulting mixture was stirred overnight at 20° C. The mixture was filtered, the resultant solid was washed with methanol, and the resultant filtrate was concentrated under reduced pressure to give the crude product. The crude product was purified by silica gel column chromatography (eluted with a solution of 1%-15% methanol in dichloromethane) to give the desired product N1'-[3-fluoro-4-[[7-[3-[[3-(hydroxyamino)-3-oxopropyl]amino]propoxy]-6-methoxy-4-quinolyl]oxy]phenyl]-N1-(4-fluorophenyl)cyclopropane-1,1-dicarboxamide (203 mg, yield: 31%). The characterization of the resulting product was as follows: $^1$HNMR (400 MHz, DMSO-$d_6$): δ=10.70 (s, 1H), 10.42 (s, 1H), 10.02 (s, 1H), 8.93 (s, 1H), 8.78 (s, 1H), 8.50 (s, 1H), 7.92 (d, J=15.2 Hz, 1H), 7.65-7.63 (m, 2H), 7.56-7.53 (m, 2H), 7.45-7.43 (m, 2H), 7.17 (t, J=7.6 Hz, 2H), 6.46 (s, 1H), 4.27 (m, 2H), 3.97 (s, 3H), 3.18-3.14 (m, 6H), 2.21-2.19 (m, 2H), 1.48 (d, J=6.0 Hz, 4H). Mass spectrum m/z: 650.1 [M+H].

Example 6

Preparation of N1'-[3-fluoro-4-[[6-[3-[[3-(hydroxyamino)-3-oxopropyl]amino]propoxy]-7-methoxy-4-quinolyl]oxy]phenyl]-N1-(4-fluorophenyl)cyclopropane-1,1-dicarboxamide, which is one of the quinolyl-containing hydroxamic acid compounds of the present invention.

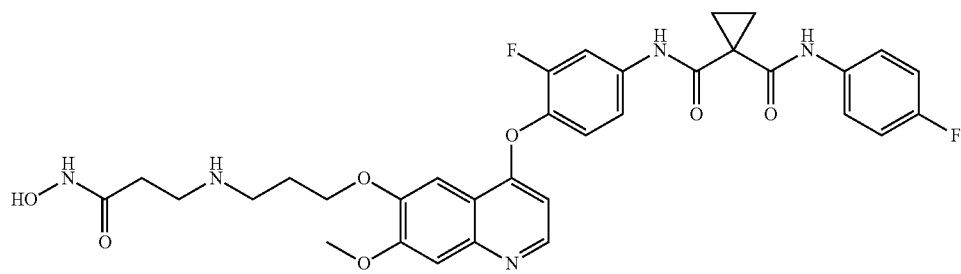 [SMILES: COc1cc2nccc(Oc3ccc(NC(=O)C4(C(=O)Nc5ccc(F)cc5)CC4)cc3F)c2cc1OCCCNCCC(=O)NO]

The preparation was performed according to the same method as Example 5 using Intermediate L. The characterization of the resulting product was as follows: Mass spectrum m/z: 650.1 [M+H].

Example 7

Preparation of N1'-[3-fluoro-4-[[7-[2-(hydroxyamino)-2-oxoethoxy]-6-methoxy-4-quinolyl]oxy]phenyl]-N1-(4-fluorophenyl)cyclopropane-1,1-dicarboxamide, which is one of the quinolyl-containing hydroxamic acid compounds of the present invention.

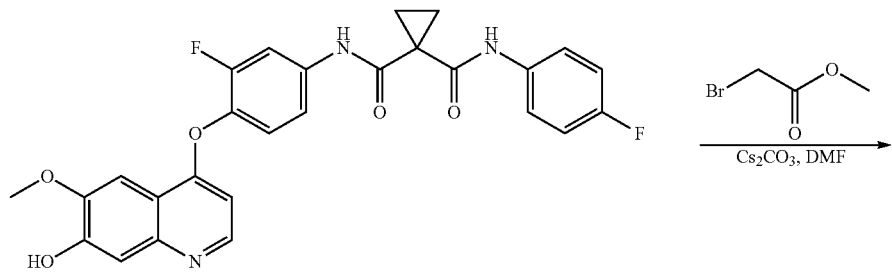

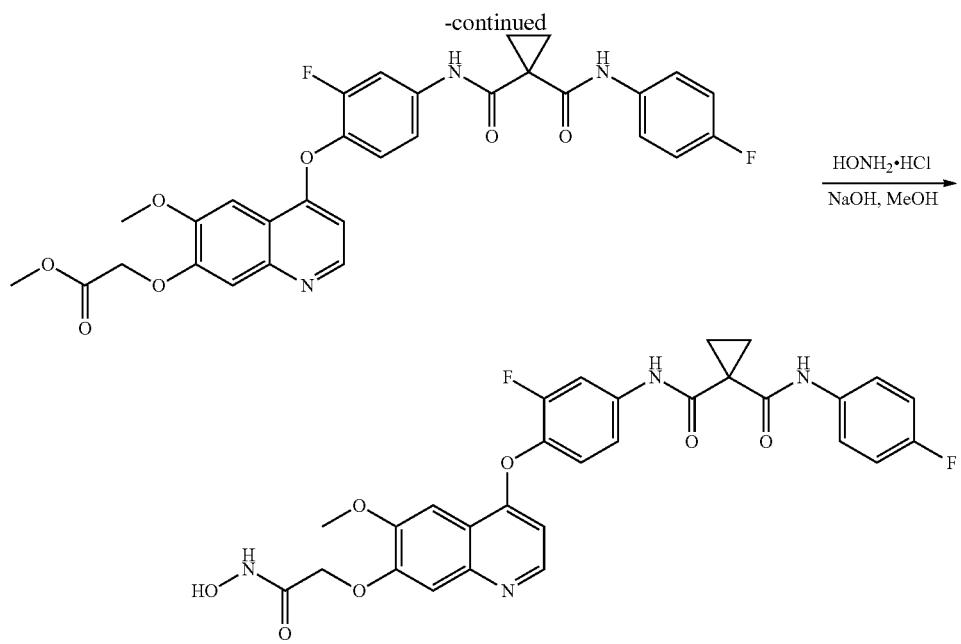

(a) Step I: To a solution of N1'-[3-fluoro-4-[(7-hydroxy-6-methoxy-4-quinolyl)oxy]phenyl]-N1-(4-fluorophenyl)cyclopropane-1,1-dicarboxamide (Intermediate G, 2 g, 3.96 mmol) and methyl bromoacetate (1.2 g, 7.92 mmol) in 20 mL DMF was added cesium carbonate (2.6 g 7.92 mmol). The resulting mixture was stirred at room temperature overnight, poured into 200 mL of water and extracted with ethyl acetate for 3 times (50 mL for each time). The organic phases were combined, washed with saline, dried over sodium sulfate, filtered and concentrated under reduced pressure to obtain 2.1 g of the crude product. The crude product was washed with petroleum ether and used directly to the subsequent step without further purification.

Step II: To a solution of methyl 2-[[4-[2-fluoro-4-[[1-[(4-fluorophenyl)aminocarbonyl]cyclopropanecarbonyl]amino]phenoxy]-6-methoxy-7-quinolyl]oxy]acetate (2.1 g, 3.64 mmol of the crude product) and hydroxylamine hydrochloride (2.5 g 36.4 mmol) in 20 mL methanol was added sodium hydroxide (1.46 g, 36.4 mmol). The resulting mixture was stirred at room temperature overnight. The reaction mixture was filtered, and the filtrate was concentrated under reduced pressure to give the crude product. The crude product was purified by silica gel column chromatography (eluted with a solution of 0%-10% methanol in dichloromethane) to give the desired product N1'-[3-fluoro-4-[[7-[2-(hydroxyamino)-2-oxoethoxy]-6-methoxy-4-quinolyl]oxy]phenyl]-N1-(4-fluorophenyl)cyclopropane-1,1-dicarboxamide (251 mg, yield: 12%). The characterization of the resulting product was as follows: $^1$HNMR (400 MHz, DMSO-$d_6$): δ=10.92 (s, 1H), 10.39 (s, 1H), 10.01 (s, 1H), 9.09 (s, 1H), 8.48 (d, J=5.2 Hz, 1H), 7.91 (dd, J=1.6, 13.2 Hz, 1H), 7.66-7.62 (m, 2H), 7.55-7.51 (m, 2H), 7.44-7.36 (m, 2H), 7.15 (t, J=8.8 Hz, 2H), 6.44 (d, J=4.8 Hz, 1H), 4.65 (s, 2H), 3.96 (s, 3H), 1.47 (d, J=2.0 Hz, 4H). Mass spectrum m/z: 579.1 [M+H].

Example 8

Preparation of N1'-[3-fluoro-4-[[6-[2-(hydroxyamino)-2-oxoethoxy]-7-methoxy-4-quinolyl]oxy]phenyl]-N1-(4-fluorophenyl)cyclopropane-1,1-dicarboxamide, which is one of the quinolyl-containing hydroxamic acid compounds of the present invention.

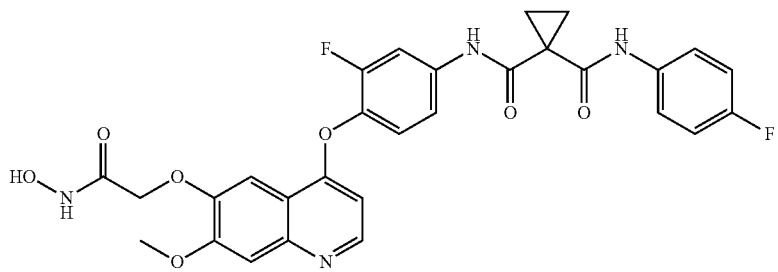 [SMILES: COc1cc2nccc(Oc3ccc(NC(=O)C4(C(=O)Nc5ccc(F)cc5)CC4)cc3F)c2cc1OCC(=O)NO]

The preparation was performed according to the same method as Example 7 using Intermediate H. The characterization of the resulting product was as follows: Mass spectrum m/z: 579.1 [M+H].

Example 9

Preparation of N1'-[3-fluoro-4-[[7-[4-(hydroxyamino)-4-oxobutoxy]-6-methoxy-4-quinolyl]oxy]phenyl]-N1-(4-fluororophenyl)cyclopropane-1,1-dicarboxamide, which is one of the quinolyl-containing hydroxamic acid compounds of the present invention.

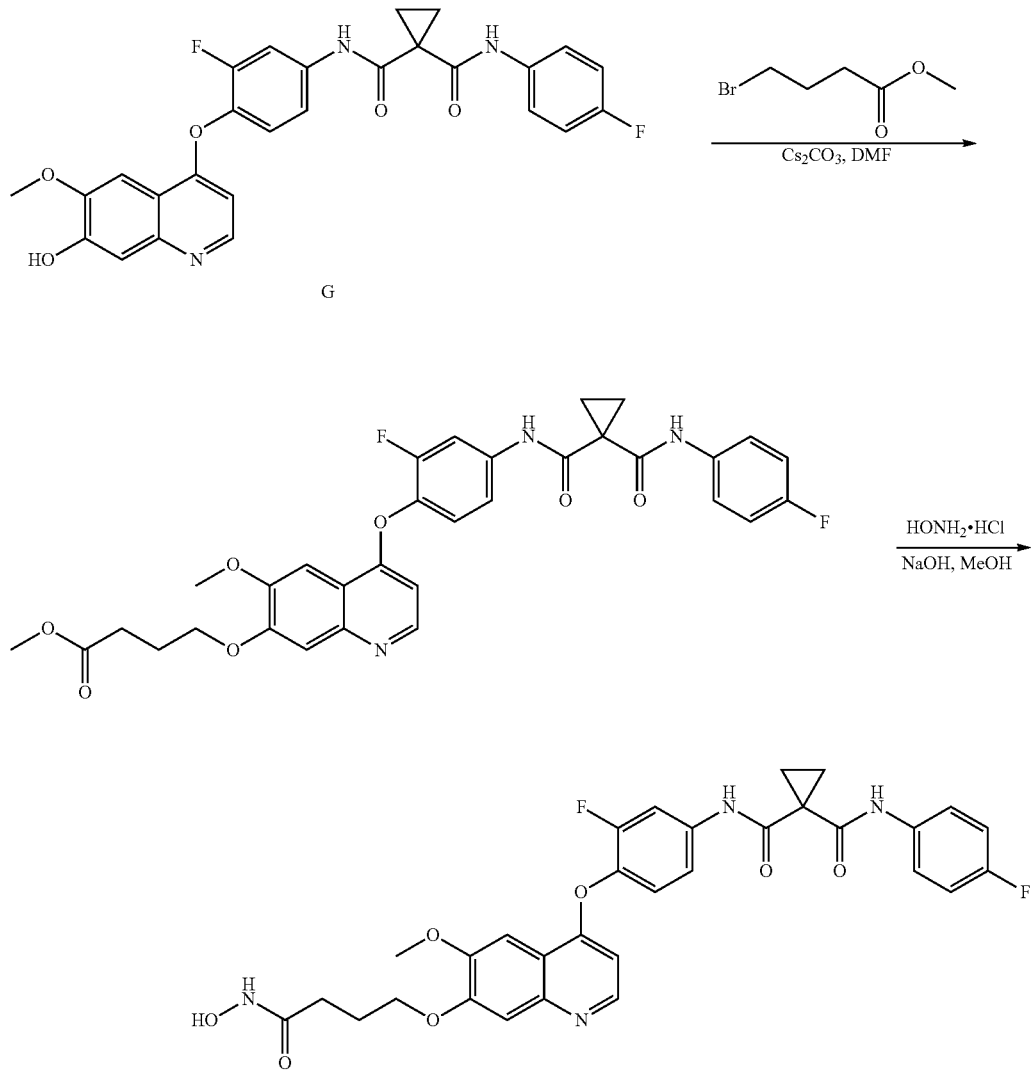

(a) Step I: To a solution of N1'-[3-fluoro-4-[(7-hydroxy-6-methoxy-4-quinolyl)oxy]phenyl]-N1-(4-fluorophenyl)cyclopropane-1,1-dicarboxamide (Intermediate G, 2 g, 3.96 mmol) and methyl 4-bromobutyrate (1.4 g, 7.92 mmol) in 20 mL DMF was added cesium carbonate (2.6 g, 7.92 mmol). The resulting mixture was stirred at room temperature overnight, poured into 200 mL of water and extracted with ethyl acetate for 3 times (50 mL for each time). The organic phases were combined, washed with saline, dried over sodium sulfate, filtered and concentrated under reduced pressure to obtain 1.5 g of the crude product. The crude product was washed with petroleum ether and used directly to the subsequent step without further purification.

Step II: To a solution of methyl 4-[[4-[2-fluoro-4-[[1-[(4-fluorophenyl)aminocarbonyl]cyclopropanecarbonyl]amino]phenoxy]-6-methoxy-7-quinolyl]oxy]butyrate (1.5 g of crude product, 2.48 mmol) and hydroxylamine hydrochloride (1.71 g, 24.8 mmol) in 20 mL methanol was added sodium hydroxide (1.00 g, 24.8 mmol). The resulting mixture was stirred at room temperature overnight, and the filtrate was concentrated under reduced pressure to give the crude product. The crude product was purified by silica gel column chromatography (eluted with a solution of 0%-10% methanol in dichloromethane) to give the desired product N1'-[3-fluoro-4-[[7-[4-(hydroxyamino)-4-oxobutoxy]-6-methoxy-4-quinolyl]oxy]phenyl]-N1-(4-fluorophenyl)cyclopropane-1,1-dicarboxamide (290 mg, yield: 19%). The characterization of the resulting product was as follows: $^1$HNMR (400 MHz, DMSO-$d_6$): δ=10.46 (s, 1H), 10.38 (s, 1H), 10.00 (s, 1H), 8.74 (s, 1H), 8.46 (d, J=5.2 Hz, 1H), 7.91 (dd, J=1.6, 13.2 Hz, 1H). 7.65-7.62 (m, 2H), 7.52-7.50 (m, 2H), 7.43-7.38 (m, 2H), 7.17-7.13 (m, 2H), 6.41 (dd, J=1.2, 5.6 Hz, 1H), 4.15 (t, J=6.4 Hz, 2H), 3.95 (s, 3H), 2.18 (m, 2H), 2.03 (m, 2H), 1.46 (s, 4H). Mass spectrum m/z: 607.0 [M+H].

Example 10

Preparation of N1'-[3-fluoro-4-[[6-[4-(hydroxyamino)-4-oxobutoxy]-7-methoxy-4-quinolyl]oxy]phenyl]-N1-(4-fluorophenyl)cyclopropane-1,1-dicarboxamide, which is one of the quinolyl-containing hydroxamic acid compounds of the present invention:

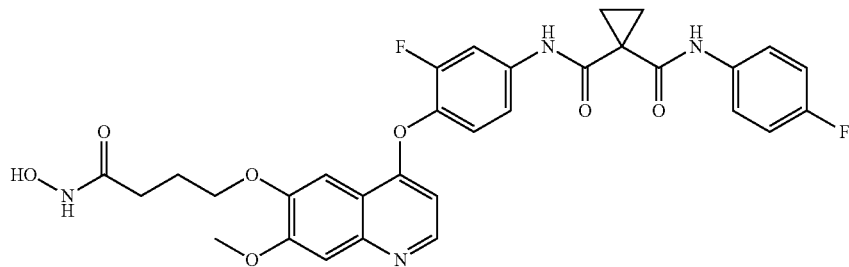 [SMILES: COc1cc2nccc(Oc3ccc(NC(=O)C4(C(=O)Nc5ccc(F)cc5)CC4)cc3F)c2cc1OCCCC(=O)NO]

The preparation was performed according to the same method as Example 9 using Intermediate H. The characterization of the resulting product was as follows: Mass spectrum m/z: 607.1 [M+H].

Example 11

Preparation of N1'-[3-fluoro-4-[[7-[5-(hydroxyamino)-5-oxopentyloxy]-6-methoxy-4-quinolyl]oxy]phenyl]-N1-(4-fluorophenyl)cyclopropane-1,1-dicarboxamide, which is one of the quinolyl-containing hydroxamic acid compounds of the present invention:

(a) Step I: To a solution of N1'-[3-fluoro-4-[(7-hydroxy-6-methoxy-4-quinolyl)oxy]phenyl]-N1-(4-fluorophenyl)cyclopropane-1,1-dicarboxamide (Intermediate G, 2 g, 3.96 mmol) and methyl 5-bromovalerate (1.55 g, 7.92 mmol) in 20 mL DMF was added cesium carbonate (2.6 g, 7.92 mmol). The resulting mixture was stirred at room temperature overnight, poured into 200 mL of water and extracted with ethyl acetate for 3 times (50 mL for each time). The organic phases were combined, washed with saline, dried over sodium sulfate, filtered and concentrated under reduced pressure to obtain 2.0 g of the crude product. The crude product was washed with petroleum ether and used directly to the subsequent step without further purification.

Step II: To a solution of methyl 5-[[4-[2-fluoro-4-[[1-[(4-fluorophenyl)amino carbonyl]cyclopropanecarbonyl]amino]

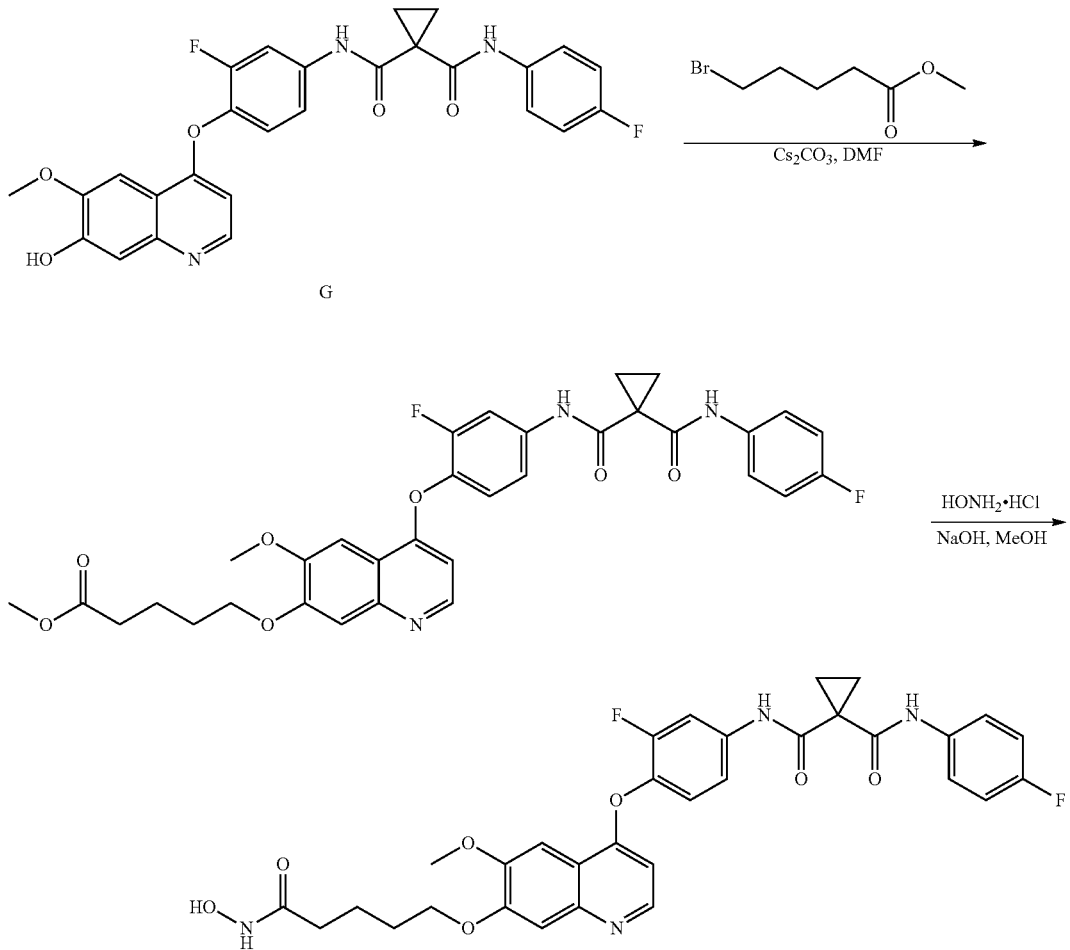

phenoxy]-6-methoxy-7-quinolyl]oxy]pentanoate (2.0 g of crude product, 3.23 mmol) and hydroxylamine hydrochloride (2.22 g, 32.3 mmol) in 20 mL methanol was added sodium hydroxide (1.29 g, 32.3 mmol). The resulting mixture was stirred at room temperature overnight. The reacting mixture was filtered, and the filtrate was concentrated under reduced pressure to give the crude product. The crude product was purified by silica gel column chromatography (eluted with a solution of 0%-10% methanol in dichloromethane) to give the desired product N1'-[3-fluoro-4-[[7-[5-(hydroxyamino)-5-oxopentyloxy]-6-methoxy-4-quinolyl]oxy]phenyl]-N1-(4-fluorophenyl)cyclopropane-1,1-dicarboxamide (284 mg, yield: 14.3%). The characterization of the resulting product was as follows: ¹HNMR (400 MHz, DMSO-d₆): δ=10.39 (s, 1H), 10.38 (s, 1H), 10.00 (s, 1H), 8.72 (d, J=1.2 Hz, 1H), 8.47 (d, J=5.2 Hz, 1H), 7.82 (dd, J=2.0, 15.6 Hz, 1H), 7.66-7.62 (m, 2H), 7.52-7.50 (m, 2H), 7.44-7.39 (m, 2H), 7.17-7.13 (m, 2H), 6.41 (dd, J=1.2, 5.2 Hz, 1H), 4.15 (t, J=6.4 Hz, 2H), 3.95 (s, 3H), 2.06 (m, J=7.2 Hz, 2H), 1.83-1.76 (m, 2H), 1.72-1.64 (m, 2H), 1.47 (d, J=2.4 Hz, 4H). Mass spectrum m/z: 621.0 [M+H].

Example 12

Preparation of N1'-[3-fluoro-4-[6-[5-(hydroxyamino)-5-oxopentyloxy]-7-methoxy-4-quinolyl]oxy]phenyl]-N1-(4-fluorophenyl)cyclopropane-1,1-dicarboxamide, which is one of the quinolyl-containing hydroxamic acid compounds of the present invention.

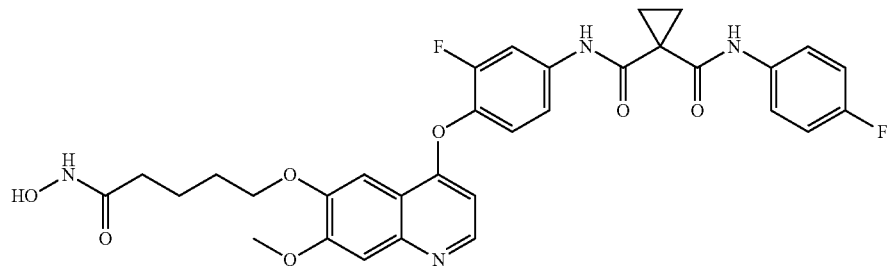 [SMILES: COc1cc2nccc(Oc3ccc(NC(=O)C4(C(=O)Nc5ccc(F)cc5)CC4)cc3F)c2cc1OCCCCC(=O)NO]

The preparation was performed according to the same method as Example 11 using Intermediate H. The characterization of the resulting product was as follows: Mass spectrum m/z: 621.1 [M+H].

Example 13

Preparation of N1'-[3-fluoro-4-[[7-[6-(hydroxyamino)-6-oxohexyloxy]-6-methoxy-4-quinolyl]oxy]phenyl]-N1-(4-fluorophenyl)cyclopropane-1,1-dicarboxamide, which is one of the quinolyl-containing hydroxamic acid compounds of the present invention.

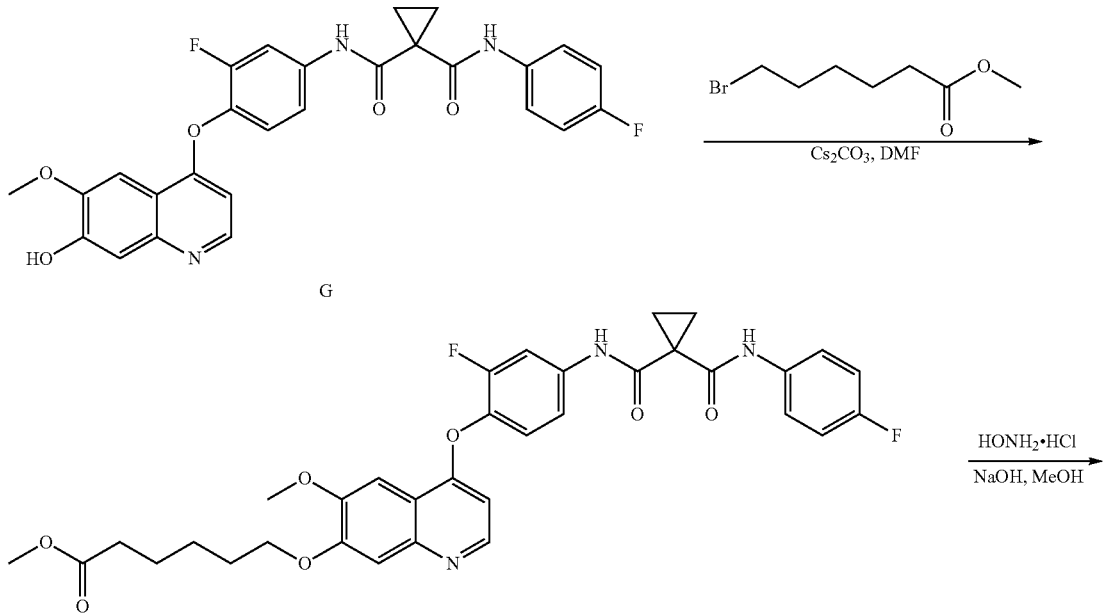

-continued

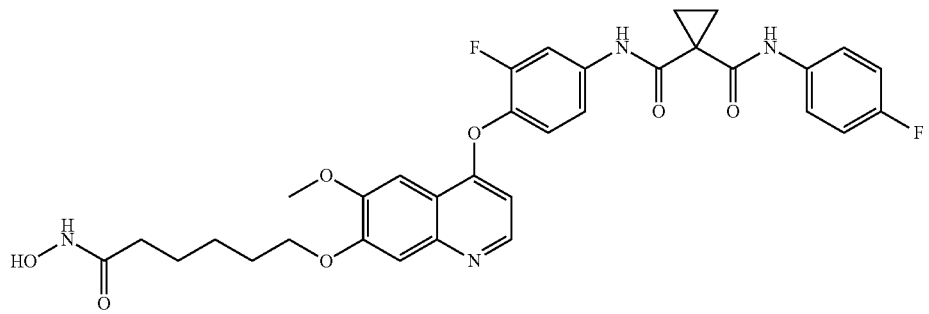

(a) Step I: To a solution of N1'-[3-fluoro-4-[(7-hydroxy-6-methoxy-4-quinolyl)oxy]phenyl]-N1-(4-fluorophenyl)cyclopropane-1,1-dicarboxamide (Intermediate G, 2 g, 3.96 mmol) and methyl 6-bromohexanoate (1.66 g, 7.92 mmol) in 20 mL DMF was added cesium carbonate (2.6 g, 7.92 mmol). The resulting mixture was stirred at room temperature overnight, poured into 200 mL of water and extracted with ethyl acetate for 3 times (50 mL for each time). The organic phases were combined, washed with saline, dried over sodium sulfate, filtered and concentrated under reduced pressure to obtain 1.8 g of the crude product. The crude product was washed with petroleum ether and used directly to the subsequent step without further purification.

Step II: To a solution of methyl 6-[[4-[2-fluoro-4-[[1-[(4-fluorophenyl)aminocarbonyl]cyclopropanecarbonyl]amino]phenoxy]-6-methoxy-7-quinolyl]oxy]hexanoate (1.8 g of crude product, 2.84 mmol) and hydroxylamine hydrochloride (1.96 g, 28.4 mmol) in 20 mL methanol was added sodium hydroxide (1.14 g, 28.4 mmol). The resulting mixture was stirred at room temperature overnight. The reacting mixture was filtered, and the filtrate was concentrated under reduced pressure to give the crude product. The crude product was purified by silica gel column chromatography (eluted with a solution of 0%-10% methanol in dichloromethane) to give the desired product N1'-[3-fluoro-4-[[7-[6-(hydroxyamino)-6-oxohexyloxy]-6-methoxy-4-quinolyl]oxy]phenyl]-N1-(4-fluorophenyl)cyclopropane-1,1-dicarboxamide (207 mg, yield: 11.5%). The characterization of the resulting product was as follows: $^1$HNMR (400 MHz, DMSO-d$_6$): δ=10.38 (s, 1H), 10.37 (s, 1H), 10.00 (s, 1H), 8.69 (s, 1H), 8.46 (d, J=5.2 Hz, 1H), 7.91 (d, J=8.2 Hz, 1H), 7.66-7.62 (m, 2H), 7.52-7.50 (m, 2H), 7.44-7.39 (m, 2H), 7.15 (t, J=8.8 Hz, 2H), 6.41 (dd, J=1.2, 5.2 Hz, 1H), 4.14 (t, J=6.4 Hz, 2H), 3.95 (s, 3H), 2.06 (t, J=6.4 Hz, 2H), 2.00-1.98 (m, 2H), 1.60-1.59 (m, 2H), 1.47 (m, 6H). Mass spectrum m/z: 635.3 [M+H].

Example 14

Preparation of N1'-[3-fluoro-4-[[6-[6-(hydroxyamino)-6-oxohexyloxy]-7-methoxy-4-quinolyl]oxy]phenyl]-N1-(4-fluorophenyl)cyclopropane-1,1-dicarboxamide, which is one of the quinolyl-containing hydroxamic acid compounds of the present invention.

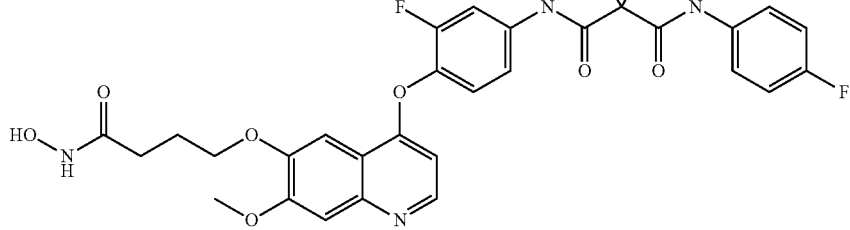

The preparation was performed according to the same method as Example 13 using Intermediate H. The characterization of the resulting product was as follows: Mass spectrum m/z: 635.2 [M+H].

Example 15

Preparation of N1'-[3-fluoro-4-[[7-[7-(hydroxyamino)-7-oxoheptyloxy]-6-methoxy-4-quinolyl]oxy]phenyl]-N1-(4-fluorophenyl)cyclopropane-1,1-dicarboxamide, which is one of the quinolyl-containing hydroxamic acid compounds of the present invention.

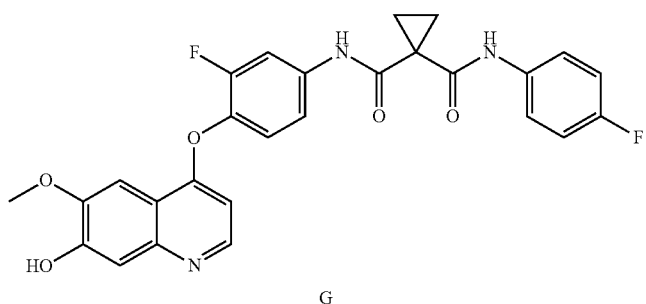
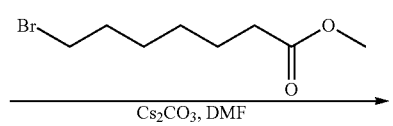
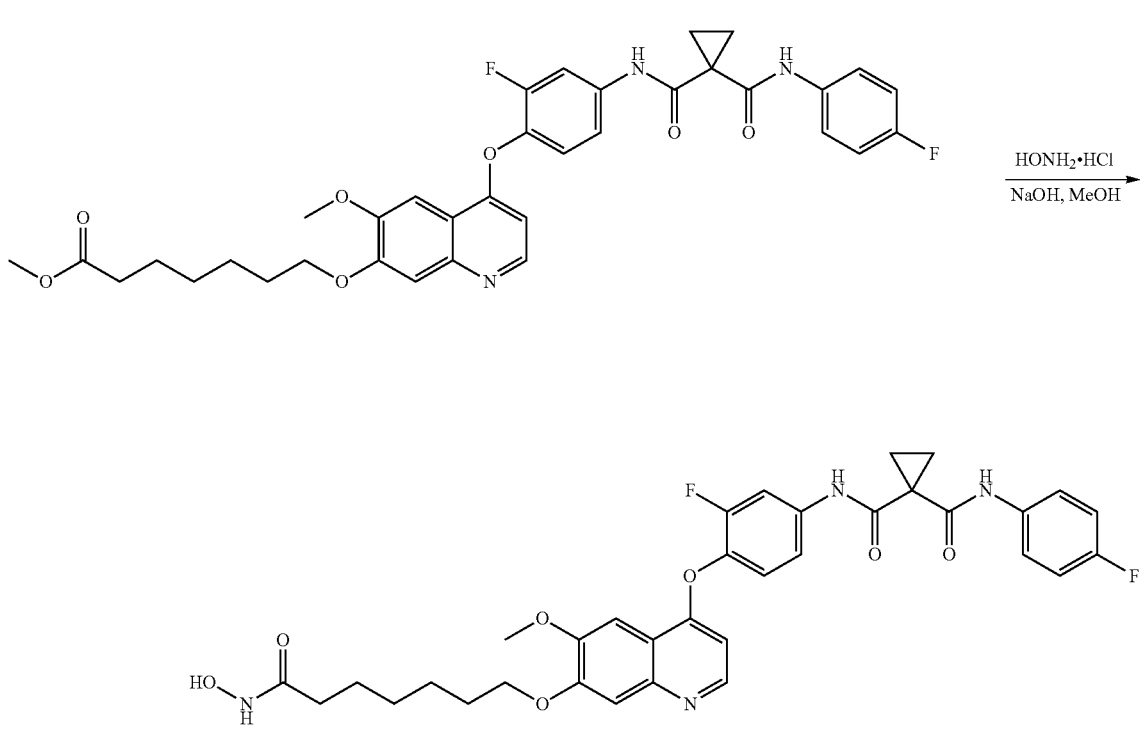

(a) Step I: To a solution of N1'-[3-fluoro-4-[(7-hydroxy-6-methoxy-4-quinolyl)oxy]phenyl]-N1-(4-fluorophenyl)cyclopropane-1,1-dicarboxamide (Intermediate G, 2 g, 3.96 mmol) and methyl 7-bromoheptanoate (1.77 g, 7.92 mmol) in 20 mL DMF was added cesium carbonate (2.6 g, 7.92 mmol). The resulting mixture was stirred at room temperature overnight, poured into 200 mL of water and extracted with ethyl acetate for 3 times (50 mL for each time). The organic phases were combined, washed with saline, dried over sodium sulfate, filtered and concentrated under reduced pressure to obtain 1.7 g of the crude product. The crude product was washed with petroleum ether and used directly to the subsequent step without further purification.

Step II: To a solution of methyl 7-[[4-[2-fluoro-4-[[1-[(4-fluorophenyl)aminocarbonyl]cyclopropanecarbonyl]amino]phenoxy]-6-methoxy-7-quinolyl]oxy]heptanoate (1.7 g of crude product, 2.62 mmol) and hydroxylamine hydrochloride (1.81 g, 26.2 mmol) in 20 mL methanol was added sodium hydroxide (1.05 g, 26.2 mmol). The resulting mixture was stirred at room temperature overnight. The reacting mixture was filtered, and the filtrate was concentrated under reduced pressure to give the crude product. The crude product was purified by silica gel column chromatography (eluted with a solution of 0%-10% methanol in dichloromethane) to give the desired product N1'-[3-fluoro-4-[[7-[7-(hydroxyamino)-7-oxoheptyloxy]-6-methoxy-4-quinolyl]oxy]phenyl]-N1-(4-fluorophenyl)cyclopropane-1,1-dicarboxamide (315 mg, yield: 18.5%). The characterization of the resulting product was as follows: $^1$HNMR (400 MHz, DMSO-$d_6$): δ=10.38 (s, 1H), 10.34 (s, 1H), 10.00 (s, 1H), 8.67 (s, 1H), 8.46 (d, J=5.2 Hz, 1H), 7.90 (dd, J=2.0, 12.8 Hz, 1H), 7.65-7.62 (m, 2H), 7.51-7.50 (m, 2H), 7.43-7.38 (m, 2H), 7.15 (t, J=8.8 Hz, 2H), 6.41 (d, J=4.4 Hz, 1H), 4.13 (t, J=6.4 Hz, 2H), 3.94 (s, 3H), 1.98-1.95 (m, 2H), 1.82-1.78 (m, 2H), 1.55-1.44 (m, 8H), 1.35-1.33 (m, 2H). Mass spectrum m/z: 649.1 [M+H].

Example 16

Preparation of N1'-[3-fluoro-4-[[6-[7-(hydroxyamino)-7-oxoheptyloxy]-7-methoxy-4-quinolyl]oxy]phenyl]-N1-(4-fluorophenyl)cyclopropane-1,1-dicarboxamide, which is one of the quinolyl-containing hydroxamic acid compounds of the present invention.

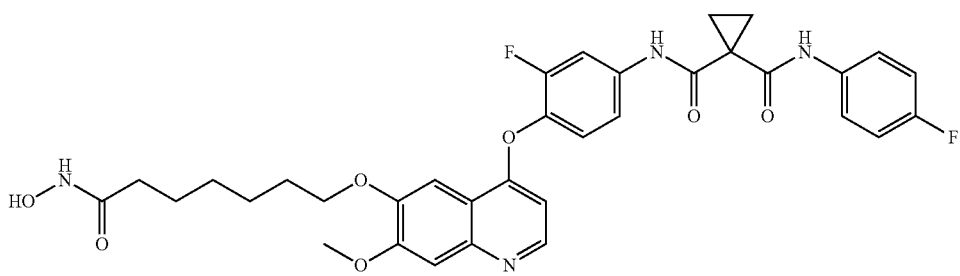 [SMILES: COc1cc2nccc(Oc3ccc(NC(=O)C4(C(=O)Nc5ccc(F)cc5)CC4)cc3F)c2cc1OCCCCCCC(=O)NO]

The preparation was performed according to the same method as Example 15 using Intermediate H. The characterization of the resulting product was as follows: Mass spectrum m/z: 649.2 [M+H].

Example 17

Screening Experiments for Kinase Inhibition

The inhibition results of the compound, N1'-[3-fluoro-4-[[7-[6-(hydroxyamino)-6-oxohexyloxy]-6-methoxy-4-quinolyl]oxy]phenyl]-N1-(4-fluorophenyl)cyclopropane-1,1-dicarboxamide prepared in Example 13 in KinomeScan™ (www.kinomescan.com), a division of DiscoveRx Company (4215 Sorrento Valley Blvd, San Diego, Calif. 92121) 96-kinase panel at a compound concentration of 1000 nM were shown in Table 5.

The details of the screening technology were described in Fabian, M. A. et al, *Nat., Biotechnol.* 2005, 23, 329 and Karaman, M. W. et al, *Nat., Biotechnol.* 2008, 26, 127. From the above representative results, it can be seen that the compounds of the present invention have potent inhibitory activities on kinases including ALK, AXL, VEGFR2, PDGFR-α, PDGFR-β, c-KIT, Flt3, MEK1, MEK2, CSF1R, EPHA2, EPHA2, MKNK2, SRC, TIE2 and their mutants. Accordingly, the compounds of the present invention can be used for the treatment of diseases caused by abnormal activities of these kinases, e.g., cancer, psoriasis, hepatic cirrhosis, diabetes, diseases involving angiogenesis, eye diseases, immune system diseases, cardiovascular diseases, and so forth.

TABLE 5

| Kinase Target Ambit Gene Symbol | Example 13 % Ctrl@1000 nM |
|---|---|
| ABL1(E255K)-phosphorylated | 7.8 |
| ABL1(T315I)-phosphorylated | 19 |
| ABL1-phosphorylated | 4.8 |
| ACVR1B | 90 |
| ADCK3 | 100 |
| AKT1 | 100 |
| AKT2 | 100 |
| ALK | 1.2 |
| AURKA | 5.2 |
| AURKB | 7 |
| AXL | 1.2 |
| BMPR2 | 100 |
| BRAF | 87 |
| BRAF(V600E) | 88 |
| BTK | 2.6 |
| CDK11 | 1.2 |
| CDK2 | 73 |
| CDK3 | 100 |
| CDK7 | 5.8 |
| CDK9 | 67 |
| CHEK1 | 96 |

TABLE 5-continued

| Kinase Target Ambit Gene Symbol | Example 13 % Ctrl@1000 nM |
|---|---|
| CSF1R | 0 |
| CSNK1D | 54 |
| CSNK1G2 | 99 |
| DCAMKL1 | 100 |
| DYRK1B | 63 |
| EGFR | 6.8 |
| EGFR(L858R) | 5.7 |
| EPHA2 | 0.9 |
| ERBB2 | 15 |
| ERBB4 | 17 |
| ERK1 | 94 |
| FAK | 12 |
| FGFR2 | 65 |
| FGFR3 | 64 |
| FLT3 | 0.85 |
| GSK3B | 100 |
| IGF1R | 21 |
| IKK-alpha | 100 |
| IKK-beta | 78 |
| INSR | 6 |
| JAK2 (JH1domain-catalytic) | 64 |
| JAK3 (JH1domain-catalytic) | 76 |
| JNK1 | 100 |
| JNK2 | 62 |
| JNK3 | 100 |
| KIT | 0 |
| KIT (D816V) | 2.2 |
| KIT (V559D, T670I) | 0.15 |
| LKB1 | 91 |
| MAP3K4 | 100 |
| MAPKAPK2 | 67 |
| MARK3 | 73 |
| MEK1 | 0.95 |
| MEK2 | 1.8 |
| MET | 7.7 |
| MKNK1 | 8.8 |
| MKNK2 | 0.1 |
| MLK1 | 32 |
| p38-alpha | 43 |
| p38-beta | 78 |
| PAK1 | 66 |
| PAK2 | 76 |
| PAK4 | 100 |
| PCTK1 | 100 |
| PDGFRA | 1.8 |
| PDGFRB | 0 |
| PDPK1 | 87 |
| PIK3C2B | 99 |
| PIK3CA | 100 |
| PIK3CG | 66 |
| PIM1 | 100 |
| PIM2 | 100 |
| PIM3 | 100 |
| PKAC-alpha | 100 |
| PLK1 | 100 |
| PLK3 | 100 |
| PLK4 | 0.55 |

TABLE 5-continued

| Kinase Target Ambit Gene Symbol | Example 13 % Ctrl@1000 nM |
|---|---|
| PRKCE | 100 |
| RAF1 | 53 |
| RET | 0 |
| RIOK2 | 100 |
| ROCK2 | 53 |
| RSK2 (Kin.Dom.1-N-terminal) | 96 |
| SNARK | 91 |
| SRC | 0.15 |
| SRPK3 | 76 |
| TGFBR1 | 85 |
| TIE2 | 0.55 |
| TRKA | 0.5 |
| TSSK1B | 50 |
| TYK2 (JH1domain-catalytic) | 98 |
| ULK2 | 100 |
| VEGFR2 | 1 |
| YANK3 | 84 |
| ZAP70 | 80 |

Example 18

The Kinase Inhibitory Activity in Tumor Cells

This example shows that the inhibitory activity of the compound, N1'-[3-fluoro-4-[[7-[4-(hydroxyamino)-4-oxobutoxy]-6-methoxy-4-quinolyl]oxy]phenyl]-N1-(4-fluorophenyl)cyclopropane-1,1-dicarboxamide prepared in Example 9 in cells against kinases including ALK, AXL, FLT3, VEGFR2, c-KIT, c-MET, PDGFR-β, RET and SRC (tested by Advanced Cellular Dynamics, 3550 General Atomics Court, Building 2, Room 639, San Diego, Calif. 92121. www.advancedcelldynamics.com and Carna Biosciences, Inc. (www.carnabio.com)) measured according to the method described in the literature (Reference: Daley, G. Q.; Baltimore, D. *Proc. Natl. Acd. Sci.* USA 1988, 85(23), 9312). Specific steps were as follows:

The compound of the present invention was dissolved in dimethyl sulfoxide (DMSO) to make a stock solution of 2 mM, then the stock solution was diluted with DMSO following a 7 half-log series to concentrations ranging from 2 µM to 600 pM.

Test Method:

Cell lines were maintained in RPMI-1640 culture solution containing 10% fetal bovine serum and antibiotics. Logarithmic growth phase cells were used and plated in a 384 well-plate containing 50 µL of growth medium, with 5000 cells per well. 50 nanoliters of the diluted compound was added into a suitable well in duplicates. The cells were incubated in a humidified culture dish containing 5% $CO_2$ atmosphere for 48 hours at 37° C. 15 µL CellTiter-GLO was added and the activity was determined by measurement of luminescence.

Test Results:

$IC_{50}$ values of the compound prepared in Example 9 of the present invention for inhibition of nine kinases in cells were shown in Table 6:

TABLE 6

| Compound prepared in Example 9 | |
|---|---|
| Kinases | Inhibition on kinases in cells, $IC_{50}$ (µM) |
| ALK | >0.63 |
| AXL | 0.019 |
| FLT3 | 0.031 |
| VEGFR2 | 0.012 |
| c-KIT | 0.115 |
| c-MET | 0.119 |
| PDGFR-β | 0.172 |
| RET | 0.154 |
| SRC | >0.63 |

From the above data, it can be seen that, the compounds of the present invention have potent inhibitory activities on several kinases in tumor cells, i.e. AXL, FLT3, VEGFR2, c-KIT, c-MET, PDGFR-β and RET, and the $IC_{50}$ values ranged from 12 nM to 154 nM. Therefore, the compounds of the present invention can be used for the treatment of diseases caused by the abnormal activities of these kinases, such as cancer, psoriasis, liver cirrhosis, diabetes, diseases involving angiogenesis, eye diseases, immune system disorders, cardiovascular disease, and so on.

Example 19

Inhibitory Activities Against 11 Isoforms of the HDAC Enzymes

The inhibitions of activities of HDAC enzymes by the compounds N1'-[3-fluoro-4-[[7-[4-(hydroxyamino)-4-oxobutoxy]-6-methoxy-4-quinolyl]oxy]phenyl]-N1-(4-fluorophenyl)cyclopropane-1,1-dicarboxamide prepared in Example 9 and N1'-[3-fluoro-4-[[7-[6-(hydroxyamino)-6-oxohexyloxy]-6-methoxy-4-quinolyl]oxy]phenyl]-N1-(4-fluorophenyl)cyclopropane-1,1-dicarboxamide prepared in Example 13 were measured by Reaction Biology Corporation (Reaction Biology Corp., One Great Valley Parkway, Suite 2, Malvern, Pa. 19355, USA. http://www.reactionbiology.com/pages/hdac.htm). The HDAC enzymes tested include the following 11 HDAC isoforms: HDAC1, HDAC2, HDAC3, HDAC4, HDAC5, HDAC6, HDAC7, HDAC8, HDAC9, HDAC10 and HDAC11.

Specific steps were as follows:

The compound of the present invention was dissolved in dimethyl sulfoxide (DMSO) to make a stock solution of 10 mM. The stock solution was diluted in 4-fold series starting from 10 mM to prepare 10 different dosages. The substrate for testing HDAC8 activity was polypeptide RHK(Ac)K(Ac) prepared from p53 residues 379-382. The substrate for testing 2A-type HDAC activity was Boc-Lys(trifluoroacetyl)-AMC. The substrates for the remaining tests were polypeptide RHKK(Ac) prepared from p53 residues 379-382.

Measurement Results:

$IC_{50}$ value of inhibiting 11 isoforms of HDAC enzymes by the compounds prepared in Example 9 and 13 were showed in Table 7:

TABLE 7

| HDAC isoforms | IC$_{50}$ (μM) | |
| --- | --- | --- |
| | Compound prepared in Example 9 | Compound prepared in Example 13 |
| HDAC1 | >10 | >10 |
| HDAC2 | 0.431 | 2.74 |
| HDAC3 | >10 | >10 |
| HDAC4 | >10 | >10 |
| HDAC5 | >10 | >10 |
| HDAC6 | 0.242 | 0.0083 |
| HDAC7 | >10 | >10 |
| HDAC8 | 8.94 | 1.63 |
| HDAC9 | >10 | >10 |
| HDAC10 | >10 | 11.9 |
| HDAC11 | >10 | 6.13 |

From the above data, it can be seen that the compound of the present invention prepared in Example 9 exerts a strong inhibition activity on HDAC2 and HDAC6 with IC$_{50}$ values of 431 nM and 242 nM, respectively. The compound prepared in Example 13 selectively inhibits the activity of HDAC6 with an IC$_{50}$ of 8.3 nM. Thus, the compounds of the present invention can be used for the treatment of these diseases caused by abnormal activities of HDAC enzymes, such as cancer, epilepsy, neurodegenerative diseases, Alzheimer's disease, Huntington's disease or Parkinson's disease.

Example 20

Anti-Tumor Experiment

In this example, N1'-[3-fluoro-4-[[7-[[1-[2-(hydroxyamino)-2-oxoethyl]-4-piperidyl]methoxy]-6-methoxy-4-quinolyl]oxy]phenyl]-N1-(4-fluorophenyl)cyclopropane-1,1-dicarboxamide prepared in Example 1 was used to conduct anti-tumor experiment in xenograft nude mice animal models of human gastric cancer. The method and results of the experiment were as follows.

Experiment Materials:

4 to 5-week-old SPF level female BALB/c-nu/nu mice with body weight of 12 g to 16 g were purchased from Beijing Vital River Laboratory Animal Technology Co., Ltd., with the production license number: SCXK (Beijing) 2006. GTL-16 gastric cancer cells were purchased from Shanghai Institutes for Biological Sciences Cell Resource Center. RPM 1-1640 cell culture media, fetal bovine serum (FBS) and trypsin digestion solution were purchased from Gibco. Various antibiotics were purchased from Sigma.

Experiment Method:

GTL-16 gastric cancer cells were firstly cultured: GTL-16 cell lines were inoculated in RPM 1-1640 culture medium contain 10% FBS, 100 U/ml penicillin, 100 U/ml streptomycin and cultured under the condition of 37° C., 5% CO$_2$ and 100% humidity in a carbon dioxide incubator. The logarithmic growth phase reached upon 24 h, and the cells completely covered the bottom of the culture flask at approximately 48 h after inoculation. Those with 80% of GTL-16 cells covering the bottom of the culture flask were digested and centrifuged at 1000 r/min for 5 min. The cells were diluted to 2×10$^7$/ml, and implanted subcutaneously in the right anterior axillary of the nude mice at 0.1 mL per mouse. Starting from 12 days after inoculation of tumor cells, the weight of the tumor-bearing nude mice and the size of tumors were measured, and the mice with tumor sizes ranging from 150-200 mm$^3$ were randomly divided into vehicle control group (Vehicle was 0.25% methanesulfonic acid) and treatment group in which the mice were treated with N1'-[3-fluoro-4-[[7-[[1-[2-(hydroxyamino)-2-oxoethyl]-4-piperidyl]methoxy]-6-methoxy-4-quinolyl]oxy]phenyl]-N1-(4-fluorophenyl)cyclopropane-1,1-dicarboxamide prepared in Example 1 with 6 mice each group. Thereafter, the nude mice were weighed daily and the oral administrations were performed at 0.1 mL/10 g body-weight through oral gavage method (75 mg/kg, once a day). The tumor size of each animal was measured every 2 days. 14 days later, the tumor-bearing mice were sacrificed by cervical dislocation and the tumors were removed and weighed. The calculation method of Tumor Growth Inhibition (TGI) was as follows: the experimental data were represented by mean±SD; TGI=[(V$_{vehicle\ group}$−V$_{treatment\ group}$)÷V$_{vehicle\ group}$]×100%, wherein V$_{vehicle\ group}$ represented the mice tumor volume of the vehicle group and V$_{treatment\ group}$ represented the mice tumor volume of the treatment group.

Experiment Results:

The inhibitory effect of the compound in Example 1 on mice tumor growth in the treatment group: after the animals of the vehicle group and the treatment group were administered with the vehicle and the compound respectively for 14 days, the average tumor volumes of animals in the vehicle group and the treatment group were 1811.2±245.6 mm$^3$ (the number of mice in each group n=6) and 630.9±354.6 mm$^3$ (the number of mice in each group n=6), respectively. Thus, the Tumor Growth Inhibition (TGI) of the treatment group was 65%.

Figure 2:
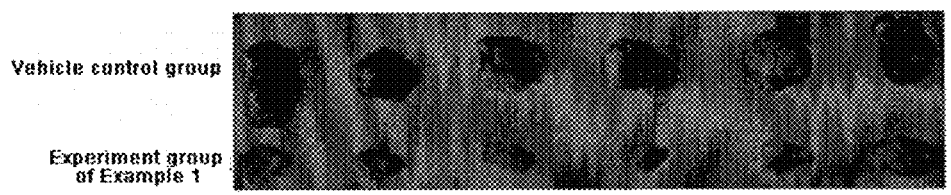
FIG. 2 is a comparison of pictures of tumors in the mouse anti-tumor experiment by the compound of the present invention in Example 1.

A picture of tumors showing the inhibitory effect of the compound of the present invention in Example 1 was illustrated in FIG. 2: The treatment group showed a significant tumor growth inhibition as compared to the tumor volume of the vehicle control group.

Figure 3:
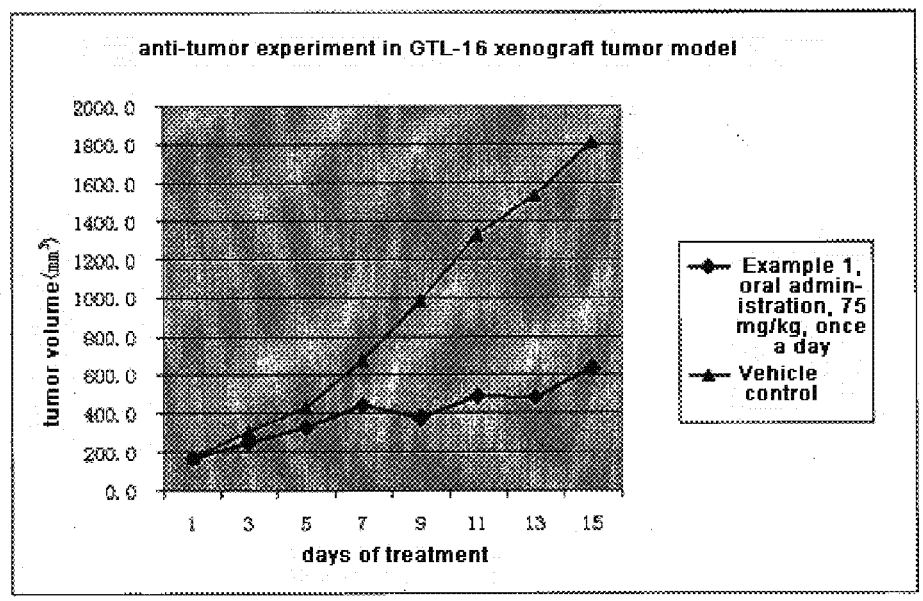
FIG. 3 is a comparison of curves of tumor volumes in the mouse anti-tumor experiment by the compound of the present invention in Example 1.
Figure 4:
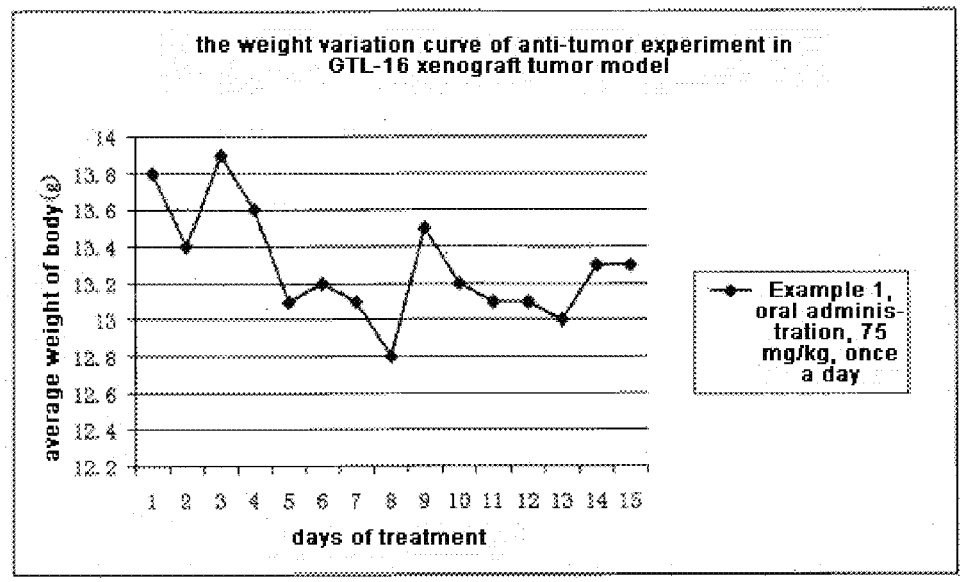
FIG. 4 is a comparison of body weights of mice in the anti-tumor experiments treated with vehicle or the compound of the present invention in Example 1.

A curve of tumor volumes showing the inhibitory effect of the compound of the present invention in Example 1 was illustrated in FIG. 3: the tumor volumes of the treatment group were significantly smaller than that of the control group;

A body weight variations of mice of the vehicle group and the treatment group in the tumor growth inhibition experiment of the compound of the present invention in Example 1 was illustrated in FIG. 4: after 14 days treatment, the mice of the treatment group treated with the compound in Example 1 had a weight variation of <10%.

From the above anti-tumor experiment results, the representative compounds of the present invention showed significant tumor growth inhibition effect in xenograft nude mice animal models. Tumor Growth Inhibition was up to 65% upon 14 days of oral administration once a day. The body weight variation of the treatment group was minor, which demonstrated that the compound had no significant toxicity.

Example 21

Anti-Tumor Experiment

The anti-tumor experiment was performed using the same method as in Example 20. The compound prepared in Example 9, N1'-[3-fluoro-4-[[7-[4-(hydroxyamino)-4-oxobutoxy]-6-methoxy-4-quinolyl]oxy]phenyl]-N1-(4-fluorophenyl)cyclopropane-1,1-dicarboxamide, was used in this example. The tumor model was xenograft nude mice animal model of GTL-16 gastric cancer.

Experiment Results:

The inhibitory effect of the compound in Example 9 on mice tumor growth in the treatment group: after the animals of the vehicle group and the treatment groups were administered with the vehicle and the compound for 14 days, the average tumor volumes of animals of the vehicle group and the treatment group were 1811.2±245.6 mm³ (the number of mice in each group n=6) and 241.1±131.4 mm³ (the number of mice in each group n=6), respectively. Thus, the Tumor Growth Inhibition (TGI) of the treatment group was 87%. The treatment group showed a significant tumor growth inhibition as compared to the tumor volume of the vehicle control group. The tumor and tumor volume curves comparisons were respectively illustrated in FIGS. 5 and 6.

Figure 5:
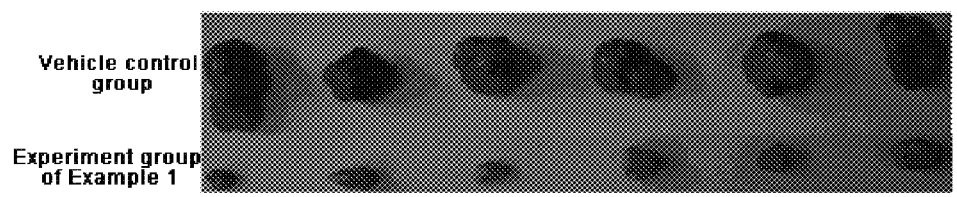
FIG. 5 is a comparison of pictures of tumors in the mouse anti-tumor experiment by the compound of the present invention in Example 9.
Figure 6:
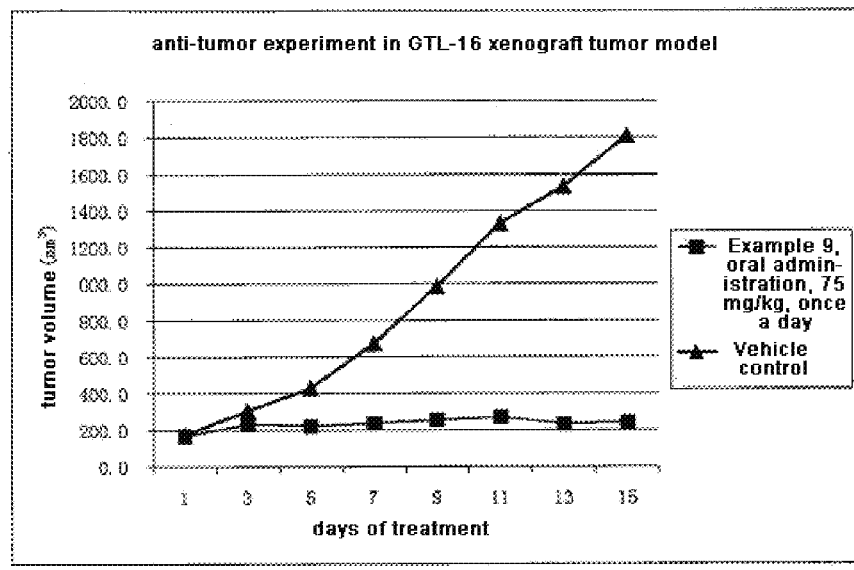
FIG. 6 is a comparison of curves of tumor volumes in the mouse anti-tumor experiment by the compound of the present invention in Example 9.
Figure 7:
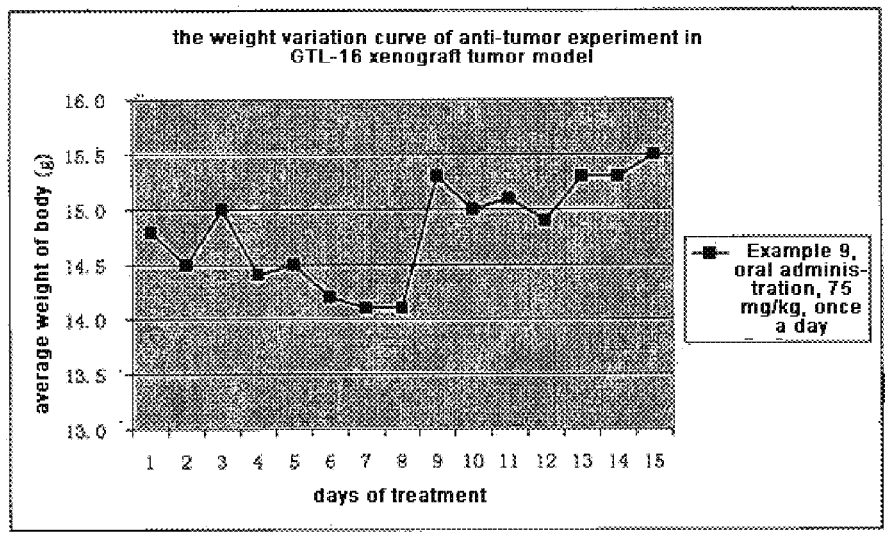
FIG. 7 is a comparison of pictures of tumors in the mouse anti-tumor experiment by the compound of the present invention in Example 9.

A picture of tumors showing the inhibitory effect of the compound of the present invention in Example 9 was illustrated in FIG. 5: The treatment group showed a significant tumor growth inhibition as compared to the tumor volume of the vehicle control group;

A curve of tumor volumes showing the inhibitory effect of the compound of the present invention in Example 9 was illustrated in FIG. 6: the tumor volumes of the treatment group were significantly smaller than those of the vehicle control group;

Body weight variations of mice of the vehicle group and the treatment group in the tumor growth inhibition experiment of the compound of the present invention in Example 1 were illustrated in FIG. 7: after 14 days treatment, the mice of the treatment group treated with the compound in Example 9 had a significant decrease in tumor volume.

From the above anti-tumor experiment results, the representative compound of the present invention showed significant tumor growth inhibition effect in xenograft nude mice animal models. Tumor Growth Inhibition was up to 87% upon 14 days of oral administration once a day. The body weights of animals of the treatment group were not decreased, which demonstrated that the compound had no significant toxicity.

Example 22

Composition and formulation of the drug: tablet (mg/tablet)

The compound prepared in Example 1: 100; lactose, Ph EUR: 182.75;

sodium carboxymethylcellulose: 12.0; corn starches (5 w/v %): 2.25;

magnesium stearate: 3.0;

Applicable user: people with diseases caused by abnormal activity of protein kinase and/or histone deacetylase.

Example 23

Composition and formulation of the drug: tablet (mg/tablet)

The compound prepared in Example 5: 100, the contents of the other substances are the same as in Example 22;

Applicable user: people with diseases caused by abnormal activity of protein kinase and/or histone deacetylase.

Example 24

Composition and formulation of the drug: tablet (mg/tablet)

The compound prepared in Example 9: 50; lactose, Ph EUR: 223.75;

sodium carboxymethylcellulose: 6.0; corn starch: 15.0;

polyvinylpyrrolidone (5 w/v %): 2.25; magnesium stearate: 3.0;

Applicable user: people with diseases caused by abnormal activity of protein kinase and/or histone deacetylase.

Example 25

Composition and formulation of the drug: tablet (mg/tablet)

The compound prepared in Example 9: 50, the content of the other substances are the same as in Example 24;

Applicable user: people with diseases caused by abnormal activity of protein kinase and/or histone deacetylase.

Example 26

Composition and formulation of the drug: tablet (mg/tablet)

The compound prepared in Example 13: 1.0; lactose, Ph EUR: 93.25;

sodium carboxymethylcellulose: 4.0; corn starches (5 w/v %): 0.75;

magnesium stearate: 76;

Applicable user: people with diseases caused by abnormal activity of protein kinase and/or histone deacetylase.

Example 27

Composition and formulation of the drug: tablet (mg/tablet)

Example 13: 1.0, the content of the other substances are the same as in Example 26;

Applicable user: people with diseases caused by abnormal activity of protein kinase and/or histone deacetylase.

Example 28

Composition and formulation of the drug: capsule (mg/capsule)

The compound prepared in Example 7: 10.0; lactose, Ph EUR: 488.5;

magnesium: 1.5;

Applicable user: people with diseases caused by abnormal activity of protein kinase and/or histone deacetylase.

Example 29

Composition and formulation of the drug: capsule (mg/capsule)

The compound prepared in Example 2: 10.0, the content of the other substances are the same as in Example 28;

Applicable user: people with diseases caused by abnormal activity of protein kinase and/or histone deacetylase.

Example 30

Composition and formulation of the drug: injection (50 mg/mL)

The compound prepared in Example 6: 5%; 1 M sodium hydroxide: 15%;

0.1 M HCl solution (adjust pH to pH=7.6); polyethylene glycol 400: 5%;

Adjusted to 100% with water for injection;

Applicable user: people with diseases caused by abnormal activity of protein kinase and/or histone deacetylase.

Example 31

Composition and formulation of the drug: injection (50 mg/mL)

The compound prepared in Example 12: 5%, the content of the other substances are the same as in Example 30, finally adjusted to 100% with water for injection 100%;

Applicable user: people with diseases caused by abnormal activity of protein kinase and/or histone deacetylase.

Example 32

Composition and formulation of the drug: injection (10 mg/mL)

The compound prepared in Example 11: 1%; disodium hydrogen phosphate BP: 3.6%;

0.1 M sodium hydroxide: 15%; adjusted to 100% with water for injection;

Applicable user: people with diseases caused by abnormal activity of protein kinase and/or histone deacetylase.

Example 33

Composition and formulation of the drug: injection (10 mg/mL)

The compound prepared in Example 9: 1%, the content of the other substances are the same as in Example 32, adjusted to 100% with water for injection;

Applicable user: people with diseases caused by abnormal activity of protein kinase and/or histone deacetylase.

Example 34

Composition and formulation of the drug: injection (1 mg/mL) (pH is adjusted to pH=6)

The compound prepared in Example 6: 0.1%; disodium hydrogen phosphate BP: 2.26%;

citric acid: 0.38%; polyethylene glycol 400: 3.5%;

adjusted to 100% with water for injection;

Applicable user: people with diseases caused by abnormal activity of protein kinase and/or histone deacetylase.

Example 35

Composition and formulation of the drug: injection (1 mg/mL) (pH is adjusted to pH=6)

The compound prepared in Example 10: 0.1%, the content of the other substances as in Example 34, finally adjusted to 100% with water for injection 100%;

Applicable user: people with diseases caused by abnormal activity of protein kinase and/or histone deacetylase.

Example 36

Composition and formulation of the drug: aerosol (mg/mL)

The compound prepared in Example 1: 10; sorbitan monooleate: 13.5;

trichlorofluoromethane: 910.0; dichlorodifluoromethane: 490.0;

Applicable user: people with diseases caused by abnormal activity of protein kinase and/or histone deacetylase.

Example 37

Composition and formulation of the drug: aerosol (mg/mL)

The compound prepared in Example 3: 10, the content of the other substances are the same as in Example 36;

Applicable user: people with diseases caused by abnormal activity of protein kinase and/or histone deacetylase.

Example 38

Composition and formulation of the drug: aerosol (mg/mL)

The compound prepared in Example 4: 0.2; sorbitan monooleate: 0.27;

trichlorofluoromethane: 70.0; dichlorodifluoromethane: 280.0;

dichlorotetrafluoroethane: 1094.0;

Applicable user: people with diseases caused by abnormal activity of protein kinase and/or histone deacetylase.

Example 39

Composition and formulation of the drug: aerosol (mg/mL)

The compound prepared in Example 7: 0.2, the content of the other substances are the same as in Example 38;

Applicable user: people with diseases caused by abnormal activity of protein kinase and/or histone deacetylase.

Example 40

Composition and formulation of the drug: aerosol (mg/mL)

The compound prepared in Example 8: 2.5; sorbitan monooleate: 3.38;

trichlorofluoromethane: 67.5; dichlorodifluoromethane: 1086.0;

dichlorotetrafluoroethane: 191.60;

Applicable user: people with diseases caused by abnormal activity of protein kinase and/or histone deacetylase.

Example 41

Composition and formulation of the drug: aerosol (mg/mL)

The compound prepared in Example 11: 2.5, the content of the other substances are the same as in Example 40;

Applicable user: people with diseases caused by abnormal activity of protein kinase and/or histone deacetylase.

Example 42

Composition and formulation of the drug: aerosol (mg/mL)

The compound prepared in Example 4: 2.5; Soybean Lecithin: 2.7;

trichlorofluoromethane: 67.5; dichlorodifluoromethane: 1086.0;

dichlorotetrafluoroethane: 191.60;

Applicable user: people with diseases caused by abnormal activity of protein kinase and/or histone deacetylase.

Example 43

Composition and formulation of the drug: aerosol (mg/mL)

The compound prepared in Example 13: 2.5, the content of the other substances are the same as in Example 42;

Applicable user: people with diseases caused by abnormal activity of protein kinase and/or histone deacetylase.

Example 44

Composition and formulation of the drug: ointment (/mL)
The compound prepared in Example 1: 40 mg; ethanol: 300 μL;
water: 300 μL; 1-dodecylazepanone: 50 μL
propylene glycol: to 1 mL;
Applicable user: people with diseases caused by abnormal activity of protein kinase and/or histone deacetylase.

Example 45

Composition and formulation of the drug: ointment (/mL)
The compound prepared in Example 7: 40 mg, the content of the other substances are the same as in Example 44;
Applicable user: people with diseases caused by abnormal activity of protein kinase and/or histone deacetylase.

The invention claimed is:

1. A quinolyl-containing hydroxamic acid compound, having the molecular structure of formula (I) below:

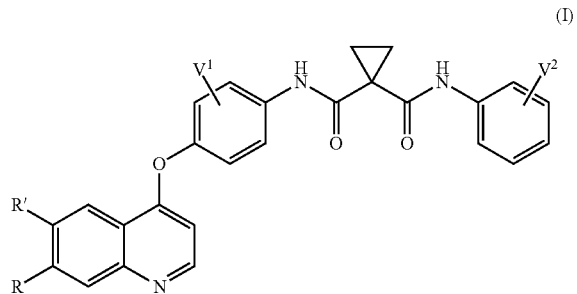

(I)

wherein,
either of $V^1$ or $V^2$ is a hydrogen, halogen, —$OCF_3$, —$CF_3$, —$NO_2$, —CN, —OH, —$NH_2$, —$NMe_2$, $C_{1-6}$alkyl, $C_{2-6}$ alkenyl, $C_{2-6}$ alkynyl, $C_{3-6}$cycloalkyl, $C_{3-12}$ heteroalicyclyl, $C_{1-6}$ alkoxy, $C_{3-6}$ cycloalkyloxy or $C_{3-12}$heteroalicyclyloxy group;
either of R or R' is a hydroxamic acid-containing Q group and the other is a hydrogen, methoxy, methoxyethoxy or the hydroxamic acid-containing Q group, wherein the hydroxamic acid-containing Q group is

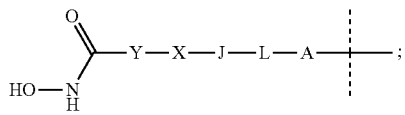

A is O, NH, S(═O)$_m$, $C_{1-6}$ alkyl, or A is absent, and the hydrogen of A may be substituted with $G^1$;
L is $C_{1-6}$ alkyl, $C_{2-6}$ alkenyl, $C_{2-6}$ alkynyl, $C_{3-6}$cycloalkyl, $C_6$ aryl, $C_{5-6}$ heteroaryl, $C_{3-12}$ heteroalicyclyl, or L is absent, and the hydrogen of L may be substituted with $G^2$;
J is O, NH, S(═O)$_m$, $C_{1-6}$ alkyl, $C_{2-6}$ alkenyl, $C_{2-6}$ alkynyl, $C_{3-6}$cycloalkyl, $C_6$ aryl, $C_{5-6}$ heteroaryl, $C_{3-12}$ heteroalicyclyl, or J is absent, and the hydrogen of J may be substituted with $G^3$;
X is —C(═O)—, —S(O)$_m$, $C_{1-6}$ alkyl, $C_{2-6}$ alkenyl, $C_{2-6}$ alkynyl, $C_{3-6}$cycloalkyl, $C_6$ aryl, $C_{5-6}$ heteroaryl, $C_{3-12}$ heteroalicyclyl, or X is absent, and the hydrogen of X may be substituted with $G^4$;
Y is $C_{1-6}$ alkyl, $C_{2-6}$ alkenyl, $C_{2-6}$ alkynyl, $C_{3-6}$cycloalkyl, $C_6$ aryl, $C_{5-6}$ heteroaryl, $C_{3-12}$ heteroalicyclyl, or Y is absent, and the hydrogen of Y may be substituted with $G^5$;
wherein,
each of $G^1$, $G^2$, $G^3$, W and $G^5$ is H, —CN, —$CF_3$, —$CO_2H$, halogen, $C_{1-6}$ alkyl, $C_{3-6}$cycloalkyl, $C_{2-6}$ alkenyl, $C_{2-6}$ alkynyl, $C_6$ aryl, $C_{5-6}$ heteroaryl, $C_{3-12}$ heteroalicyclyl, $R^1O$—, $R^1R^2N$—, $R^1S(═O)_m$—, $R^1R^2NS(═O)_m$—, $R^3C(═O)$—, $R^1R^2NC(═O)$—, $R^1OC(═O)$—, $R^3C(═O)O$—, $R^1R^2NC(═O)O$—, $R^3C(═O)NR^1$—, $R^1R^2NC(═O)NR^4$—, $R^1OC(═O)NR^4$—, $R^1S(═O)_mNR^4$—, $R^1R^2NS(═O)_mNR^4$—, $R^1R^2NC(═NR^5)NR^4$—, $R^1R^2NC(═CHNO_2)NR^4$—, $R^1R^2NC(═N—CN)NR^4$—, $R^1R^2NC(═NR^5)$—, $R^1S(═O)(═NR^5)NR^4$— or $R^1R^2NS(═O)(═NR^5)$—;
each of $R^1$, $R^2$, $R^3$, W and $R^5$ is H, $C_{1-6}$ alkyl, $C_{2-6}$ alkenyl, $C_{2-6}$ alkynyl, $C_{3-6}$cycloalkyl, $C_6$ aryl, $C_{5-6}$ heteroaryl or $C_{3-12}$ heteroalicyclyl; when $R^1$ and $R^2$ are connected with the same nitrogen atom, they may form a $C_{3-12}$ heteroalicyclyl ring together with the nitrogen atom they are attached to, and this $C_{3-12}$ heteroalicyclyl ring may further comprise one or more hetero atom selected from O, N, or S(═O)$_m$; the hydrogen of $R^1$, $R^2$, $R^3$, W and $R^5$ may be substituted with halogen, CN, $C_{1-6}$ alkyl or $C_{3-6}$ cycloalkyl; and
m=0-2.

2. The quinolyl-containing hydroxamic acid compound according to claim 1, wherein the structure of the compound is formula (Ia) below:

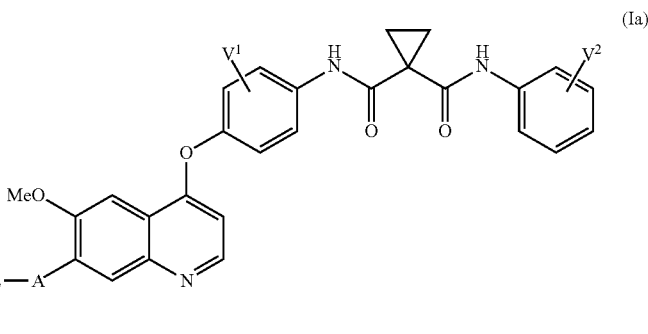

(Ia)

wherein,
each of V¹ and V² is a hydrogen, halogen, —OCF₃, —CF₃, —CN, —NMe₂, C₁₋₆alkyl, C₃₋₆ cycloalkyl, C₃₋₁₂ heteroalicyclyl, C₁₋₆ alkoxy, C₃₋₆ cycloalkyloxy or C₃₋₁₂heteroalicyclyloxy group;
A is O, NH, or S(=O)$_m$, and the hydrogen of A may be substituted with G¹;
L is C₁₋₆ alkyl or C₃₋₆cycloalkyl, and the hydrogen of L may be substituted with G²;
J is O, NH, or S(=O)$_m$, and the hydrogen of J may be substituted with G³;
Y is C₁₋₆ alkyl or C₃₋₆cycloalkyl, and the hydrogen of Y may be substituted with G⁵; and
m=0-2.

3. The quinolyl-containing hydroxamic acid compound according to claim 1, wherein the structure of the compound is formula (Ib) below:

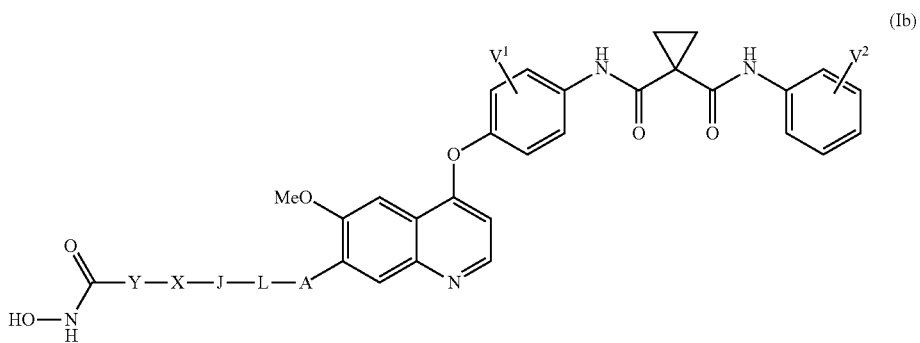

(Ib)

wherein,
each of V¹ and V² is hydrogen, halogen, —OCF₃, —CF₃, —CN, —NMe₂, C₁₋₆alkyl, C₃₋₆ cycloalkyl, C₃₋₁₂ heteroalicyclyl, C₁₋₆ alkoxy, C₃₋₆ cycloalkyloxy or C₃₋₁₂heteroalicyclyloxy group;
A is O, NH, or S(=O)$_m$, and the hydrogen of A may be substituted with G¹;
L is C₁₋₆ alkyl, and the hydrogen of L may be substituted with G²;
J is C₃₋₆cycloalkyl or C₃₋₁₂ heteroalicyclyl, and the hydrogen of J may be substituted with G³;
X is —C(=O)—, —S(=O)$_m$ or X is absent;
Y is C₁₋₆ alkyl or C₃₋₆cycloalkyl, and the hydrogen of Y may be substituted with G⁵; and
m=0-2.

4. The quinolyl-containing hydroxamic acid compound according to claim 1, wherein the structure of the compound is formula (Ic) below:

wherein,
each of V¹ and V² is a hydrogen, halogen, —OCF₃, —CF₃, —CN, —NMe₂, C₁₋₆alkyl, C₃₋₆ cycloalkyl, C₃₋₁₂ heteroalicyclyl, C₁₋₆ alkoxy, C₃₋₆ cycloalkyloxy or C₃₋₁₂heteroalicyclyloxy group;
A is O, NH, or S(=O)$_m$, and the hydrogen of A may be substituted with G¹;
L is C₁₋₆ alkyl or C₃₋₆cycloalkyl, and the hydrogen of L may be substituted with G²;
J is O, NH, or S(=O)$_m$, and the hydrogen of J may be substituted with G³;
Y is C₁₋₆ alkyl or C₃₋₆cycloalkyl, and the hydrogen of Y may be substituted with G⁵; and
m=0-2.

5. The quinolyl-containing hydroxamic acid compound according to claim 1, wherein the structure of the compound is represented by the formula (Id) below:

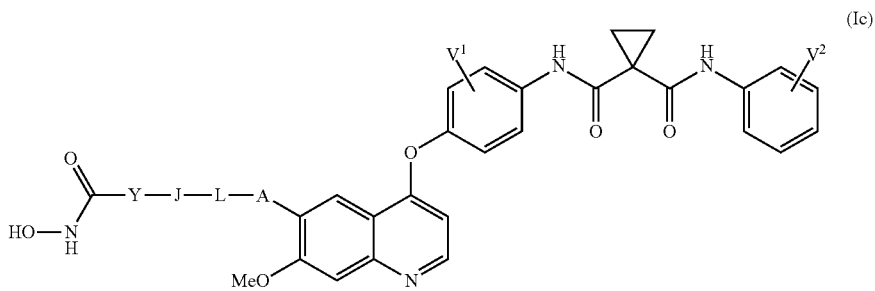

(Ic)

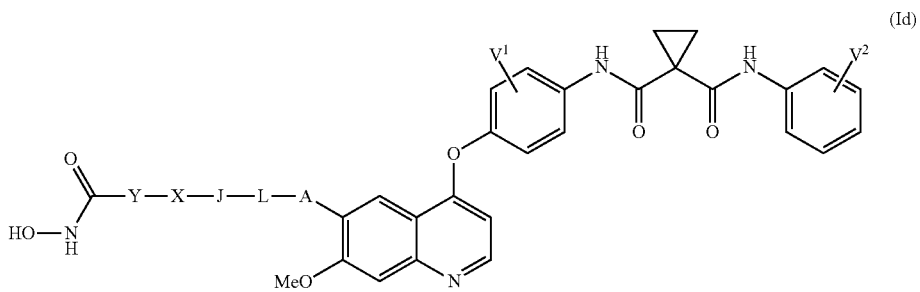

(Id)

wherein,
each of $V^1$ and $V^2$ is a hydrogen, halogen, —$OCF_3$, —$CF_3$, —CN, —$NMe_2$, $C_{1-6}$alkyl, $C_{3-6}$ cycloalkyl, $C_{3-12}$ heteroalicyclyl, $C_{1-6}$ alkoxy, $C_{3-6}$ cycloalkyloxy or $C_{3-12}$heteroalicyclyloxy group;

A is O, NH, or S(=O)$_m$, and the hydrogen of A may be substituted with $G^1$;

L is $C_{1-6}$ alkyl, and the hydrogen of L may be substituted with $G^2$;

J is $C_{3-6}$cycloalkyl or $C_{3-12}$ heteroalicyclyl, and the hydrogen of J may be substituted with $G^3$;

X is —C(=O)—, —S(=O)$_m$, or X is absent;

Y is $C_{1-6}$ alkyl or $C_{3-6}$cycloalkyl, and the hydrogen of Y may be substituted with $G^5$; and m=0-2.

6. The quinolyl-containing hydroxamic acid compound according to claim 1, wherein the structure of the compound is represented by the formula (Ie) below:

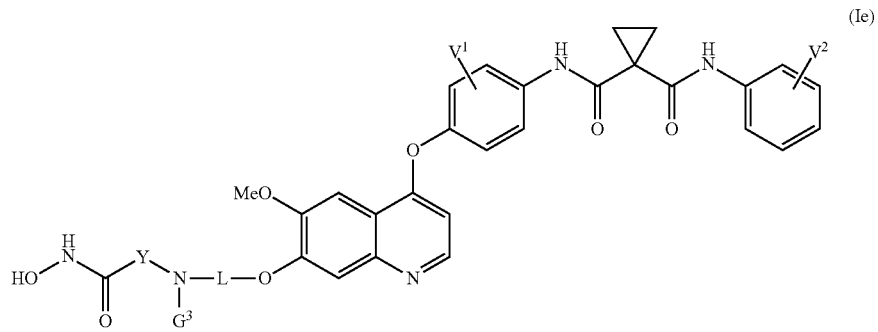

(Ie)

wherein,
each of $V^1$ and $V^2$ is a hydrogen, halogen, —$OCF_3$, —$CF_3$, —CN, —$NMe_2$, $C_{1-6}$alkyl, $C_{3-6}$ cycloalkyl, $C_{3-12}$ heteroalicyclyl, $C_{1-6}$ alkoxy, $C_{3-6}$ cycloalkyloxy or $C_{3-12}$heteroalicyclyloxy group;

L is $C_{1-6}$ alkyl or $C_{3-6}$cycloalkyl, and the hydrogen of L may be substituted with $G^2$; and Y is $C_{1-6}$ alkyl or $C_{3-6}$cycloalkyl, and the hydrogen of Y may be substituted with $G^5$.

7. The quinolyl-containing hydroxamic acid compound according to claim 1, wherein the structure of the compound formula (If) below:

(If)

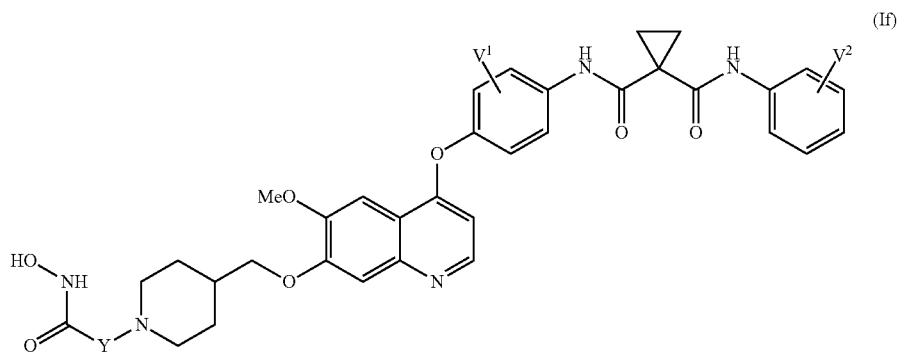

wherein,
each of V[1] and V[2] is a hydrogen, halogen, —OCF$_3$, —CF$_3$, —CN, —NMe$_2$, C$_{1-6}$alkyl, C$_{3-6}$ cycloalkyl, C$_{3-12}$ heteroalicyclyl, C$_{1-6}$ alkoxy, C$_{3-6}$ cycloalkyloxy or C$_{3-12}$heteroalicyclyloxy group;
Y is C$_{1-6}$ alkyl or C$_{3-6}$cycloalkyl; and
the hydrogen of Y may be substituted with G[5].

8. The quinolyl-containing hydroxamic acid compound according to claim 1, wherein the structure of the compound is formula (Ig) below:

(Ig)

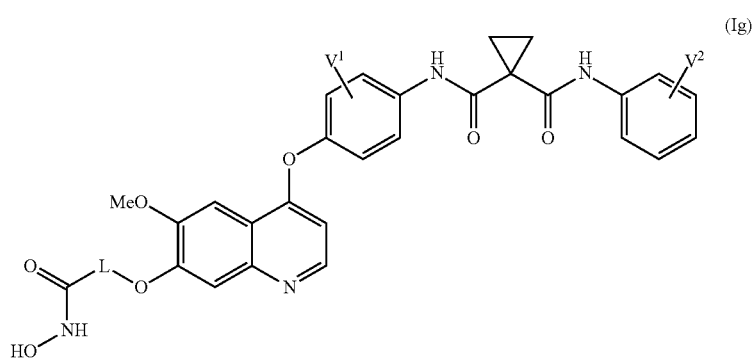

wherein,
each of V[1] and V[2] is a hydrogen, halogen, —OCF$_3$, —CF$_3$, —CN, —NMe$_2$, C$_{1-6}$alkyl, C$_{3-6}$ cycloalkyl, C$_{3-12}$ heteroalicyclyl, C$_{1-6}$ alkoxy, C$_{3-6}$ cycloalkyloxy or C$_{3-12}$heteroalicyclyloxy group;
L is C$_{1-6}$ alkyl or C$_{3-6}$cycloalkyl; and
the hydrogen of L may be substituted with G[2].

9. The quinolyl-containing hydroxamic acid compound according to claim 1, wherein the structure of the compound is formula (Ih) below:

(Ih)

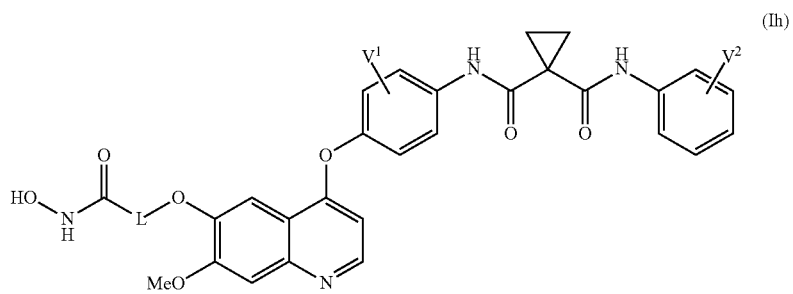

wherein, each of V¹ and V² is a hydrogen, halogen, —OCF₃, —CF₃, —CN, —NMe₂, C₁₋₆alkyl, C₃₋₆ cycloalkyl, C₃₋₁₂ heteroalicyclyl, C₁₋₆ alkoxy, C₃₋₆ cycloalkyloxy or C₃₋₁₂heteroalicyclyloxy group;

L is C₁₋₆ alkyl or C₃₋₆cycloalkyl; and the hydrogen of L may be substituted with G².

10. The quinolyl-containing hydroxamic acid compound according to claim 1, wherein the structure of the compound is formula (Ii) below:

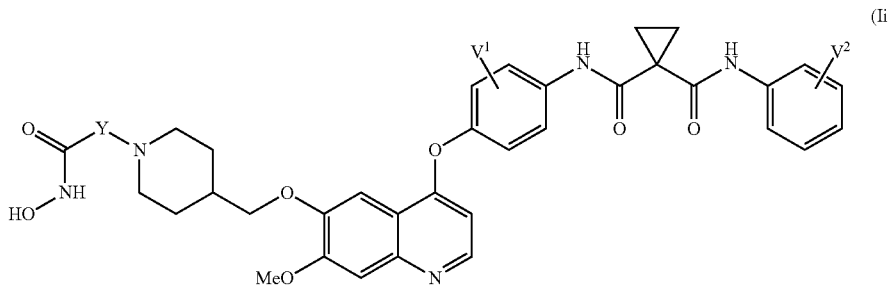

wherein, each of V¹ and V² is a hydrogen, halogen, —OCF₃, —CF₃, —CN, —NMe₂, C₁₋₆alkyl, C₃₋₆ cycloalkyl, C₃₋₁₂ heteroalicyclyl, C₁₋₆ alkoxy, C₃₋₆ cycloalkyloxy or C₃₋₁₂heteroalicyclyloxy group;

Y is C₁₋₆ alkyl or C₃₋₆cycloalkyl; and the hydrogen of Y may be substituted with G⁵.

11. The quinolyl-containing hydroxamic acid compound according to claim 1, wherein the compound is:

N1'-[3-fluoro-4-[[7-[[1-[2-(hydroxyamino)-2-oxoethyl]-4-piperidinyl]methoxy]-6-methoxy-4-quinolyl]oxy]phenyl]-N1-(4-fluorophenyl)cyclopropane-1,1-dicarboxamide;

N1'-[3-fluoro-4-[[7-3-[[2-(hydroxyamino)-2-oxoethyl]amino]propoxy]-6-methoxy-4-quinolyl]oxy]phenyl]-N1-(4-fluorophenyl)cyclopropane-1,1-dicarboxamide;

N1'-[3-fluoro-4-[[7-[3-[[3-(hydroxyamino)-3-oxopropyl]amino]propoxy]-6-methoxy-4-quinolyl]oxy]phenyl]-N1-(4-fluorophenyl)cyclopropane-1,1-dicarboxamide;

N1'-[3-fluoro-4-[[7-[2-(hydroxyamino)-2-oxoethoxy]-6-methoxy-4-quinolyl]oxy]phenyl]-N1-(4-fluorophenyl)cyclopropane-1,1-dicarboxamide;

N1'-[3-fluoro-4-[[7-[3-(hydroxyamino)-3-oxopropoxy]-6-methoxy-4-quinolyl]oxy]phenyl]-N1-(4-fluorophenyl)cyclopropane-1,1-dicarboxamide;

N1'-[3-fluoro-4-[[7-[4-(hydroxyamino)-4-oxobutoxy]-6-methoxy-4-quinolyl]oxy]phenyl]-N1-(4-fluorophenyl)cyclopropane-1,1-dicarboxamide;

N1'-[3-fluoro-4-[[7-[5-(hydroxyamino)-5-oxopentyloxy]-6-methoxy-4-quinolyl]oxy]phenyl]-N1-(4-fluorophenyl)cyclopropane-1,1-dicarboxamide;

N1'-[3-fluoro-4-[[7-[6-(hydroxyamino)-6-oxohexyloxy]-6-methoxy-4-quinolyl]oxy]phenyl]-N1-(4-fluorophenyl)cyclopropane-1,1-dicarboxamide;

N1'-[3-fluoro-4-[[7-[7-(hydroxyamino)-7-oxoheptyloxy]-6-methoxy-4-quinolyl]oxy]phenyl]-N1-(4-fluorophenyl)cyclopropane-1,1-dicarboxamide;

N1'-[3-fluoro-4-[[6-[[1-[2-(hydroxyamino)-2-oxoethyl]-4-piperidinyl]methoxy]-7-methoxy-4-quinolyl]oxy]phenyl]-N1-(4-fluorophenyl)cyclopropane-1,1-dicarboxamide;

N1'-[3-fluoro-4-[[6-[3-[[2-(hydroxyamino)-2-oxoethyl]amino]propoxy]-7-methoxy-4-quinolyl]oxy]phenyl]-N1-(4-fluorophenyl)cyclopropane-1,1-dicarboxamide;

N1'-[3-fluoro-4-[[6-[3-[[3-(hydroxyamino)-3-oxopropyl]amino]propoxy]-7-methoxy-4-quinolyl]oxy]phenyl]-N1-(4-fluorophenyl)cyclopropane-1,1-dicarboxamide;

N1'-[3-fluoro-4-[[6-[2-(hydroxyamino)-2-oxoethoxy]-7-methoxy-4-quinolyl]oxy]phenyl]-N1-(4-fluorophenyl)cyclopropane-1,1-dicarboxamide;

N1'-[3-fluoro-4-[[6-[3-(hydroxyamino)-3-oxopropoxy]-7-methoxy-4-quinolyl]oxy]phenyl]-N1-(4-fluorophenyl)cyclopropane-1,1-dicarboxamide;

N1'-[3-fluoro-4-[[6-[4-(hydroxyamino)-4-oxobutoxy]-7-methoxy-4-quinolyl]oxy]phenyl]-N1-(4-fluorophenyl)cyclopropane-1,1-dicarboxamide;

N1'-[3-fluoro-4-[[6-[5-(hydroxyamino)-5-oxopentyloxy]-7-methoxy-4-quinolyl]oxy]phenyl]-N1-(4-fluorophenyl)cyclopropane-1,1-dicarboxamide;

N1'-[3-fluoro-4-[[6-[6-(hydroxyamino)-6-oxohexyloxy]-7-methoxy-4-quinolyl]oxy]phenyl]-N1-(4-fluorophenyl)cyclopropane-1,1-dicarboxamide;

N1'-[3-fluoro-4-[[6-[7-(hydroxyamino)-7-oxoheptyloxy]-7-methoxy-4-quinolyl]oxy]phenyl]-N1-(4-fluorophenyl)cyclopropane-1,1-dicarboxamide;

N1'-(4-fluorophenyl)-N1-[4-[[7-[[1-[2-(hydroxyamino)-2-oxoethyl]-4-piperidinyl]methoxy]-6-methoxy-4-quinolyl]oxy]phenyl]cyclopropane-1,1-dicarboxamide;

N1'-(4-fluorophenyl)-N1-[4-[[7-[3-[[2-(hydroxyamino)-2-oxoethyl]amino]propoxy]-6-methoxy-4-quinolyl]oxy]phenyl]cyclopropane-1,1-dicarboxamide;

N1'-(4-fluorophenyl)-N1-[4-[[7-[3-[[3-(hydroxyamino)-3-oxopropyl]amino]propoxy]-6-methoxy-4-quinolyl]oxy]phenyl]cyclopropane-1,1-dicarboxamide;

N1'-(4-fluorophenyl)-N1-[4-[[7-[2-(hydroxyamino)-2-oxoethoxy]-6-methoxy-4-quinolyl]oxy]phenyl]cyclopropane-1,1-dicarboxamide;

N1'-(4-fluorophenyl)-N1-[4-[[7-[3-(hydroxyamino)-3-oxopropoxy]-6-methoxy-4-quinolyl]oxy]phenyl]cyclopropane-1,1-dicarboxamide;

N1'-(4-fluorophenyl)-N1-[4-[[7-[4-(hydroxyamino)-4-oxobutoxy]-6-methoxy-4-quinolyl]oxy]phenyl]cyclopropane-1,1-dicarboxamide;

N1'-(4-fluorophenyl)-N1-[4-[[7-[5-(hydroxyamino)-5-oxopentyloxy]-6-methoxy-4-quinolyl]oxy]phenyl]cyclopropane-1,1-dicarboxamide;

N1'-(4-fluorophenyl)-N1-[4-[[7-[6-(hydroxyamino)-6-oxohexyloxy]-6-methoxy-4-quinolyl]oxy]phenyl]cyclopropane-1,1-dicarboxamide;

N1'-(4-fluorophenyl)-N1-[4-[[7-[7-(hydroxyamino)-7-oxoheptyloxy]-6-methoxy-4-quinolyl]oxy]phenyl]cyclopropane-1,1-dicarboxamide;

N1'-(4-fluorophenyl)-N1-[4-[[6-[[1-[2-(hydroxyamino)-2-oxoethyl]-4-piperidinyl]methoxy]-7-methoxy-4-quinolyl]oxy]phenyl]cyclopropane-1,1-dicarboxamide;

N1'-(4-fluorophenyl)-N1-[4-[[6-[3-[[2-(hydroxyamino)-2-oxoethyl]amino]propoxy]-7-methoxy-4-quinolyl]oxy]phenyl]cyclopropane-1,1-dicarboxamide;

N1'-(4-fluorophenyl)-N1-[4-[[6-[3-[[3-(hydroxyamino)-3-oxopropyl]amino]propoxy]-7-methoxy-4-quinolyl]oxy]phenyl]cyclopropane-1,1-dicarboxamide;

N1'-(4-fluorophenyl)-N1-[4-[[6-[2-(hydroxyamino)-2-oxoethoxy]-7-methoxy-4-quinolyl]oxy]phenyl]cyclopropane-1,1-dicarboxamide;

N1'-(4-fluorophenyl)-N1-[4-[[6-[3-(hydroxyamino)-3-oxopropoxy]-7-methoxy-4-quinolyl]oxy]phenyl]cyclopropane-1,1-dicarboxamide;

N1'-(4-fluorophenyl)-N1-[4-[[6-[4-(hydroxyamino)-4-oxobutoxy]-7-methoxy-4-quinolyl]oxy]phenyl]cyclopropane-1,1-dicarboxamide;

N1'-(4-fluorophenyl)-N1-[4-[[6-[5-(hydroxyamino)-5-oxopentyloxy]-7-methoxy-4-quinolyl]oxy]phenyl]cyclopropane-1,1-dicarboxamide;

N1'-(4-fluorophenyl)-N1-[4-[[6-[6-(hydroxyamino)-6-oxohexyloxy]-7-methoxy-4-quinolyl]oxy]phenyl]cyclopropane-1,1-dicarboxamide; or N1'-(4-fluorophenyl)-N1-[4-[[6-[7-(hydroxyamino)-7-oxoheptyloxy]-7-methoxy-4-quinolyl]oxy]phenyl]cyclopropane-1,1-dicarboxamide.

12. The quinolyl-containing hydroxamic acid compound according to claim 1, wherein the compound:

N1'-[3-fluoro-4-[[7-[[1-[2-(hydroxyamino)-2-oxoethyl]-4-piperidinyl]methoxy]-6-methoxy-4-quinolyl]oxy]phenyl]-N1-(4-fluorophenyl)cyclopropane-1,1-dicarboxamide;

N1'-[3-fluoro-4-[[7-[3-[[2-(hydroxyamino)-2-oxoethyl]amino]propoxy]-6-methoxy-4-quinolyl]oxy]phenyl]-N1-(4-fluorophenyl)cyclopropane-1,1-dicarboxamide;

N1'-[3-fluoro-4-[[7-[3-[[3-(hydroxyamino)-3-oxopropyl]amino]propoxy]-6-methoxy-4-quinolyl]oxy]phenyl]-N1-(4-fluorophenyl)cyclopropane-1,1-dicarboxamide;

N1'-[3-fluoro-4-[[7-[2-(hydroxyamino)-2-oxoethoxy]-6-methoxy-4-quinolyl]oxy]phenyl]-N1-(4-fluorophenyl)cyclopropane-1,1-dicarboxamide;

N1'-[3-fluoro-4-[[7-[3-(hydroxyamino)-3-oxopropoxy]-6-methoxy-4-quinolyl]oxy]phenyl]-N1-(4-fluorophenyl)cyclopropane-1,1-dicarboxamide;

N1'-[3-fluoro-4-[[7-[4-(hydroxyamino)-4-oxobutoxy]-6-methoxy-4-quinolyl]oxy]phenyl]-N1-(4-fluorophenyl)cyclopropane-1,1-dicarboxamide;

N1'-[3-fluoro-4-[[7-[5-(hydroxyamino)-5-oxopentyloxy]-6-methoxy-4-quinolyl]oxy]phenyl]-N1-(4-fluorophenyl)cyclopropane-1,1-dicarboxamide;

N1'-[3-fluoro-4-[[7-[6-(hydroxyamino)-6-oxohexyloxy]-6-methoxy-4-quinolyl]oxy]phenyl]-N1-(4-fluorophenyl)cyclopropane-1,1-dicarboxamide;

N1'-[3-fluoro-4-[[7-[7-(hydroxyamino)-7-oxoheptyloxy]-6-methoxy-4-quinolyl]oxy]phenyl]-N1-(4-fluorophenyl)cyclopropane-1,1-dicarboxamide;

N1'-(4-fluorophenyl)-N1-[4-[[7-[[1-[2-(hydroxyamino)-2-oxoethyl]-4-piperidinyl]methoxy]-6-methoxy-4-quinolyl]oxy]phenyl]cyclopropane-1,1-dicarboxamide;

N1'-(4-fluorophenyl)-N1-[4-[[7-[3-[[2-(hydroxyamino)-2-oxoethyl]amino]propoxy]-6-methoxy-4-quinolyl]oxy]phenyl]cyclopropane-1,1-dicarboxamide;

N1'-(4-fluorophenyl)-N1-[4-[[7-[3-[[3-(hydroxyamino)-3-oxopropyl]amino]propoxy]-6-methoxy-4-quinolyl]oxy]phenyl]cyclopropane-1,1-dicarboxamide;

N1'-(4-fluorophenyl)-N1-[4-[[7-[2-(hydroxyamino)-2-oxoethoxy]-6-methoxy-4-quinolyl]oxy]phenyl]cyclopropane-1,1-dicarboxamide;

N1'-(4-fluorophenyl)-N1-[4-[[7-[3-(hydroxyamino)-3-oxopropoxy]-6-methoxy-4-quinolyl]oxy]phenyl]cyclopropane-1,1-dicarboxamide;

N1'-(4-fluorophenyl)-N1-[4-[[7-[4-(hydroxyamino)-4-oxobutoxy]-6-methoxy-4-quinolyl]oxy]phenyl]cyclopropane-1,1-dicarboxamide;

N1'-(4-fluorophenyl)-N1-[4-[[7-[5-(hydroxyamino)-5-oxopentyloxy]-6-methoxy-4-quinolyl]oxy]phenyl]cyclopropane-1,1-dicarboxamide;

N1'-(4-fluorophenyl)-N1-[4-[[7-[6-(hydroxyamino)-6-oxohexyloxy]-6-methoxy-4-quinolyl]oxy]phenyl]cyclopropane-1,1-dicarboxamide; or N1'-(4-fluorophenyl)-N1-[4-[[7-[7-(hydroxyamino)-7-oxoheptyloxy]-6-methoxy-4-quinolyl]oxy]phenyl]cyclopropane-1,1-dicarboxamide.

13. The quinolyl-containing hydroxamic acid compound according to claim 1, wherein the compound is:

N1'-[3-fluoro-4-[[7-[[1-[2-(hydroxyamino)-2-oxoethyl]-4-piperidinyl]methoxy]-6-methoxy-4-quinolyl]oxy]phenyl]-N1-(4-fluorophenyl)cyclopropane-1,1-dicarboxamide;

N1'-[3-fluoro-4-[[7-[4-(hydroxyamino)-4-oxobutoxy]-6-methoxy-4-quinolyl]oxy]phenyl]-N1-(4-fluorophenyl)cyclopropane-1,1-dicarboxamide;

N1'-[3-fluoro-4-[[7-[5-(hydroxyamino)-5-oxopentyloxy]-6-methoxy-4-quinolyl]oxy]phenyl]-N1-(4-fluorophenyl)cyclopropane-1,1-dicarboxamide;

N1'-[3-fluoro-4-[[7-[6-(hydroxyamino)-6-oxohexyloxy]-6-methoxy-4-quinolyl]oxy]phenyl]-N1-(4-fluorophenyl)cyclopropane-1,1-dicarboxamide;

N1'-(4-fluorophenyl)-N1-[4-[[7-[[1-[2-(hydroxyamino)-2-oxoethyl]-4-piperidinyl]methoxy]-6-methoxy-4-quinolyl]oxy]phenyl]cyclopropane-1,1-dicarboxamide;

N1'-(4-fluorophenyl)-N1-[4-[[7-[4-(hydroxyamino)-4-oxobutoxy]-6-methoxy-4-quinolyl]oxy]phenyl]cyclopropane-1,1-dicarboxamide;

N1'-(4-fluorophenyl)-N1-[4-[[7-[5-(hydroxyamino)-5-oxopentyloxy]-6-methoxy-4-quinolyl]oxy]phenyl]cyclopropane-1,1-dicarboxamide; or N1'-(4-fluorophenyl)-N1-[4-[[7-[6-(hydroxyamino)-6-oxohexyloxy]-6-methoxy-4-quinolyl]oxy]phenyl]cyclopropane-1,1-dicarboxamide.

14. Racemates or enantiomers of the quinolyl-containing hydroxamic acid compounds according to claim 1.

15. A method of preparing the quinolyl-containing hydroxamic acid compound according to claim 1, consisting of the steps shown in Scheme 1:

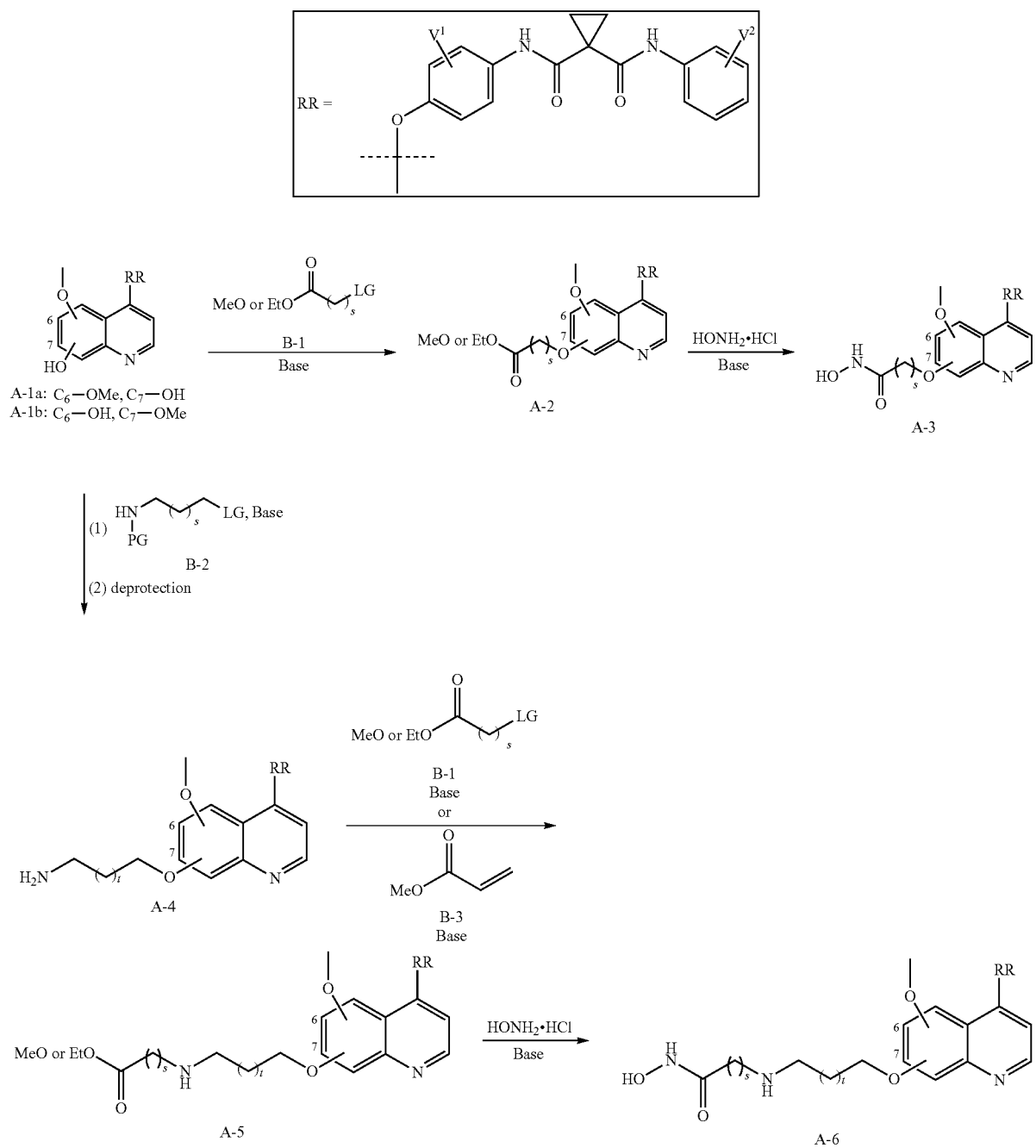

wherein, t=0-6;

s=1-10;

each of $V^1$ and $V^2$ is a hydrogen, halogen, —OCF$_3$, —CF$_3$, —CN, —NMe$_2$, C$_{1-6}$alkyl, C$_{3-6}$ cycloalkyl, C$_{3-12}$ heteroalicyclyl, C$_{1-6}$ alkoxy, C$_{3-6}$ cycloalkyloxy or C$_{3-12}$heteroalicyclyloxy group;

LG is any one of F, Cl, Br, I, MsO, TsO or TfO; and

PG is Boc or CBZ.

16. A method of preparing the quinolyl-containing hydroxamic acid compound according to claim 1, consisting of the steps shown in Scheme 2:

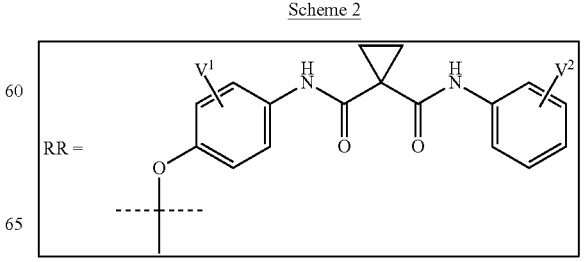

-continued

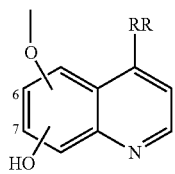
A-1a: C_6—OMe, C_7—OH
A-1b: C_6—OH, C_7—OMe

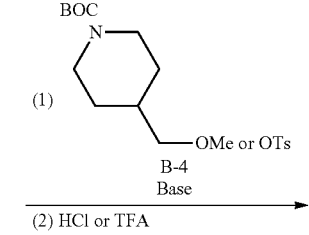
(1) $\underset{\text{B-4}}{\text{BOC-N-piperidine-CH}_2\text{—OMe or OTs}}$
Base
(2) HCl or TFA

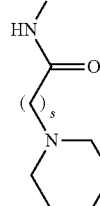

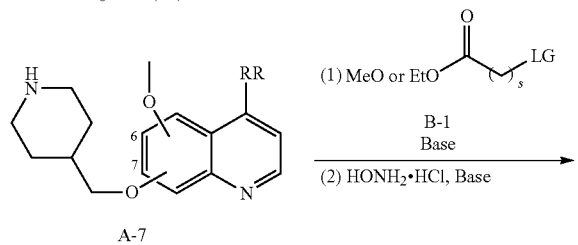
A-7
(1) MeO or EtO—C(O)—(CH_2)_s—LG
B-1
Base
(2) HONH_2·HCl, Base

-continued

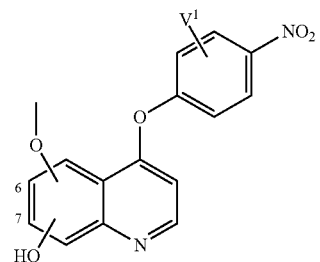
A-8 wherein each of $V^1$ and $V^2$ is a hydrogen, halogen, —OCF_3, —CF_3, —CN, —NMe_2, $C_{1-6}$alkyl, $C_{3-6}$cycloalkyl, $C_{3-12}$ heteroalicyclyl, $C_{1-6}$ alkoxy, $C_{3-6}$ cycloalkyloxy or $C_{3-12}$heteroalicyclyloxy group; and s=1-10.

17. A method of preparing the quinolyl-containing hydroxamic acid compound of claim 1, consisting of the steps shown in Scheme 3:

Scheme 3

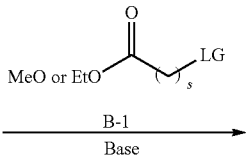

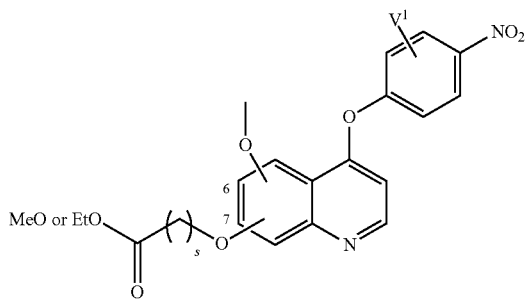
A-9a: C_6—OMe, C_7—OH
A-9b: C_6—OH, C_7—OMe

MeO or EtO—C(O)—(CH_2)_s—LG
B-1
Base

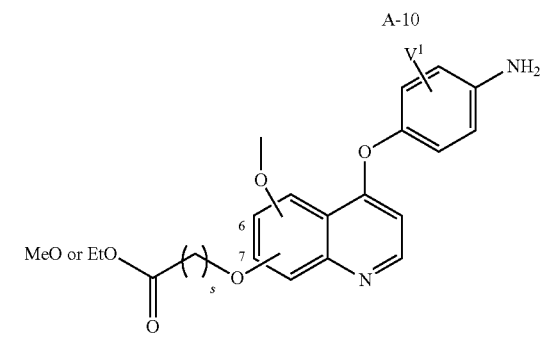
A-10

Reduction

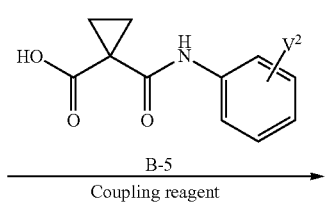

B-5
Coupling reagent

A-11

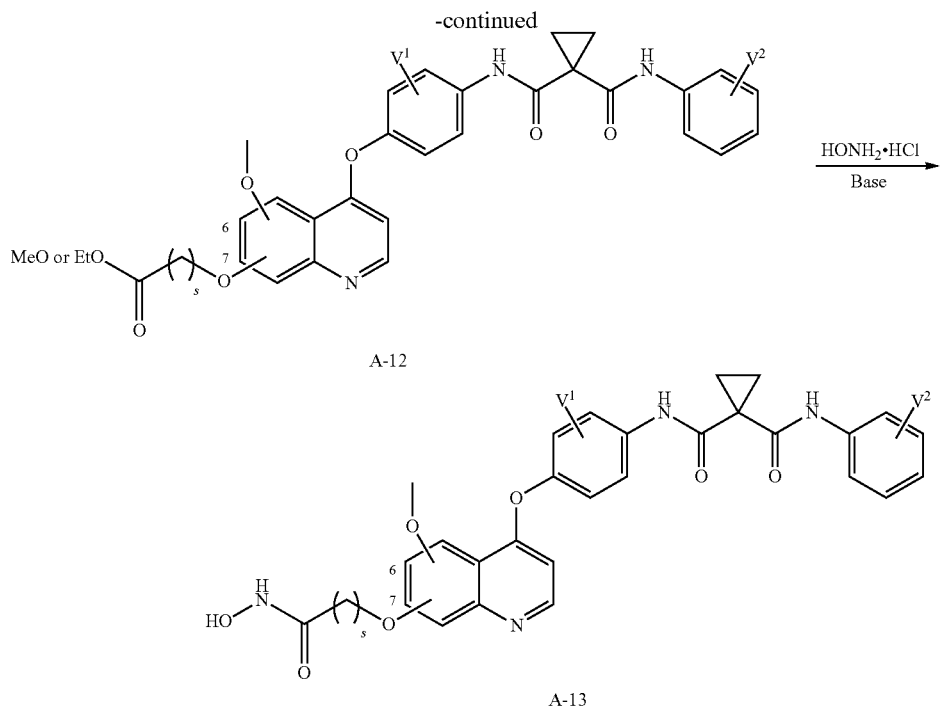

A-12

A-13 wherein each of $V^1$ and $V^2$ is a hydrogen, halogen, —OCF$_3$, —CF$_3$, —CN, —NMe$_2$, C$_{1-6}$alkyl, C$_{3-6}$cycloalkyl, C$_{3-12}$ heteroalicyclyl, C$_{1-6}$ alkoxy, C$_{3-6}$ cycloalkyloxy or C$_{3-12}$heteroalicyclyloxy group; and s=1-10.

18. A method of treating a disease caused by at least one of abnormal activity of protein kinase and histone deacetylase comprising:

administering a pharmaceutical composition comprising a quinolyl-containing hydroxamic acid compound having the molecular structure of formula (I) below:

(I)

wherein,
either of $V^1$ or $V^2$ is a hydrogen, halogen, —OCF$_3$, —CF$_3$, —NO$_2$, —CN, —OH, —NH$_2$, —NMe$_2$, C$_{1-6}$alkyl, C$_{2-6}$ alkenyl, C$_{2-6}$ alkynyl, C$_{3-6}$cycloalkyl, C$_{3-12}$ heteroalicyclyl, C$_{1-6}$ alkoxy, C$_{3-6}$ cycloalkyloxy or C$_{3-12}$heteroalicyclyloxy group;

either of R or R' is a hydroxamic acid-containing Q group and the other is a hydrogen, methoxy, methoxyethoxy or the hydroxamic acid-containing Q group, wherein the hydroxamic acid-containing Q group is

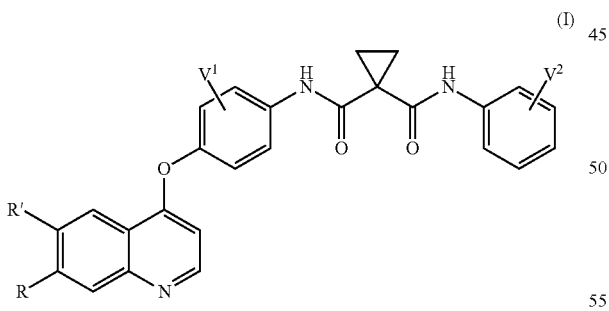

A is O, NH, S(=O)$_m$, C$_{1-6}$ alkyl, or A is absent, and the hydrogen of A may be substituted with G$^1$;

L is C$_{1-6}$ alkyl, C$_{2-6}$ alkenyl, C$_{2-6}$ alkynyl, C$_{3-6}$cycloalkyl, C$_6$ aryl, C$_{5-6}$ heteroaryl, C$_{3-12}$ heteroalicyclyl, or L is absent, and the hydrogen of L may be substituted with G$^2$;

J is O, NH, S(=O)$_m$, C$_{1-6}$ alkyl, C$_{2-6}$ alkenyl, C$_{2-6}$ alkynyl, C$_{3-6}$cycloalkyl, C$_6$ aryl, C$_{5-6}$ heteroaryl, C$_{3-12}$ heteroalicyclyl, or J is absent, and the hydrogen of J may be substituted with G$^3$;

X is —C(=O)—, —S(O)$_m$, C$_{1-6}$ alkyl, C$_{2-6}$ alkenyl, C$_{2-6}$ alkynyl, C$_{3-6}$cycloalkyl, C$_6$ aryl, C$_{5-6}$ heteroaryl, C$_{3-12}$ heteroalicyclyl, or X is absent, and the hydrogen of X may be substituted with G$^4$;

Y is C$_{1-6}$ alkyl, C$_{2-6}$ alkenyl, C$_{2-6}$ alkynyl, C$_{3-6}$cycloalkyl, C$_6$ aryl, C$_{5-6}$ heteroaryl, C$_{3-12}$ heteroalicyclyl, or Y is absent, and the hydrogen of Y may be substituted with G$^5$;

wherein,
each of G$^1$, G$^2$, G$^3$, W and G$^5$ is H, —CN, —CF$_3$, —CO$_2$H, halogen, C$_{1-6}$ alkyl, C$_{3-6}$cycloalkyl, C$_{2-6}$ alkenyl, C$_{2-6}$ alkynyl, C$_6$ aryl, C$_{5-6}$ heteroaryl, C$_{3-12}$ heteroalicyclyl, R$^1$O—, R$^1$R$^2$N—, R$^1$S(=O)$_m$—, R$^1$R$^2$NS(=O)$_m$—, R$^3$C(=O)—, R$^1$R$^2$NC(=O)—, R$^1$OC(=O)—, R$^3$C(=O)—, R$^1$R$^2$NC(=O)O—, R$^3$C(=O)NR$^1$—, R$^1$R$^2$NC(=O)NR$^4$—, R$^1$OC(=O)NR$^4$—, R$^1$S(=O)$_m$NR$^4$—, R$^1$R$^2$NS(=O)$_m$NR$^4$—, R$^1$R$^2$NC(=NR$^5$)NR$^4$—, R$^1$R$^2$NC(=CHNO$_2$)NR$^4$—, R$^1$R$^2$NC(=N—CN)NR$^4$—, R$^1$R$^2$NC(=NR$^5$)—, R$^1$S(=O)(=NR$^5$)NR$^4$— or R$^1$R$^2$NS(=O)(=NR$^5$)—;

each of R$^1$, R$^2$, R$^3$, R$^4$ and R$^5$ is H, C$_{1-6}$ alkyl, C$_{2-6}$ alkenyl, C$_{2-6}$ alkynyl, C$_{3-6}$cycloalkyl, C$_6$ aryl, C$_{5-6}$ heteroaryl or $C_{3-12}$ heteroalicyclyl; when $R^1$ and $R^2$ are connected with the same nitrogen atom, they may form a $C_{3-12}$ heteroalicyclyl ring together with the nitrogen atom they are attached to, and this $C_{3-12}$ heteroalicyclyl ring may further comprise one or more hetero atom selected from O, N, or $S(=O)_m$; the hydrogen of $R^1$, $R^2$, $R^3$, $R^4$ and $R^5$ may be substituted with halogen, CN, $C_{1-6}$ alkyl or $C_{3-6}$ cycloalkyl; and m=0-2; and wherein the disease is selected from a group consisting of psoriasis, cirrhosis, diabetes, disease involving inhibiting angiogenesis, and disease involving inhibiting tumor growth.

19. The method of claim 18, wherein the protein kinase is ALK, AXL, VEGFR2, PDGFR-α, PDGFR-β, c-KIT, Flt3, MEK1, MEK2, CSF1R, EPHA2, MKNK2, or SRC.

20. The method of claim 18, wherein the protein kinase is ABL1, AURKA, AURKB, BTK, CDK11, CDK7, EGFR, EGFR(L858R), ERBB2, ERBB4, FAK, MET, PLK4, RET, Tie2, or TRKA.

21. The method of claim 18, wherein the histone deacetylase is HDAC2 or HDAC6.

22. The method of claim 18, wherein the histone deacetylase is HDAC1, HDAC3, HDAC4, HDAC5, HDAC7, HDAC8, HDAC9, HDAC10 or HDAC11.

23. The method claim 18, wherein inhibiting tumor growth comprises administering the compound of claim 1 having the molecular structure of formula (I).

24. A pharmaceutical composition for treating diseases caused by abnormal activity of at least one of protein kinase and histone deacetylase, comprising the compound of claim 1, or the pharmaceutically acceptable salts, solvates, or prodrugs thereof; or the racemates or enantiomers of the compound of claim 1 or the pharmaceutically acceptable salts, or solvates thereof.

25. The pharmaceutical composition according to claim 24, further comprising at least one pharmaceutically acceptable carrier.

26. The pharmaceutical composition according to claim 24, wherein the pharmaceutical composition is in at least one of:
(1) oral form; (2) injection form; (3) rectal suppository form; (4) nasal inhalation form; (5) eye drops form; and (6) skin patch form.

* * * * *